(12) United States Patent
Wong et al.

(10) Patent No.: US 7,846,894 B2
(45) Date of Patent: Dec. 7, 2010

(54) CHINESE HAMSTER APOPTOSIS-RELATED GENES

(75) Inventors: Chee Furng Wong, Centros (SG); Miranda Gek Sim Yap, Centros (SG)

(73) Assignee: Agency for Science, Technology and Research, Centros, Singapore (SG)

(*) Notice: Subject to any disclaimer, the term of this patent is extended or adjusted under 35 U.S.C. 154(b) by 475 days.

(21) Appl. No.: 11/824,740

(22) Filed: Jul. 2, 2007

(65) Prior Publication Data

US 2008/0295190 A1    Nov. 27, 2008

Related U.S. Application Data

(63) Continuation-in-part of application No. PCT/SG2005/000433, filed on Dec. 28, 2005.

(60) Provisional application No. 60/640,333, filed on Dec. 30, 2004.

(51) Int. Cl.
*C07K 14/00* (2006.01)
*A61K 38/00* (2006.01)

(52) U.S. Cl. .......................... 514/2; 530/300

(58) Field of Classification Search ............ None
See application file for complete search history.

(56) References Cited

U.S. PATENT DOCUMENTS

| 5,919,660 | A | 7/1999 | Gross et al. |
| 6,015,712 | A | 1/2000 | Monia et al. |
| 6,586,206 | B1 | 7/2003 | Dixit et al. |
| 2004/0023385 | A1 | 2/2004 | Bennett et al. |
| 2004/0143111 | A1* | 7/2004 | Hillman et al. ............ 536/23.2 |

FOREIGN PATENT DOCUMENTS

WO    WO 99/53743    10/1999

OTHER PUBLICATIONS

Thijn R. Brummelkamp, et al., A System For Stable Expression Of Short Interfering RNAs in Mammalian Cells, Science (2002) vol. 296, p. 550-553.
Luciano D'Adamio, et al., Functional Cloning Of Genes Involved In T-Cell Receptor-Induced Programmed Cell Death, Immunology (1997) vol. 9, p. 17-23.
Theodore G. Gabig, et al., Expression And Chromosomal Localization Of The Requiem Gene, Mammalian Genome (1998) vol. 9, p. 660-665.
Douglas R. Green, Apoptotic Pathways: Paper Wraps Stone Blunts Scissors, Cell (2000) vol. 102, p. 1-4.
Scott M. Hammond, et al., Post-Transcriptional Gene Silencing By Double-Stranded RNA, Genetics (2001) vol. 2, p. 110-119.
Ihn Kyung Jang, et al., Apoptosis-Linked Gene 2-Deficient Mice Exhibit Normal T-Cell Development And Function, Molecular and Cellular Biology (2002) vol. 22, No. 12, p. 4094-4100.
Yong-Sam Jung, et al., Apoptosis-Linked Gene 2 Binds to the Death Domain Of Fas And Dissociates From Fas During Fas-Mediated Apoptosis In Jurkat Cells, Biochemical and Biophysical Research Communications (2001) vol. 288, p. 420-426.
Markus Kaufmann, et al., Identification Of A Basic Surface Area Of The FADD Death Effector Domain Critical For Apoptotic Signaling, FEBS Letters (2002) vol. 527, p. 250-254.
Scott H. Kaufmann, et al., Programmed Cell Death: Alive And Well In The New Millennium, Trends In Cell Biology (2001) vol. 11, No. 12, p. 526-534.
Masahiro Konishi, et al., Molecular Cloning And Expression Of Xenopus Laevis Requiem cDNA[1], Biochimica. Et Biophysica Acta (1999) vol. 1445, p. 172-176.
Haley A. Laken, et al., Understanding And Modulating Apoptosis In Industrial Cell Culture, Current Opinion In Biotechnology (2001) vol. 12, p. 175-179.
Jonas M. la Cour, et al., Up-Regulation of ALG-2 In Hepatomas And Lung Cancer Tissue, American Journal of Pathology (2003) vol. 163, No. 1, p. 81-89.
Shigekazu Nagata, Apoptosis By Death Factor, Cell (1997) vol. 88, p. 355-365.
RV Rao, et al., Coupling Endoplasmic Reticulum Stress To The Cell Death Program, Cell Death and Differentiation (2004) vol. 11, p. 372-380.
Maria van Gurp, et al., Mitochondrial Intermembrane Proteins In Cell Death, Biochemical and Biophysical Research Communications (2003) vol. 304, p. 487-497.
David L. Wheeler, et al., Database Resources Of The National Center For Biotechnology, Nucleic Acids Research (2003) vol. 31, No. 1, p. 28-33.
Nilou Arden, et al., Life And Death In Mammalian Cell Culture: Strategies For Apoptosis Inhibition, TRENDS in Biotechnology (2004) vol. 22, No. 4 p. I74-180.
Theodore G. Gabig, et al., Requiem: A Novel Zinc Finger Gene Essential for Apoptosis in Myeloid Cells, The Journal of Biological Chemistry (1994) vol. 269, No. 47, p. 29515-29519.
Eckart Grabenhorst, et al., Genetic Engineering of Recombinant Glycoproteins and the Glycosylation Pathway in Mammalian Host Cells, Glycoconjugate Journal (1999) vol. 16, p. 81-97.
Hailing Hsu, et al., TRADD-TRAF2 and TRADD-FADD Interactions Define Two Distinct TNF Receptor 1 Signal Transduction Pathways, Cell (1996) vol. 84, p. 299-308.
Joachim Krebs, et al., ALG-2: a $Ca^{2+}$—Binding Modulator Protein Involved in Cell Proliferation and in Cell Death, Biochimica et Biophysica Acta (2002) 1600 p. 68-73.
Alison J. Mastrangelo, et al., Overcoming Apoptosis: New Methods for Improving Protein-Expression Systems, Trends in Biotechnology, Elsevier Publications, (1998) vol. 16, p. 88-95.
Ilja B. Mertsalov, et al., Structure and Expression of Two Members of the D4 Gene Family in Mouse, Mammalian Genome (2000) vol. 11, p. 72-74.

(Continued)

*Primary Examiner*—Anand U Desai
(74) *Attorney, Agent, or Firm*—Frommer Lawrence & Haug LLP; Sandra Kuzmich; Russell A. Garman

(57) ABSTRACT

Provided is an isolated polypeptide comprising a *Cricetulus griseus* sequence capable of mediating apoptosis of a cell, the sequence being selected from a FAIM sequence shown as SEQ ID NO: 1; a FADD sequence shown as SEQ ID NO: 2; a PDCD6 sequence shown as SEQ ID NO: 3; and a Requiem sequence shown as SEQ ID NO: 4.

3 Claims, 32 Drawing Sheets

OTHER PUBLICATIONS

Ernst Rinderknecht, et al., Natural Human Interferon-γ, The Journal of Biological Chemistry (1984) vol. 259, No. 11, p. 6790-6797.

Thomas L. Rothstein, et al., Receptor-Specific Regulation of B-cell Susceptibility to Fas-Mediated Apoptosis and a Novel Fas Apoptosis Inhibitory Molecule, Immunological Reviews (2000) vol. 176, p. 116-133.

Pasquale Vito, et al., Interfering With Apoptosis: $Ca^{2+}$—Binding Protein ALG-2 and Alzheimer's Disease Gene ALG-3, Science (1996) vol. 271, p. 521- 525.

Danny Chee Furng Wong, et al., Transcriptional Profiling of Apoptotic Pathways in Batch and Fed-Batch CHO Cell Cultures, Biotechnology and Bioengineering (2006) vol. 94, No. 2, p. 373-382.

Jianke Zhang, et al., A Mouse Fas-Associated Protein with Homology to the Human Mort1/FADD Protein Is Essential for Fas-Induced Apoptosis, Molecular and Cellular Biology (1996) vol. 16, No. 6, p. 2756-2763.

Abstract: Database Accession No. Q8R6H8: Sole, et al., Fas Apoptotic Inhibitory Molecule 1 (rFAIM), Mar. 15, 2004.

Abstract: Database Accession No. Q61160: FADD Protein (FAS-associating death domain-containing protein) Oct. 25, 2004.

Abstract: Database Accession No. P12815: Programmed Death Protein 6 (Probable calcium-binding protein) Oct. 25, 2004.

Abstract: Database Accession No. Q61103: Zinc-Finger Protein UBI-D4 (Requiem) (Apoptosis Response Zinc Finger Protein) (D4, Zinc and Double PHD Fingers Family 2) Jun. 15, 2004.

Abstract: Database Accession No. BC079662: Mus Musculus Fas Apoptotic Inhibitory Molecule, mRNA cDNA Clone MGC:90708 IMAGE: 30358320), complete cds., Aug. 16, 2004.

Abstract: Database Accession No. AF406779: Rattus Norvegicus FADD/MORTl Protein With Death Effector Domain mRNA, complete cds., Oct. 7, 2002.

Abstract: Database Accession No. BC040079: Mus Musculus Programmed Cell Death 6, mRNA (cDNA clone MGC: 49479 IMAGE:3156800), complete cds., Jun. 30, 2004.

Abstract: Database Accession No. BC012709: Mus Musculus D4, and Double PHD Fingers Family 2, mRNA (cDNA clone MGC:14002 Image:4208205) complete cds., Jun. 29, 2004.

Krebs, J. (1998) The role of calcium in apoptosis. BioMetals, vol. 11, pp. 375-382.

Martinet, W., et.al. (2003) Western array analysis of human atherosclerotic plaques: downregulation of apoptosis-linked gene 2. Cardiovascular Research, vol. 60, pp. 259-267.

Tarabykina, S., et.al. (2004) ALG-2, Multifunctional calcium binding protein? Frontiers in Bioscience, vol. 9 pp. 1817-1832.

\* cited by examiner

D    Suppression of REQUIEM

US 7,846,894 B2

CHINESE HAMSTER APOPTOSIS-RELATED GENES

CROSS-REFERENCE TO RELATED APPLICATIONS

This application is a continuation-in-part of International application no. PCT/SG2005/000433, filed Dec. 28, 2005, published as WO 2006/071200 on Jul. 6, 2006, and claiming priority to U.S. Application No. 60/640,333, filed Dec. 30, 2004.

The foregoing applications, as well as all documents cited in the foregoing applications ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

This invention relates to the fields of biotechnology and molecular biology. The invention particularly relates to novel genes from Chinese hamster, *Cricetulus griseus*, which are involved in the mediation of apoptotic processes.

BACKGROUND OF THE INVENTION

With the completion of the human genome project, more proteins with therapeutic potential are being discovered daily. Many of these new biotherapeutics often require the development of highly productive manufacturing processes to meet global demand. One of the most commonly used cells lines for complex therapeutic biologics production is Chinese Hamster Ovary (CHO) cells which was originally derived from Chinese Hamster (*Cricetulus griseus*).

However, the genome of *Cricetulus griseus* is poorly characterised, and in particular, there is lack of knowledge of genes in that organism which control physiologically important processes.

U.S. Pat. No. 6,562,797 describes a purified mammalian protein designated FADD which has the ability to bind the cytoplasmic region or domain of the Fas receptor. This document also describes methods of regulating FAS-associated apoptosis. However, the only sequences which are disclosed are of human origin.

U.S. Pat. No. 6,683,168 and US Patent Application Publication Number US 2004/0121389 describes the sequences of FAIM sequence in a number of forms: short, long, super long and lung cancer associated. The sequences are human and mouse sequences.

U.S. Pat. No. 6,544,523 sets out the sequence of a DNA encoding a Fas ligand. U.S. Pat. No. 6,451,759 describes a non-cleavable version of such a ligand.

SUMMARY OF THE INVENTION

We describe for the first time the sequences of *Cricetulus griseus* FAIM, FADD, PDCD6 and Requiem.

According to a $1^{st}$ aspect of the present invention, we provide an isolated polypeptide comprising a sequence selected from the following: (a) a cg FAIM sequence having at least 97% sequence identity with a sequence shown in SEQ ID NO: 1; (b) a cgFADD sequence having at least 69% sequence identity with a sequence shown in SEQ ID NO: 2; (c) a cgPDCD6 sequence having at least 89% sequence identity with a sequence shown in SEQ ID NO: 3; (d) a cgRequiem sequence having at least 90% sequence identity with a sequence shown in SEQ ID NO: 4; (e) a sequence being a fragment of at least 15 contiguous residues of any of (a) to (d) above, which is capable of mediating apoptosis of a cell.

There is provided, according to a $2^{nd}$ aspect of the present invention, an isolated polypeptide comprising a *Cricetulus griseus* sequence capable of mediating apoptosis of a cell, the sequence being selected from a cgFAIM sequence shown as SEQ ID NO: 1; a cgFADD sequence shown as SEQ ID NO: 2; a cgPDCD6 sequence shown as SEQ ID NO: 3; and a cgRequiem sequence shown as SEQ ID NO: 4.

According to a $1^{st}$ aspect of the present invention, we provide an isolated polypeptide comprising a *Cricetulus griseus* sequence capable of mediating apoptosis of a cell, the sequence being selected from a cgFAIM sequence shown as SEQ ID NO: 1; a cgFADD sequence shown as SEQ ID NO: 2; a cgPDCD6 sequence shown as SEQ ID NO: 3; and a cgRequiem sequence shown as SEQ ID NO: 4.

There is provided, according to a $2^{nd}$ aspect of the present invention, an isolated polypeptide comprising a sequence selected from the following: (a) a cg FAIM sequence having at least 97% sequence identity with a sequence shown in SEQ ID NO: 1; (b) a cgFADD sequence having at least 69% sequence identity with a sequence shown in SEQ ID NO: 2; (c) a cgPDCD6 sequence having at least 89% sequence identity with a sequence shown in SEQ ID NO: 3; (d) a cgRequiem sequence having at least 90% sequence identity with a sequence shown in SEQ ID NO: 4; (e) a sequence being a fragment of at least 15 contiguous residues of any of (a) to (d) above.

We provide, according to a $3^{rd}$ aspect of the present invention, an isolated polynucleotide comprising a sequence which encodes a polypeptide as set out, in which the sequence is preferably selected from the group consisting of: SEQ ID NO: 5, SEQ ID NO: 6, SEQ ID NO: 7 and SEQ ID NO: 8.

As a $4^{th}$ aspect of the present invention, there is provided an isolated polynucleotide comprising a sequence selected from the following: (a) a cgFAIM sequence which has 90% or more sequence identity to a sequence shown as SEQ ID NO: 5; (b) a cgFADD sequence which has 90% or more sequence identity to a sequence shown as SEQ ID NO: 6; (c) a cgPDCD6 sequence which has 93% or more sequence identity to a sequence shown as SEQ ID NO: 7; (d) a cgRequiem sequence which has 89% or more sequence identity to a sequence shown as SEQ ID NO: 8; (e) a sequence being a fragment of at least 15 contiguous residues of any of (a) to (d) above; or a sequence which is complementary thereto, which is capable of hybridising under stringent conditions thereto, or which is degenerate thereto as a result of the genetic code.

We provide, according to a $5^{th}$ aspect of the present invention, an expression sequence comprising a polynucleotide as set out above or a portion thereof operably linked to a regulatory sequence, the regulatory sequence capable of directing expression of said polynucleotide.

Preferably, such an expression sequence is an expression vector.

The present invention, in a $6^{th}$ aspect, provides a vector comprising a polynucleotide according as set out above, the vector being capable of modulating the expression of cgFAIM, cgFADD, cgPDCD6 or cgRequiem by a cell when exposed to the cell.

Preferably, the vector comprises a *Cricetulus griseus* FAIM sequence or a portion thereof, the vector being capable of effecting up-regulation of cgFAIM in a cell, preferably pcDNA3.1(+) FAIM (SEQ ID NO: 37).

Preferably, the vector comprises a *Cricetulus griseus* FADD sequence or a portion thereof, the vector being capable of effecting down-regulation of cgFADD in a cell, preferably pcDNA3.1(+) FADD DN (SEQ ID NO: 38).

Preferably, the vector comprises a *Cricetulus griseus* PDCD6 sequence or a portion thereof, the vector being capable of effecting down-regulation of cgPDCD6 in a cell, preferably pSUPER.neo.PDCD6 siRNA (SEQ ID NO: 39).

Preferably, the vector comprises a *Cricetulus griseus* Requiem sequence or a portion thereof and capable of effecting down-regulation of cgRequiem in a cell, preferably pSUPER.neo.Requiem siRNA (SEQ ID NO: 40).

In a $7^{th}$ aspect of the present invention, there is provided a cell comprising an expression sequence as described or a vector as described, in which the expression sequence has preferably been transformed into said cell.

According to an $8^{th}$ aspect of the present invention, we provide a pharmaceutical composition comprising a polypeptide as set out, a polynucleotide as set out, an expression sequence as set out, a vector as set out or a cell as set out, together with a pharmaceutically acceptable carrier or diluent.

We provide, according to a $9^{th}$ aspect of the invention, a method of producing a polypeptide comprising: (a) providing an expression sequence comprising a polynucleotide sequence as set out and a regulatory sequence, in which the regulatory sequence is capable of directing expression of the polypeptide from the polynucleotide sequence, (b) allowing expression of the polypeptide from the expression sequence under control of the regulatory sequence, and (c) optionally purifying the polypeptide.

Preferably, the expression sequence comprises an expression vector which is transfected into a cell, preferably a *Cricetulus griseus* cell, to enable expression of the polypeptide by the cell.

There is provided, in accordance with a $10^{th}$ aspect of the present invention, a method comprising modulating, preferably up-regulating, the expression of a cgFAIM polypeptide having a sequence shown as SEQ ID NO: 1 or a cgFAIM polynucleotide having a sequence shown as SEQ ID NO: 5 in a cell, preferably a *Cricetulus griseus* cell.

As an $11^{th}$ aspect of the invention, we provide a method comprising modulating, preferably down-regulating, the expression of a cgFADD polypeptide having a sequence shown as SEQ ID NO: 2, a cgPDCD6 polypeptide having a sequence shown as SEQ ID NO: 3 or a cgRequiem polypeptide having a sequence shown as SEQ ID NO: 4, or a cgFAIM polynucleotide having a sequence shown as SEQ ID NO: 6, a cgPDCD6 polynucleotide having a sequence shown as SEQ ID NO: 7 or a cgRequiem polynucleotide having a sequence shown as SEQ ID NO: 8, in a cell, preferably a *Cricetulus griseus* cell.

Preferably, the method comprises exposing a vector as set out to the cell, preferably transfecting the cell with the vector.

We provide, according to a $12^{th}$ aspect of the invention, a cell, preferably a *Cricetulus griseus* cell, which has been modified, preferably genetically engineered, to up-regulate the expression of a polypeptide having a sequence shown as SEQ ID NO: 1 or a polynucleotide having a sequence shown as SEQ ID NO: 5, compared to a cell which has not been so modified.

According to a $13^{th}$ aspect of the present invention, we provide a cell, preferably a *Cricetulus griseus* cell, which has been modified, preferably genetically engineered, to down-regulate the expression of a polypeptide having a sequence shown as SEQ ID NO: 2, SEQ ID NO: 3 or SEQ ID NO: 4 or a polynucleotide having a sequence shown as SEQ ID NO: 6, SEQ ID NO: 7 or SEQ ID NO: 8, compared to a cell which has not been so modified.

There is provided, according to a $14^{th}$ aspect of the present invention, a cell line comprising a cell as described, or a descendent thereof, preferably a *Cricetulus griseus* cell line.

We provide, according to a $15^{th}$ aspect of the present invention, a cell culture comprising a cell as described, or a descendant thereof, or a cell line as described.

According to a $16^{th}$ aspect of the present invention, we provide a transgenic non-human animal comprising a cell as described, or a descendant thereof, preferably *Cricetulus griseus*.

Preferably, (i) cell viability of the cell is increased or enhanced, preferably in which apoptosis of the cell is reduced; (ii) protein yield, preferably recombinant expressed protein yield, of the cell is increased or enhanced; and/or (iii) glycosylation, preferably sialyation, of expressed protein by the cell is increased or enhanced; compared to a cell in which expression of the polypeptide is not so modulated.

According to a $17^{th}$ aspect of the present invention, we provide use of a method as set out, a cell as set out, a cell line as set out, a cell culture as set out or a transgenic non-human animal as set out, for the production of a protein, preferably a heterologous protein, more preferably from an exogenously introduced sequence, most preferably a recombinant protein.

We provide, according to an $18^{th}$ aspect of the present invention, a method of producing a recombinant protein, the method comprising providing a cell as set out, transfecting the cell with an expression vector capable of expressing the recombinant protein, and causing expression of the recombinant protein in the cell.

According to a $19^{th}$ aspect of the present invention, we provide a polypeptide comprising a cgFADD dominant negative sequence having SEQ ID NO: 9, or a polynucleotide capable of encoding such a polypeptide, preferably SEQ ID NO: 10, or a fragment, homologue, variant or derivative thereof.

As an $20^{th}$ aspect of the invention, we provide a polypeptide, preferably a recombinant protein, more preferably interferon gamma, producable by a method according to the $17^{th}$ or $18^{th}$ aspect of the invention, which polypeptide has an increased sialyation, compared to a polypeptide producable from a cell which is not so modified.

Preferably, the sialyation is greater than 2.9 mol sialic acid/mol of produced polypeptide, preferably about 3.5 mol of sialic acid/mol of produced polypeptide.

Further particular and preferred aspects of the present invention are set out in the accompanying independent and dependent claims. Features of the dependent claims may be combined with features of the independent claims as appropriate, and in combinations other than those explicitly set out in the claims.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T.

Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855, Lars-Inge Larsson "*Immunocytochemistry: Theory and Practice*", CRC Press inc., Baca Raton, Fla., 1988, ISBN 0-8493-6078-1, John D. Pound (ed); "*Immunochemical Protocols, vol 80*", in the series: "Methods in Molecular Biology", Humana Press, Totowa, N.J., 1998, ISBN 0-89603-493-3, Handbook of Drug Screening, edited by Ramakrishna Seethala, Prabhavathi B. Fernandes (2001, New York, N.Y., Marcel Dekker, ISBN 0-8247-0562-9); Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3; and The Merck Manual of Diagnosis and Therapy (17th Edition, Beers, M. H., and Berkow, R, Eds, ISBN: 0911910107, John Wiley & Sons). Each of these general texts is herein incorporated by reference.

BRIEF DESCRIPTION OF THE DRAWINGS

The present invention will be described further, by way of example only, with reference to preferred embodiments thereof as illustrated in the accompanying drawings, in which:

FIG. 2A shows viable cell density (cells/ml) versus time. FIG. 2B shows total cell density versus time. FIG. 2C shows viability versus time. FIG. 2D shows apoptotic cells versus time. Loss of cell culture viability is significantly reduced with FAIM over-expression compared to control cells (FIG. 2C) due to significant reduction in apoptotic cells (FIG. 2D).

FIG. 3A shows viable cell density (cells/ml) versus time. FIG. 3B shows total cell density versus time. FIG. 3C shows viability versus time. FIG. 3D shows apoptotic cells versus time. Loss of cell culture viability is significantly reduced with FADD Dominant Negative over-expression compared to control cells (FIG. 3C) due to significant reduction in apoptotic cells (FIG. 3D).

FIG. 4A shows viable cell density (cells/ml) versus time, FIG. 4B shows total cell density versus time, FIG. 4C shows viability versus time, FIG. 4D shows apoptotic cells versus time. Loss of cell culture viability is significantly reduced when PDCD6 is suppressed compared to control cells (FIG. 4C) due to significant reduction in apoptotic cells (FIG. 4D).

FIG. 5A shows viable cell density (cells/ml) versus time. FIG. 5B shows total cell density versus time. FIG. 5C shows viability versus time. FIG. 5D shows apoptotic cells versus time. Loss of cell culture viability is significantly reduced when Requiem is suppressed compared to control cells (FIG. 5C) due to significant reduction in apoptotic cells (FIG. 5D).

FIG. 6A shows caspase activity in cells transfected with a control. FIG. 6B shows caspase activity in cells over-expressing FAIM. FIG. 6C shows caspase activity in cells over-expressing FADD Dominant Negative. FIG. 6D shows caspase activity in cells with suppression of PDCD6. FIG. 6E shows caspase activity in cells with suppression of Requiem. Gene targeting FAIM, FADD Dominant Negative, PDCD6 or REQUIEM is able to either suppress and/or delay caspases activity in culture.

FIG. 7A shows interferon-γ activity in cells over-expressing FAIM. FIG. 7B shows interferon-γ activity in cells over-expressing FADD Dominant Negative. FIG. 7C shows interferon-γ activity in cells with suppression of PDCD6. FIG. 7D shows interferon-γ activity in cells with suppression of REQUIEM. Significant improvement of interferon gamma yields by up to 300% can be achieved through gene targeting approach.

DESCRIPTION OF SEQUENCES

Figure 1:
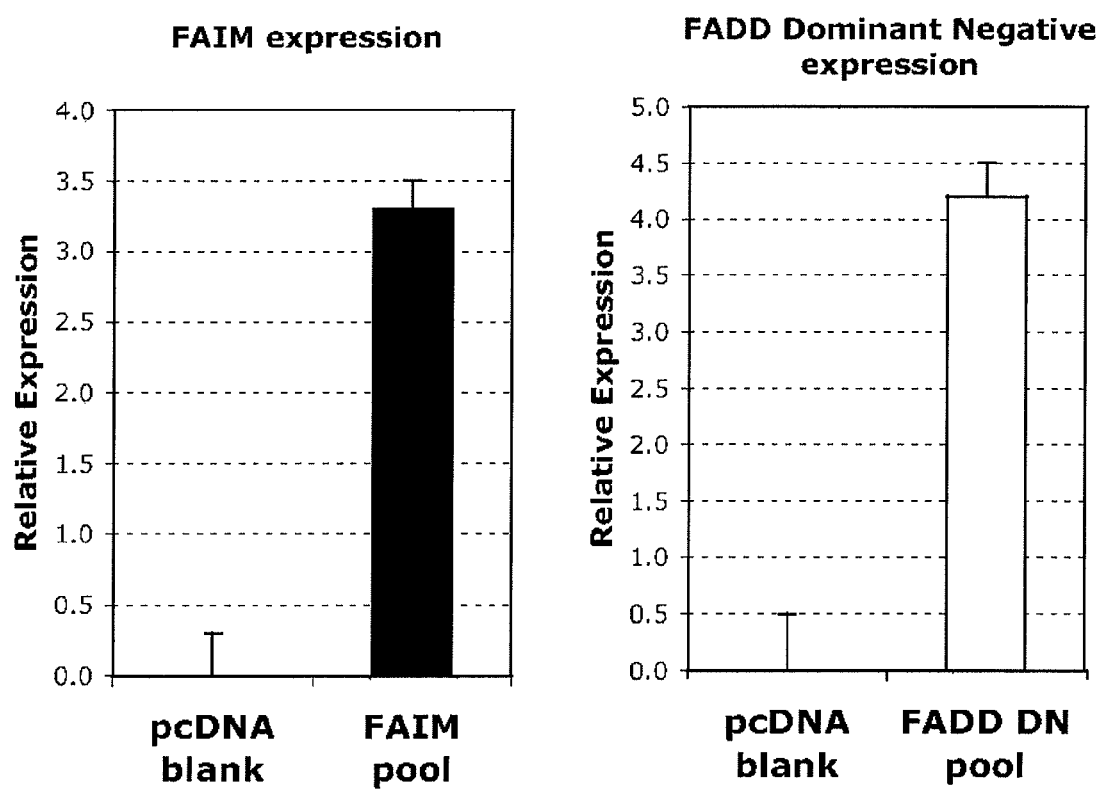
FIGS. 1A-1D are graphs showing over-expression of FADD Dominant Negative (FIG. 1B) and FAIM (FIG. 1A) and suppression of Requiem (FIG. 1D) and PDCD6 (FIG. 1C) expression, in cells transfected with relevant constructs.
Figure 1:
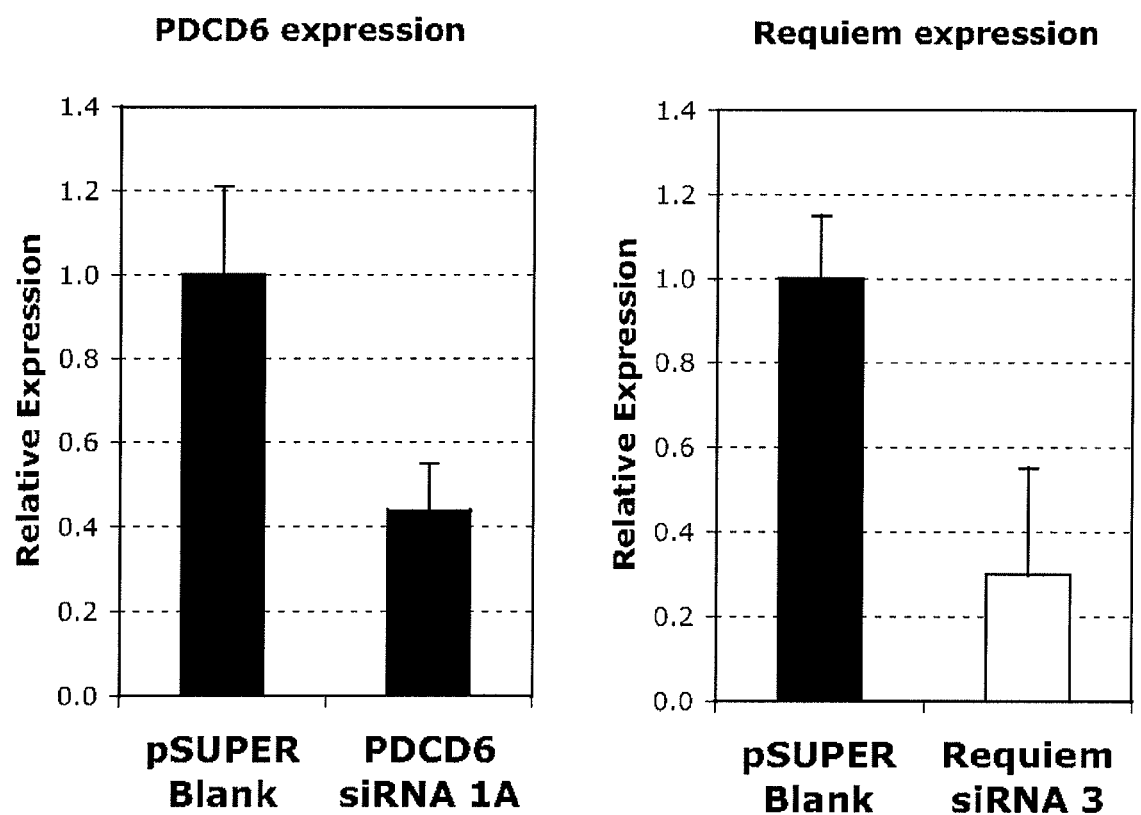

SEQ ID NO: 1 is the sequence of amino acid sequence of *C. griseus* FAIM. SEQ ID NO: 2 is the amino acid sequence of *C. griseus* FADD. SEQ ID NO: 3 is the amino acid sequence of *C. griseus* PDCD6. SEQ ID NO: 4 is the amino acid sequence of *C. griseus* Requiem.

SEQ ID NO: 5 is the nucleic acid sequence of *C. griseus* FAIM. SEQ ID NO: 6 is the nucleic acid sequence of *C. griseus* FADD. SEQ ID NO: 7 is the nucleic acid sequence of *C. griseus* PDCD6. SEQ ID NO: 8 is the nucleic acid sequence of *C. griseus* Requiem.

SEQ ID NO: 9 is the amino acid sequence of *C. griseus* FADD dominant negative. SEQ ID NO: 10 is the nucleic acid sequence of *C. griseus* FADD dominant negative. SEQ ID NO: 11 is the sequence of *C. griseus* FADD dominant negative 5'-PCR primer. SEQ ID NO: 12 is the sequence of *C.*

*griseus* FADD dominant negative 3'-PCR primer. SEQ ID NO: 13 is the sequence of *C. griseus* PDCD6 suppression vector insert 5'. SEQ ID NO: 14 is the sequence of *C. griseus* PDCD6 suppression vector insert 3'. SEQ ID NO: 15 is the sequence of *C. griseus* Requiem suppression vector insert 5'. SEQ ID NO: 16 is the sequence of *C. griseus* Requiem suppression vector insert 3'.

SEQ ID NO: 17 is the sequence of *C. griseus* FAIM 5' PCR primer. SEQ ID NO: 18 is the sequence of *C. griseus* FAIM 3' PCR primer. SEQ ID NO: 19 is the sequence of *C. griseus* FADD 5' PCR primer. SEQ ID NO: 20 is the sequence of *C. griseus* FADD 3' PCR primer. SEQ ID NO: 21 is the sequence of *C. griseus* PDCD6 5' PCR primer. SEQ ID NO: 22 is the sequence of *C. griseus* PDCD6 3' PCR primer. SEQ ID NO: 23 is the sequence of *C. griseus* PDCD6 3'-RACE primer. SEQ ID NO: 24 is the sequence of *C. griseus* Requiem 5' PCR primer. SEQ ID NO: 25 is the sequence of *C. griseus* Requiem 3' PCR primer. SEQ ID NO: 26 is the sequence of *C. griseus* Requiem 3'-RACE primer.

SEQ ID NO: 27 is the sequence of *C. griseus* FAIM Quantitative Real Time PCR primer 5'. SEQ ID NO: 28 is the sequence of *C. griseus* FAIM Quantitative Real Time PCR primer 3'. SEQ ID NO: 29 is the sequence of *C. griseus* FADD Quantitative Real Time PCR primer 5'. SEQ ID NO: 30 is the sequence of *C. griseus* FADD Quantitative Real Time PCR primer 3'. SEQ ID NO: 31 is the sequence of *C. griseus* PDCD6 Quantitative Real Time PCR primer 5'. SEQ ID NO: 32 is the sequence of *C. griseus* PDCD6 Quantitative Real Time PCR primer 3'. SEQ ID NO: 33 is the sequence of *C. griseus* Requiem Quantitative Real Time PCR primer 5'. SEQ ID NO: 34 is the sequence of *C. griseus* Requiem Quantitative Real Time PCR primer 3'. SEQ ID NO: 35 is the sequence of β-actin Quantitative Real Time PCR primer 5'.

SEQ ID NO: 36 is the sequence of a β-actin Quantitative Real Time PCR primer 3'. SEQ ID NO: 37 is the nucleic acid sequence of plasmid pcDNA3.1(+) FAIM. SEQ ID NO: 38 is the nucleic acid sequence of plasmid pcDNA3.1(+) FADD DN. SEQ ID NO: 39 is the nucleic acid sequence of plasmid pSUPER.neo.PDCD6 siRNA. SEQ ID NO: 40 is the nucleic acid sequence of plasmid pSUPER.neo.Requeim siRNA.

The methods and compositions described here may suitably employ any one or more of the sequences shown in the Sequence Listing.

DETAILED DESCRIPTION

Chinese Hamster Sequences

The disclosure provides generally for certain nucleic acids, polypeptides, as well as fragments, homologues, variants and derivatives thereof from the Chinese hamster, *Cricetulus griseus*, which are capable of modulating apoptosis in cells.

In particular, we provide for *Cricetulus griseus* FADD, FAIM, PDCD6 and Requiem polypeptide and nucleic acid sequences as set out in the Sequence Listings. In addition we provide for the use of such genes, fragments, homologues.

Particularly preferred uses include the modification of cells, particularly Chinese Hamster Ovary cells, for enhanced properties, such as increased viability, increased capacity to express proteins (particularly recombinant proteins) and increased glycosylation, preferably sialyation, of such proteins. Such modified cells and derivatives of these (such as colonies, clones, cell lines, etc) are described in further detail below, and may be used as apoptosis resistant cells for the production of recombinant proteins.

cgFAIM, cgFADD, cgPDCD6 and cgRequiem Polypeptides

It will be understood that polypeptide sequences disclosed here are not limited to the particular sequences set forth in the sequence listing, or fragments thereof, or sequences obtained from cgFAIM, cgFADD, cgPDCD6 and/or cgRequiem protein, but also include homologous sequences obtained from any source, for example related cellular homologues, homologues from other species and variants or derivatives thereof, provided that they have at least one of the biological activities of cgFAIM, cgFADD, cgPDCD6 and/or cgRequiem, as the case may be.

This disclosure therefore encompasses variants, homologues or derivatives of the amino acid sequences set forth in the sequence listings, as well as variants, homologues or derivatives of the amino acid sequences encoded by the nucleotide sequences disclosed here. Such sequences are generally referred to as a "cgFADD sequence", a "cgFAIM sequence", "a cgPDCD6 sequence", or a "cgRequiem sequence", as the case may be.

Biological Activities

In highly preferred embodiments, the sequences comprise at least one biological activity of cgFAIM, cgFADD, cgPDCD6 and/or cgRequiem, as the case may be.

Preferably, in the case of cgFAIM, the biological activity comprises apoptosis inhibiting activity, preferably assayed by down-regulation of caspase activity. Thus, the cgFADD sequences described in this document preferably are capable of inhibiting apoptosis, specifically capable of down-regulating caspase activity in the context of a cell.

In highly preferred embodiments, when assayed using such methods, the cgFAIM sequences when transfected into a cell are capable of inhibiting apoptosis by at least 10%, preferably 20%, more preferably 30%, 40% 50%, 60%, 70%, 80%, 90% or more, compared to a cell which has not been so transfected with the relevant cgFAIM sequence.

In the case of cgFADD, cgPDCD6 and cgRequiem, the biological activity preferably comprises apoptosis stimulating activity, preferably assayed by up-regulation of caspase activity. Thus, the cgFADD, cgPDCD6 and cgRequiem sequences described in this document preferably are capable of up-stimulating apoptosis, specifically capable of up-regulating caspase activity in the context of a cell.

In highly preferred embodiments, when assayed using such methods, the cgFADD, cgPDCD6 and cgRequiem sequences when transfected into a cell are capable of stimulating apoptosis by at least 10%, preferably 20%, more preferably 30%, 40% 50%, 60%, 70%, 80%, 90% or more, compared to a cell which has not been so transfected with the relevant cgFADD, cgPDCD6 or cgRequiem sequence.

In highly preferred embodiments, the activation or repression of apoptosis by the cgFAIM, cgFADD, cgPDCD6 and/or cgRequiem sequences is assayed by assaying caspase activity. Thus, the percentage stimulation or repression of apoptosis set out above are in highly preferred embodiments to be read as percentage stimulation or repression of caspase activity.

Thus, apoptosis activity monitoring methods such as caspase activity measurement assays using colorimetric or fluorometric methods can be used to ascertain the biochemical activity of cgFAIM, cgFADD, cgPDCD6 and/or cgRequiem. Such methods may be carried out in cells transfected with appropriate expression constructs, such as by means known in the art, or using protocols set out in the Examples, to determine whether apoptosis is affected and/or caspase activity is up- or down-regulated.

Caspases are a large family of cysteine proteases that mediates apoptosis (Nicholson & Thornberry 1997; Thornberry & Littlewood 1998). Caspase-8 is an initiator caspase that act the most upstream in receptor-mediated apoptotic pathway. Upon activation of cell-surface receptors, caspase-8 directly or indirectly initiates the proteolytic activities of downstream effector caspases such as caspase-3 (Srinivasula et al 1996 and Cohen 1997). Caspase-9, which is also another upstream caspase, is activated via the mitochondrial release of cytochrome c to the cytosol. Released cytochrome c binds to the apoptotic protease activating factor, APAF-1, forming a complex that activates procaspase-9 (Zou et al 1999 and Hu et al 1999). Active caspase-9 initiates a protease cascade that also activates caspase-3 and other downstream caspases.

In preferred embodiments, the caspase activity that is assayed to determine up- or down-regulation of apoptosis activity comprises caspase-8 or caspase-9.

Methods for assaying caspase-8 and caspase-9 activity are known in the art, and are specifically described in, for example, Nicholson D W and Thornberry N A (1997) Caspases: killer proteases. *Trends Biochem Sci.* 272: 2952-2956 and Thornberry N A and Littlewood Y (1998) Caspases: Enemies within. *Science* 281:1312-1316. Any of the protocols set out in the prior art may be used to assay caspase activity.

In preferred embodiments, however, the "Caspase Assay Protocol" set out below is employed to assay caspase-8 and/or caspase-9 activity.

Caspase Assay Protocol

Caspase activity can be assayed by utilizing fluorogenic substrates specific for different caspases immobilized in the wells. Application of cell lysates containing the active caspase to the wells will cleave the substrate and release a fluorescent product that can be detected using standard fluorescence plate reader.

Specifically, BD ApoAlert™ Caspase assay plates (catalogue number K2033-1, BD Biosciences Clontech, Palo Alto, Calif., USA) uses different caspase substrates composed of short peptides that are recognized by their respective activated caspases. The peptides are covalently linked to the fluorogenic dye 7-amino-4-methyl coumarin (AMC). Peptide bound AMC emits in the UV range. ($\lambda_{max}$=380 nm) while unbound AMC emits in the green range ($\lambda_{max}$=460 nm). This makes it possible to correlate an increase in fluorescence intensity at 460 nm with an increase in activity of the respective caspase in the test sample. For assaying caspase-8 activity, the substrate used is VDVAD-AMC while an assay for caspase-9 activity uses LEHD-AMC as its substrate.

In order to assay for caspases activity using BD ApoAlert™ Caspase assay plate, cells from samples are pelleted by centrifugation and then resuspended in 1× cell lysis buffer (BD Biosciences Clontech) and incubated on ice for 10 min. Cellular debris is then removed by centrifugation for 5 min at 4° C. 50 µL of 2× reaction buffer/DTT mix is then added to each well of the 96-well plate that will be used. The plate is preincubated at 37° C. for 5 min. 50 µL of the appropriate cell lysate(s) is then added to the wells and incubated at 37° C. for 2 hour. A fluorescence plate reader is then used to measure the amount of AMC released (Excitation at 380 nm, Emission at 460 nm).

Caspase activity is defined as the absolute emission at 460 nm of a sample after subtraction from the absolute emission at 460 nm of a reference sample. The reference sample is a sample collected at time reference zero.

Caspase activity of cells transfected with cgFAIM, cgFADD, cgPDCD6 and/or cgRequiem expression vectors may be compared with cells transfected with null-vectors (or untransfected) to determine the percentage by which apoptosis is stimulated or repressed as the case may be.

[End of "Caspase Assay Protocol"]

In preferred embodiments, when assayed using such methods, the cgFAIM sequences when transfected into a cell are capable of inhibiting the expression of caspase-8, or caspase-9, or both by at least 10%, preferably 20%, more preferably 30%, 40% 50%, 60%, 70%, 80%, 90% or more, compared to a cell which has not been so transfected with the relevant cgFAIM sequence.

In highly preferred embodiments, when assayed using such methods, the cgFADD, cgPDCD6 and cgRequiem sequences when transfected into a cell are capable of stimulating the expression of caspase-8, or caspase-9, or both by at least 10%, preferably 20%, more preferably 30%, 40% 50%, 60%, 70%, 80%, 90% or more, compared to a cell which has not been so transfected with the relevant cgFADD, cgPDCD6 or cgRequiem sequence.

Other assays that detect apoptosis related events such as membrane changes, DNA fragmentation and other biochemical hallmarks of apoptosis can also be used, instead of, or in addition to, the assays described.

Homologues

The polypeptides disclosed include homologous sequences obtained from any source, for example related viral/bacterial proteins, cellular homologues and synthetic peptides, as well as variants or derivatives thereof. Thus polypeptides also include those encoding homologues of cgFAIM, cgFADD, cgPDCD6 and/or cgRequiem from other species including animals such as mammals (e.g. mice, rats or rabbits), in particular rodents.

In the context of the present document, a homologous sequence or homologue is taken to include an amino acid sequence which is at least 60, 65, 70, 75, 80, 85, 86, 87, 88, 89 or 90% identical, preferably at least 91, 92, 93, 94, 95, 96, 97, 98 or 99% identical at the amino acid level over at least 30, preferably 40, 50, 60, 70, 80, 90 or 100 amino acids with cgFAIM, cgFADD, cgPDCD6 and/or cgRequiem, as the case may be, for example as shown in the sequence listing herein. In the context of this document, a homologous sequence is taken to include an amino acid sequence which is at least 15, 20, 25, 30, 40, 50, 60, 65, 70, 75, 80, 85, 86, 97, 88, 89 or 90% identical, preferably at least 91, 92, 93, 94, 95, 96, 97, 98 or 99% identical at the amino acid level, preferably over at least 15, 25, 35, 50 or 100, preferably 200, 300, 400 or 500 amino acids with the sequence of cgFAIM, cgFADD, cgPDCD6 and/or cgRequiem. For example, a sequence may have the stated sequence identity to cgFADD (preferably comprising a sequence as shown in SEQ ID NO: 1), cgFAIM (preferably comprising a sequence as shown in SEQ ID NO: 2), cgPDCD6 (preferably comprising a sequence as shown in SEQ ID NO: 3) or cgRequiem (preferably comprising a sequence as shown in SEQ ID NO: 4).

Although homology can also be considered in terms of similarity (i.e. amino acid residues having similar chemical properties/functions), in the context of the present document it is preferred to express homology in terms of sequence identity. In highly preferred embodiments, the sequence identity is determined relative to the entirety of the length of the relevant sequence, i.e., over the entire length or full length sequence of the relevant gene, for example.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalizing unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

In preferred embodiments, sequence similarity, identity, homology or complementarity is adjudged with respect to the entire length of the relevant sequence used for comparison.

Variants and Derivatives

The terms "variant" or "derivative" in relation to the amino acid sequences as described here includes any substitution of, variation of, modification of, replacement of, deletion of or addition of one (or more) amino acids from or to the sequence. Preferably, the resultant amino acid sequence retains substantially the same activity as the unmodified sequence, preferably having at least the same activity as the cgFAIM, cgFADD, cgPDCD6 and cgRequiem polypeptides shown in the sequence listings. Thus, the key feature of the sequences—namely that they are capable of modulating one or more apoptotic processes—is preferably retained.

Polypeptides having the amino acid sequence shown in the Examples, or fragments or homologues thereof may be modified for use in the methods and compositions described here. Typically, modifications are made that maintain the biological activity of the sequence. Amino acid substitutions may be made, for example from 1, 2 or 3 to 10, 20 or 30 substitutions provided that the modified sequence retains the biological activity of the unmodified sequence. Amino acid substitutions may include the use of non-naturally occurring analogues, for example to increase blood plasma half-life of a therapeutically administered polypeptide.

Natural variants of cgFAIM, cgFADD, cgPDCD6 and cgRequiem are likely to comprise conservative amino acid substitutions. Conservative substitutions may be defined, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Fragments

Polypeptides disclosed here and useful as markers also include fragments of the above mentioned full length polypeptides and variants thereof, including fragments of the sequences set out in the sequence listings.

Polypeptides also include fragments of the full length sequence of any of the cgFAIM, cgFADD, cgPDCD6 and cgRequiem polypeptides. Preferably fragments comprise at least one epitope. Methods of identifying epitopes are well known in the art. Fragments will typically comprise at least 6 amino acids, more preferably at least 10, 20, 30, 50 or 100 amino acids.

Included are fragments comprising, preferably consisting of, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145 or 150, or more residues from a cgFAIM, cgFADD, cgPDCD6 and/or cgRequiem amino acid sequence.

Polypeptide fragments of the cgFAIM, cgFADD, cgPDCD6 and cgRequiem proteins and allelic and species variants thereof may contain one or more (e.g. 5, 10, 15, or 20) substitutions, deletions or insertions, including conserved substitutions. Where substitutions, deletion and/or insertions occur, for example in different species, preferably less than 50%, 40% or 20% of the amino acid residues depicted in the sequence listings are altered.

cgFAIM, cgFADD, cgPDCD6 and cgRequiem, and their fragments, homologues, variants and derivatives, may be made by recombinant means. However, they may also be made by synthetic means using techniques well known to skilled persons such as solid phase synthesis. The proteins may also be produced as fusion proteins, for example to aid in extraction and purification. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the function of the protein of interest sequence. Proteins may also be obtained by purification of cell extracts from animal cells.

The cgFAIM, cgFADD, cgPDCD6 and cgRequiem polypeptides, variants, homologues, fragments and derivatives disclosed here may be in a substantially isolated form. It will be understood that such polypeptides may be mixed with carriers or diluents which will not interfere with the intended purpose of the protein and still be regarded as substantially isolated. A cgFAIM, cgFADD, cgPDCD6 and/or cgRequiem variant, homologue, fragment or derivative may also be in a substantially purified form, in which case it will generally comprise the protein in a preparation in which more than 90%, e.g. 95%, 98% or 99% of the protein in the preparation is a protein.

The cgFAIM, cgFADD, cgPDCD6 and cgRequiem polypeptides, variants, homologues, fragments and derivatives disclosed here may be labelled with a revealing label. The revealing label may be any suitable label which allows the polypeptide, etc to be detected. Suitable labels include radioisotopes, e.g. $^{125}$I, enzymes, antibodies, polynucleotides and linkers such as biotin. Labelled polypeptides may be used in diagnostic procedures such as immunoassays to determine the amount of a polypeptide in a sample. Polypeptides or labelled polypeptides may also be used in serological or cell-mediated immune assays for the detection of immune reactivity to said polypeptides in animals and humans using standard protocols.

cgFAIM, cgFADD, cgPDCD6 and cgRequiem polypeptides, variants, homologues, fragments and derivatives disclosed here, optionally labelled, my also be fixed to a solid phase, for example the surface of an immunoassay well or dipstick. Such labelled and/or immobilised polypeptides may be packaged into kits in a suitable container along with suitable reagents, controls, instructions and the like. Such polypeptides and kits may be used in methods of detection of antibodies to the polypeptides or their allelic or species variants by immunoassay.

Immunoassay methods are well known in the art and will generally comprise: (a) providing a polypeptide comprising an epitope bindable by an antibody against said protein; (b) incubating a biological sample with said polypeptide under conditions which allow for the formation of an antibody-antigen complex; and (c) determining whether antibody-antigen complex comprising said polypeptide is formed.

The cgFAIM, cgFADD, cgPDCD6 and cgRequiem polypeptides, variants, homologues, fragments and derivatives disclosed here may be used in in vitro or in vivo cell culture systems to study the role of their corresponding genes and homologues thereof in cell function, including their function in disease. For example, truncated or modified polypeptides may be introduced into a cell to disrupt the normal functions which occur in the cell. The polypeptides may be introduced into the cell by in situ expression of the polypeptide from a recombinant expression vector (see below). The expression vector optionally carries an inducible promoter to control the expression of the polypeptide.

The use of appropriate host cells, such as insect cells or mammalian cells, is expected to provide for such post-translational modifications (e.g. myristolation, glycosylation, truncation, lipidation and tyrosine, serine or threonine phosphorylation) as may be needed to confer optimal biological activity on recombinant expression products. Such cell culture systems in which the cgFAIM, cgFADD, cgPDCD6 and cgRequiem polypeptides, variants, homologues, fragments and derivatives disclosed here are expressed may be used in assay systems to identify candidate substances which interfere with or enhance the functions of the polypeptides in the cell.

cgFAIM, cgFADD, cgPDCD6 and cgRequiem Nucleic Acids

We provide generally for a number of cgFAIM, cgFADD, cgPDCD6 and cgRequiem nucleic acids, together with fragments, homologues, variants and derivatives thereof. These nucleic acid sequences preferably encode the polypeptide sequences disclosed here, and particularly in the sequence listings.

Preferably, the polynucleotides comprise cgFAIM, cgFADD, cgPDCD6 and cgRequiem nucleic acids, preferably selected from the group consisting of: SEQ ID NO: 5, SEQ ID NO: 6, SEQ ID NO: 7 and SEQ ID NO: 8 respectively.

In particular, we provide for nucleic acids or polynucleotides which encode any of the *Cricetulus griseus* polypeptides disclosed here. Thus, the terms "cgFADD sequence", "cgFAIM sequence", "cgPDCD6 sequence" and "cgRequiem sequence" should be construed accordingly. Preferably, however, such nucleic acids or polynucleotides comprise any of the sequences set out as SEQ ID NOs: 5 to 16 and SEQ ID Nos: 37, 38, 39 and 40, or a sequence encoding any of the corresponding polypeptides, and a fragment, homologue, variant or derivative of such a nucleic acid. The above terms therefore preferably should be taken to refer to these sequences.

As used here in this document, the terms "polynucleotide", "nucleotide", and nucleic acid are intended to be synonymous with each other. "Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Variants, Derivatives and Homologues

The polynucleotides described here may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present document, it is to be understood that the polynucleotides described herein may be modified by any method available in the art. Such modifications may be carried out in order to enhance the in vivo activity or life span of polynucleotides.

Where the polynucleotide is double-stranded, both strands of the duplex, either individually or in combination, are encompassed by the methods and compositions described here. Where the polynucleotide is single-stranded, it is to be understood that the complementary sequence of that polynucleotide is also included.

The terms "variant", "homologue" or "derivative" in relation to a nucleotide sequence include any substitution of, variation of, modification of, replacement of, deletion of or addition of one (or more) nucleotides from or to the sequence. Preferably, the resulting sequence is capable of encoding a polypeptide which has apoptosis mediator activity.

As indicated above, with respect to sequence identity, a "homologue" has preferably at least 5% identity, at least 10% identity, at least 15% identity, at least 20% identity, at least 25% identity, at least 30% identity, at least 35% identity, at least 40% identity, at least 45% identity, at least 50% identity, at least 55% identity, at least 60% identity, at least 65% identity, at least 70% identity, at least 75% identity, at least 80% identity, at least 85% identity, at least 90% identity, or at least 95% identity to the relevant sequence shown in the sequence listings.

More preferably there is at least 95% identity, more preferably at least 96% identity, more preferably at least 97% identity, more preferably at least 98% identity, more preferably at least 99% identity. Nucleotide homology comparisons may be conducted as described above. A preferred sequence comparison program is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

In preferred embodiments, a cgFAIM polynucleotide has at least 90% or more sequence identity to a sequence shown as SEQ ID NO: 5. Preferably, the cgFAIM polynucleotide has 91% or more, preferably 92% or more, 93% or more, 94% or more, 95% or more, 96% or more, 97% or more, 98% or more, 99% or more or 99.5% or more sequence identity to a sequence shown as SEQ ID NO: 5.

Similarly, in preferred embodiments, a cgFADD sequence has at least 90% sequence identity to a sequence shown as SEQ ID NO: 6. Preferably, the cgFADD polynucleotide has 91% or more, preferably 92% or more, 93% or more, 94% or more, 95% or more, 96% or more, 97% or more, 98% or more, 99% or more or 99.5% or more sequence identity to a sequence shown as SEQ ID NO: 6.

In preferred embodiments, a cgPDCD6 sequence has at least 93% or more sequence identity to a sequence shown as SEQ ID NO: 7. ably, the cgPDCD6 polynucleotide has 94% or more, 95% or more, 96% or more, 97% or more, 98% or more, 99% or more or 99.5% or more sequence identity to a sequence shown as SEQ ID NO: 7.

In preferred embodiments, a cgRequiem polynucleotide has at least 90% or more sequence identity to a sequence shown as SEQ ID NO: 5. Preferably, the cgRequiem polynucleotide has 90% or more, preferably 91% or more, 92% or more, 93% or more, 94% or more, 95% or more, 96% or more, 97% or more, 98% or more, 99% or more or 99.5% or more sequence identity to a sequence shown as SEQ ID NO: 8

Hybridisation

We further describe cgFAIM, cgFADD, cgPDCD6 and cgRequiem nucleotide sequences that are capable of hybridising selectively to any of the sequences presented herein, or any variant, fragment or derivative thereof, or to the complement of any of the above. Nucleotide sequences are preferably at least 15 nucleotides in length, more preferably at least 20, 30, 40 or 50 nucleotides in length.

The term "hybridisation" as used herein shall include "the process by which a strand of nucleic acid joins with a complementary strand through base pairing" as well as the process of amplification as carried out in polymerase chain reaction technologies.

Polynucleotides capable of selectively hybridising to the nucleotide sequences presented herein, or to their complement, will be generally at least 70%, preferably at least 80 or 90% and more preferably at least 95% or 98% homologous to the corresponding nucleotide sequences presented herein over a region of at least 20, preferably at least 25 or 30, for instance at least 40, 60 or 100 or more contiguous nucleotides.

The term "selectively hybridizable" means that the polynucleotide used as a probe is used under conditions where a target polynucleotide is found to hybridize to the probe at a level significantly above background. The background hybridization may occur because of other polynucleotides present, for example, in the cDNA or genomic DNA library being screened. In this event, background implies a level of signal generated by interaction between the probe and a non-specific DNA member of the library which is less than 10 fold, preferably less than 100 fold as intense as the specific interaction observed with the target DNA. The intensity of interaction may be measured, for example, by radiolabelling the probe, e.g. with $^{32}P$.

Hybridisation conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical polynucleotide sequences while an intermediate (or low) stringency hybridisation can be used to identify or detect similar or related polynucleotide sequences.

In a preferred aspect, we disclose nucleotide sequences that can hybridise to a cgFAIM, cgFADD, cgPDCD6 and/or cgRequiem nucleic acid, or a fragment, homologue, variant or derivative thereof, under stringent conditions (e.g. 65° C. and 0.1×SSC {1×SSC=0.15 M NaCl, 0.015 M Na$_3$ Citrate pH 7.0}).

Where a polynucleotide is double-stranded, both strands of the duplex, either individually or in combination, are encompassed by the present disclosure. Where the polynucleotide is single-stranded, it is to be understood that the complementary sequence of that polynucleotide is also disclosed and encompassed.

Polynucleotides which are not 100% homologous to the sequences disclosed here but fall within the disclosure can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of SEQ ID NO: 1 to 40 under conditions of medium to high stringency. Similar considerations apply to obtaining species homologues and allelic variants of cgFAIM, cgFADD, cgPDCD6 and cgRequiem.

The polynucleotides described here may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides as used herein. Preferred fragments are less than 500, 200, 100, 50 or 20 nucleotides in length.

Polynucleotides such as a DNA polynucleotides and probes may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 15 to 30 nucleotides) flanking a region of the sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector Uses of CG Sequences As shown in the Examples, we have established that these four genes are involved in the mediation of apoptosis in the cell.

We also show that targeting of such genes by modulation of their activity results in reduction of apoptosis and hence improved cell viability. The genes and polypeptides and products thereof therefore have utility in a number of fields, for example in cell culture.

Thus, U.S. Pat. No. 6,586,206 describes the use of apoptosis inhibitors in the production of recombinant proteins using cultured host cells, with the effect of improved yield of the desired protein. Accordingly, the disclosure of the sequences of *Cricetulus griseus* FAIM, FADD, PDCD6 and Requiem therefore enables the targeting of these genes in cell culture to enhance cell viability and promote enhanced yields of recombinant protein production. Specifically, cgFAIM, cgFADD, cgPDCD6 and cgRequiem modified cells we describe here, preferably *Cricetulus griseus* cells, more preferably Chinese Hamster Ovary cells, may be suitably employed for production of recombinant proteins with improved yield.

cgFAIM, cgFADD, cgPDCD6 and cgRequiem Modified Cells

According to the methods and compositions described here, modulation of any one or more of cgFAIM, cgFADD, cgPDCD6 and cgRequiem in a cell improves cell viability of a population, preferably a *Cricetulus griseus* population. In particular, we show in the Examples that reduction of expression of cgFADD, cgPDCD6 and/or cgRequiem, as well as increasing expression of cgFAIM, leads to improved cell viability.

However, it will be appreciated that methods of regulation of any of these genes, including use of modulator entities such as agonists and antagonists, may be employed in addition to, or as an alternative to, modulation of polypeptide expression.

Cells in which the expression of any one or more of these genes are modulated are referred to for convenience as "modified" cells—although it will be appreciated that these may not be physically modified themselves, but may be descendants of cells which have been modified. We specifically provide for cells in which cgFAIM expression is up-regulated, as well as for cells in which expression of cgFADD, cgPDCD6 and/or cgRequiem, or any combination thereof is down-regulated. Thus, it will be appreciated that expression of one, two, three, or all four of cgFAIM, cgFADD, cgPDCD6 and cgRequiem may be modulated in the modified cells. The modification may be transient, or it may be permanent or long term, depending on the mode of modification.

The modified cells may comprise mammalian cells, preferably *Cricetulus griseus* cells, most preferably CHO cells. They may comprise rodent cells, preferably mouse or rat cells. Preferably, such modified cells comprise *Cricetulus griseus* cells, most preferably CHO cells. However, they may comprise primate cells, such as monkey cells or human cells.

The relevant cells may be modified by targeting relevant genes by any means known in the art.

One possible approach is to express anti-sense constructs directed against cgFADD, cgPDCD6 and/or cgRequiem, to inhibit gene function and prevent the expression of the relevant polypeptide. Another approach is to use non-functional variants of cgFADD, cgPDCD6 and/or cgRequiem polypeptides that compete with the endogenous gene product for cellular components of cell death machinery, resulting in inhibition of function. Alternatively, compounds identified by the assays described above as binding to a cgFADD, cgP- DCD6 and/or cgRequiem polypeptide may be administered to cells to prevent the function of that polypeptide. This may be performed, for example, by means of recombinant DNA technology or by direct administration of the compounds. Suitable antibodies directed against cgFADD, cgPDCD6 and/or cgRequiem may also be used as agents.

Alternatively, double-stranded (ds) RNA is a powerful way of interfering with gene expression in a range of organisms that has recently been shown to be successful in mammals (Wianny and Zernicka-Goetz, 2000, Nat Cell Biol 2000, 2, 70-75). Double stranded RNA corresponding to the sequence of a cgFADD, cgPDCD6 and/or cgRequiem polynucleotide can be introduced into or expressed in cells or cell lines to enhance cell viability.

In particular, we describe modification by the use of single interfering RNAs (siRNAs) as well as the use of dominant negative mutants where reduction in expression is desired. We further describe the use of vectors which enable overexpression of a relevant sequence for increasing expression of relevant genes. The modification may be transient, or it may be permanent. Thus, we provide for cell lines which comprise cells with genomic and transmittable modifications in cgFAIM, cgFADD, cgPDCD6 and/or cgRequiem. A detailed protocol for establishing such cells lines is set out in the Examples.

The modified cells may be provided as single cells, groups of cells, clones, clonal lines, colonies, cell lines or tissues. We further provide for transgenic animals whose cells comprise down-regulated expression of cgFADD, cgPDCD6 and/or cgRequiem, or up-regulated expression of cgFADD, or both.

Preferably, the dominant mutant comprises a cgFADD dominant mutant comprising the sequence set out in SEQ ID NO: 9. Alternatively, or in addition, the sequence may comprise:

(SEQ ID NO: 41)
FDIVCDNVGRDWKRLARQLKVSEAKIDGIEERYPRSLSEQVREALRVWKI

AEREKATVAGLVKALRACRLNLVADLVE

The dominant mutant may be encoded by a sequence set out in SEQ ID NO: 10, or alternatively, (SEQ ID NO: 42)
TTTGACATTGTATGCGACAATGTGGGGAGAGATTGGAAGAGACTGGCCCG

CCAGCTGAAAGTGTCTGAGGCCAAAATTGATGGGATTGAGGAGAGGTACC

CCCGAAGCCTGAGTGAGCAGGTAAGGGAGGCTCTGAGAGTCTGGAAGATT

GCCGAGAGGGAGAAAGCCACGGTGGCTGGACTGGTAAAGGCACTTCGGGC

CTGCCGGCTGAACCTGGTGGCTGACCTGGTGGAA

Increased Cell Viability

The modified cells have several beneficial properties when compared to cognate non-modified cells, or wild type cells, or parental cells from which they are derived. They may have the property of having improved cell viability. Thus, they may survive in culture longer, in terms of time or number of generations.

Preferably, cell viability is gauged by quantitating a viable cell density of a population of cells which have been modified, i.e., by targeting cgFAIM, cgFADD, cgPDCD6 and cgRequiem. Preferably, the modified cells maintain a higher cell viability, compared to cells which have not been modified (e.g., a control population). Cell viability is preferably measured as the percentage of cells in the relevant cell population which are viable.

In a preferred embodiment, cell viability is determined by a "Trypan blue viability exclusion assay". This assay is commonly used for cell viability determination in the field of cell culture. A detailed protocol is set out in the Examples, but in brief: a cell suspension is mixed with 0.4% trypan blue in phosphate buffered solution and counted using a hemocytometer. Live cells appear round and refractile without any blue-dye coloration while dead cells absorb the dye and appear blue. Viability is then expressed as a percentage of viable cells over total cells counted.

A viable cell is defined as a cell that whose membrane integrity is still able to prevent the absorption of trypan blue in a trypan blue exclusion viability assay.

Preferably, the modified cells have at least 5%, preferably 10% or more, more preferably 15%, 20%, 30%, 40%, 50% or more viable cells compared to a control population. Alternatively, or in addition, the modified cells maintain cell viability for a longer period of time compared to cells which have not been modified. For example, modified cells are able to maintain a certain percentage cell viability (e.g., 95%) for a longer period compared to control cells.

Preferably, modified cells have extended cell viability by at least 1 hour, more preferably at least 6 hours, most preferably at least 12 hours or more, e.g., at least 24 hours, at least 36 hours or at least 48 hours, compared to control cells. In highly preferred embodiments, modified cells have extended viability by at least 24 hours before viability begins to drop below 95%, compared to control cells.

The modified cells preferably are capable of higher viable culture densities compared to unmodified control cells. Preferably, the modified cells are capable of 10%, 20%, 30%, 40%, 50%, 60%, 70%, 80%, 90%, 100%, 150%, 200% or higher viable cell density compared to control cells. For example, modified cells may achieve densities as high as $9.6 \times 10^6$ cells/ml.

The modified cells preferably display a delayed onset of expression of an apoptosis marker, preferably caspase 2, caspase 3 or caspase 8. The modified cells may have the property of displaying reduced apoptosis, in terms of longer time of survival for individual cells, or the number of cells which display apoptosis. Preferably, they have the property of being resistant to apoptosis (see below).

Increased Protein Yield

Advantageously, the modified cells are capable of increased protein yield, preferably increased recombinant expressed protein yield, compared to unmodified control cells, as demonstrated in Example 21. Preferably, modified cells are capable of 10%, 20%, 30%, 40%, 50%, 60%, 70%, 80%, 90%, 100%, 150%, 200% or more higher yield compared to control cells. More preferably, modified cells are capable of 2.5×, 3×, 5×, 10× or more higher yield compared to control cells. Preferably, the recombinant expressed protein comprises interferon gamma. We therefore provide a method of expressing a recombinant protein, preferably a biotherapeutic molecule, in a modified cell as described.

Preferably, the modified cells display any one or more of their properties in batch culture, fed-batch culture or preferably both.

Increased Glycosylation

The modified cells preferably are also capable of increased glycosylation of expressed proteins compared to control unmodified cells. The Examples show that the modified cells are capable of maintaining protein glycosylation over extended cell culture time, whether or not loss of cell culture viability has taken place. In highly preferred embodiments, the glycosylation comprises sialyation.

This characteristic of modified cell lines is particularly advantageous in the manufacturing of biotherapeutics as a lower degree of sialyation can decrease the in vivo half-life of protein-based drugs (Varki, 1993, Biotechnol Bioeng 43:423-428; Gramer et al., 1995, Glycobiology 3:97-130).

In preferred embodiments, the glycosylation of the expressed protein is maintained substantially throughout one or more growth phases of cell culture, preferably through at least part of exponential phase (preferably at least through mid-exponential phase), but more preferably also through the point at which maximum viable cell density occurs, more preferably also through a point at which cell death would occur in a parental or unmodified cell. In such cases, the level of glycosylation is preferably maintained at a level where it would decrease in a parental or unmodified cell. In preferred embodiments, the glycosylation is maintained at a level of at least 2.7, preferably at least 2.9 moles of the sugar per mole of expressed protein.

In preferred embodiments, glycosylation of the expressed protein by a modified cell is increased compared to a parental or unmodified cell in a cognate point in the growth phase. In such preferred embodiments, glycosylation may be achieved at a level of at least 2.9, preferably at least 3, 3.1, 3.2, 3.3, 3.4 or 3.5 moles of the sugar per mole of expressed protein.

We further provide for recombinant proteins with increased glycosylation, preferably increased sialyation, made using modified cells as described. Such polypeptides have an increased sialyation, compared to a polypeptide producable from a cell which is not so modified. Preferably, the glycosylation or sialyation is greater than 2.9 mol sialic acid/mol of produced polypeptide, preferably about 3.5 mol of sialic acid/mol of produced polypeptide. In highly preferred embodiments, the expressed protein comprises interferon gamma.

We further provide methods for modifying a cell to display any one or more of the above properties, by modulating its expression of cgFAIM, gFADD, cgPDCD6 and/or cgRequiem.

Apoptosis

According to the invention, increase in cell viability of cgFAIM, cgFADD, cgPDCD6 and/or cgRequiem modified cells results from a decrease in apoptosis in the modified cell populations. Such modified cells may display reduced apoptosis, or be resistant to apoptosis. The modified cells are preferably capable of maintaining a higher viable cell density, preferably for a longer period of time, compared to control cells. Preferably, the number of viable cells in a modified population is higher, for example 10%, 20%, 30%, 40%, 50%, 100%, 200%, 500%, or more, compared to an unmodified control population.

Preferably, modified cells show an extension of viability by at least 6 hours, at least 12 hours, preferably at least 18 hours, and most preferably at least 24 hours compared to control cells. In highly preferred embodiments, caspase 2 and/or caspase 3 and/or caspase 8 expression is delayed by such times compared to control cells.

Accordingly, preferably, apoptosis in a modified cell population is decreased by at least 10%, preferably 25% or more, more preferably 40%, 50%, 75%, 95% or more compared to a control population. In preferred embodiments, the percentage of apoptotic cells in a modified cell population is decreased by such amounts. In highly preferred embodiments, the modified cells are resistant to apoptosis, i.e., display little or no significant apoptosis.

Methods of assaying apoptosis are known in the art, and are described in detail below and in the Examples. A preferred method of assaying apoptosis is set out in Example 14: Apoptosis Assay.

An alternative assay of apoptosis involves quantitation or measurement of levels any one or more of caspase 2, caspase 3 and caspase 8 in the relevant cells. Thus, preferably, levels of any one or more of these caspases is decreased in a modified cell or population compared to one which has not been so modified, by 10%, 20%, 30%, 50%, 70%, 80%, 90% or more. Preferably, modified cells exhibit a delay in expression of any one or more of caspase 2, caspase 3 and caspase 8 by a period of time preferably at least 1 hour, more preferably at least 6 hours, most preferably at least 12 hours or more, e.g., at least 24 hours, at least 36 hours, at least 48 hours, at least 72 hours, at least 144 hours, at least 288 hours, or more, compared to control cells which are not modified. Caspase levels may be assayed by any means known in the art, including RT-PCR, RNAse protection, SDS-PAGE, immunoassays, etc.

Cell death can occur by either of two distinct mechanisms, necrosis or apoptosis. In addition, certain chemical compounds and cells are said to be cytotoxic to the cell, that is, to cause its death.

"Cytotoxicity" refers to the cell killing property of a chemical compound (such as a food, cosmetic, or pharmaceutical) or a mediator cell (cytotoxic T cell). In contrast to necrosis and apoptosis, the term cytotoxicity need not necessarily indicate a specific cellular death mechanism. For example, cell mediated cytotoxicity (that is, cell death mediated by either cytotoxic T lymphocytes [CTL] or natural killer [NK] cells) combines some aspects of both necrosis and apoptosis.

"Necrosis" (also referred to as "accidental" cell death) refers to the pathological process which occurs when cells are exposed to a serious physical or chemical insult. Necrosis occurs when cells are exposed to extreme variance from physiological conditions (e.g., hypothermia, hypoxia) which may result in damage to the plasma membrane. Under physiological conditions direct damage to the plasma membrane is evoked by agents like complement and lytic viruses. Necrosis begins with an impairment of the cell's ability to maintain homeostasis, leading to an influx of water and extracellular ions. Intracellular organelles, most notably the mitochondria, and the entire cell swell and rupture (cell lysis). Due to the ultimate breakdown of the plasma membrane, the cytoplasmic contents including lysosomal enzymes are released into the extracellular fluid. Therefore, in vivo, necrotic cell death is often associated with extensive tissue damage resulting in an intense inflammatory response.

"Apoptosis" ("normal" or "programmed" cell death) refers to the physiological process by which unwanted or useless cells are eliminated during development and other normal biological processes. Apoptosis is a mode of cell death that occurs under normal physiological conditions and the cell is an active participant in its own demise ("cellular suicide"). It is most often found during normal cell turnover and tissue homeostasis, embryogenesis, induction and maintenance of immune tolerance, development of the nervous system and endocrine-dependent tissue atrophy. Cells undergoing apoptosis show characteristic morphological and biochemical features. These features include chromatin aggregation, nuclear and cytoplasmic condensation, partition of cytoplasm and nucleus into membrane bound vesicles (apoptotic bodies) which contain ribosomes, morphologically intact mitochondria and nuclear material. In vivo, these apoptotic bodies are rapidly recognized and phagocytized by either macrophages or adjacent epithelial cells. Due to this efficient mechanism for the removal of apoptotic cells in vivo no inflammatory response is elicited. In vitro, the apoptotic bodies as well as the remaining cell fragments ultimately swell and finally lyse. This terminal phase of in vitro cell death has been termed "secondary necrosis".

Table 1 summarises the various observable differences between necrosis and apoptosis. Preferably, modified cells exhibit a reduction in one or more of these features. Any of these differences, alone or in combination, may be assayed in order to determine whether cell death is occurring by apoptosis or by necrosis.

M. R. (1993); Anal. Biochem. 208, 393; Prigent, P. et al. (1993). J. Immunol; Methods 160, 139; Huang, P. & Plunkett, W. (1992); Anal. Biochem. 207, 163 Bortner, C. D. et al. (1995) Trends Cell Biol. 5, 21; Gold, R. et al. (1994); Lab. Invest. 71, 219.

Apoptosis and cell mediated cytotoxicity are characterized by cleavage of the genomic DNA into discrete fragments prior to membrane disintegration. Accordingly, apoptosis may be assayed by measuring DNA fragmentation, for example, by observing the presence of DNA ladders. DNA fragments may be assayed, for example, as "ladders" (with

TABLE 1

Differential features and significance of necrosis and apoptosis.

| | Necrosis | Apoptosis |
|---|---|---|
| Morphological features | Loss of membrane integrity | Membrane blebbing, but no loss of integrity |
| | | Aggregation of chromatin at the nuclear membrane |
| | Begins with swelling of cytoplasm and mitochondria | Begins with shrinking of cytoplasm and condensation of nucleus |
| | Ends with total cell lysis | Ends with fragmentation of cell into smaller bodies |
| | No vesicle formation, complete lysis | Formation of membrane bound vesicles (apoptotic bodies) |
| | Disintegration (swelling) of organelles | Mitochondria become leaky due to pore formation involving proteins of the bcl-2 family. |
| Biochemical features | Loss of regulation of ion homeostasis | Tightly regulated process involving activation and enzymatic steps |
| | No energy requirement (passive process, also occurs at 4° C.) | Energy (ATP)-dependent (active process, does not occur at 4° C.) |
| | Random digestion of DNA (smear of DNA after agarose gel electrophoresis) | Non-random mono- and oligonucleosomal length fragmentation of DNA (Ladder pattern after agarose gel electrophoresis) |
| | Postlytic DNA fragmentation (= late event of death) | Prelytic DNA fragmentation Release of various factors (cytochrome C, AIF) into cytoplasm by mitochondria |
| | | Activation of caspase cascade |
| | | Alterations in membrane asymmetry (i.e., translocation of phosphatidyl-serine from the cytoplasmic to the extracellular side of the membrane) |
| Physiological significance | Affects groups of contiguous cells | Affects individual cells |
| | Evoked by non-physiological disturbances (complement attack, lytic viruses, hypothermia, hypoxia, ischemica, metabolic poisons) | Induced by physiological stimuli (lack of growth factors, changes in hormonal environment) |
| | Phagocytosis by macrophages | Phagocytosis by adjacent cells or macrophages |
| | Significant inflammatory response | No inflammatory response |

Reference is made to the following documents, which describe apoptosis in detail, as well as various assays for measuring cell death by apoptosis: Schwartzman, R. A. and Cidlowski, J. A. (1993). Endocrine Rev. 14, 133; Vermes, I. and Haanan, C. (1994). Adv. Clin. Chem. 31, 177; Berke, G. (1991). Immunol. Today 12, 396; Krähenbühl, O. and Tschopp, J. (1991). Immunol. Today 12, 399; Van Furth, R. and Van Zwet, T. L. (1988). J. Immunol; Methods 108, 45. Cohen, J. J. (1993) Apoptosis. Immunol. Today 14, 126; Savill, J. S. et al. (1989). J. Clin. Invest. 83, 865; Wyllie, A. H. (1980). Nature 284, 555; Leist, M. et al. (1994) Biochemica No. 3, 18-20; Fraser, A. and Evan, G. (1996) Cell 85, 781-784; Duke, R. C. (1983). Proc. Natl. Acad. Sci. USA 80,6361; Duke, R. C. & Cohen, J. J. (1986). Lymphokine Res. 5, 289; Trauth, B. C. et al. (1994) Eur. J. Cell. Biol. 63, 32, Suppl 40; Matzinger, P. (1991). J. Immunol; Methods 145, 185; Kaeck, the 180 bp multiples as "rungs" of the ladder) derived from populations of cells, or by quantification of histone complexed DNA fragments via, for example, ELISA. Such an assay relies on an one-step sandwich immunoassay to detect nucleosomes. The procedure involves pelleting cells by centrifugation and discarding the supernatant (which contains DNA from necrotic cells that leaked through the membrane during incubation). Cells are resuspended and incubated in lysis buffer. After lysis, intact nuclei are pelleted by centrifugation. An aliquot of the supernatant is transferred to a streptavidin-coated well of a microtiter plate, and nucleosomes in the supernatant are bound with two monoclonal antibodies, anti-histone (biotin-labeled) and anti-DNA (peroxidase-conjugated). Antibody-nucleosome complexes are bound to the microtiter plate by the streptavidin. The immobilized antibody-histone complexes are washed three times to remove cell components that are not immuno-reactive, and the sample is incubated with peroxidase substrate (ABTS®). The amount of colored product (and thus, of immobilized anti-body-histone complexes) is then determined spectrophotometrically.

Several proteases are involved in the early stages of apoptosis. Apoptosis may therefore also be assayed by detecting the presence of, in addition to, or instead of, assaying the activity of, apoptosis-induced proteases such as caspases, e.g., caspase 3. Caspase activation can be analyzed in different ways, for example, by an in vitro enzyme assay of, for example, cellular lysates by capturing of the caspase and measuring proteolytic cleavage of a suitable substrate. Furthermore, caspases may be assayed by detection of cleavage of an in vivo caspase substrate such as PARP (Poly-ADP-Ribose-Polymerase). Cleaved fragments of PARP may be detected with a suitable antibody such as an anti PARP antibody. Protease assays and DNA fragmentation assays are especially suitable for assaying apoptosis in cell populations.

Methods for studying apoptosis in individual cells are also available, such as ISNT and TUNEL enzymatic labeling assays. As noted above, extensive DNA degradation is a characteristic event which often occurs in the early stages of apoptosis. Cleavage of the DNA yields double-stranded, low molecular weight DNA fragments (mono- and oligonucleosomes) as well as single strand breaks ("nicks") in high molecular weight-DNA. In TUNEL, such DNA strand breaks are detected by enzymatic labeling of the free 3'-OH termini with suitable modified nucleotides (such as X-dUTP, X=biotin, DIG or fluorescein). Suitable labeling enzymes include DNA polymerase (nick translation) in ISNT ("in situ nick translation") and terminal deoxynucleotidyl transferase (end labeling) in TUNEL ("TdT-mediated X-dUTP nick end labeling"; Huang, P. & Plunkett, W., 1992, Anal. Biochem. 207, 163; Bortner, C. D. et al., 1995, Trends Cell Biol. 5, 21).

Apoptosis may also be assayed by measuring membrane alterations, including: loss of terminal sialic acid residues from the side chains of cell surface glycoproteins, exposing new sugar residues; emergence of surface glycoproteins that may serve as receptors for macrophage-secreted adhesive molecules such as thrombospondin; and loss of asymmetry in cell membrane phospholipids, altering both the hydrophobicity and charge of the membrane surface. In particular, the human anticoagulant annexin V is a 35-36 kilodalton, Ca2+-dependent phospholipid-binding protein that has a high affinity for phosphatidylserine (PS). In normal viable cells, PS is located on the cytoplasmic surface of the cell membrane. However, in apoptotic cells, PS is translocated from the inner to the outer leaflet of the plasma membrane, thus exposing PS to the external cellular environment. Annexin V may therefore be used to detect phosphatidylserine asymmetrically exposed on the surface of apoptotic cells (Homburg, C. H. E. et al. 1995, *Blood* 85, 532; Verhoven, B. et al., 1995, *J. Exp. Med.* 182, 1597). Furthermore, DNA stains such as DAPI, ethidium bromide and propidium iodide, etc may be used for differential staining to distinguish viable and non-viable cells. Profiles of DNA content may also be used; thus, permeabilized apoptotic cells leak low molecular weight DNA, and detection of "sub-G 1 peaks", or "A 0" cells (cells with lower DNA staining than that of G 1 cells) may be detected by, for example, flow cytometry. Morphological changes characteristic of apoptosis may also be detected in this manner.

Detection of apoptosis-related proteins such as ced-3, ced-4, ced-9 (Ellis, H. M. and Horvitz, H. R., 1986, Cell 44, 817-829; Yuan, J. Y. and Horvitz, H. R., 1990, Dev. Biol. 138, 33-41; Hentgartner, M. O., Ellis, R. E. and Horvitz, H. R., 1992, Nature 356, 494-499.), Fas(CD95/Apo-1; Enari et al., 1996, Nature 380, 723-726), Bcl-2 (Baffy, G. et al., 1993, J. Biol. Chem. 268, 6511-6519; Miyashita, T. and Reed, J. C., 1993, Blood 81, 151-157; Oltvai, Z. N., Milliman, C. L. and Korsmeyer, S. J., 1993, Cell 74, 609-619), p53 (Yonish-Rouach, E. et al., 1991, Nature 352, 345-347), etc by the use of antibodies may also be used to assay apoptosis.

Nucleotide Vectors

The polynucleotides can be incorporated into a recombinant replicable vector. The vector may be used to replicate the nucleic acid in a compatible host cell. Thus in a further embodiment, we provide a method of making polynucleotides by introducing a polynucleotide into a replicable vector, introducing the vector into a compatible host cell, and growing the host cell under conditions which bring about replication of the vector. The vector may be recovered from the host cell. Suitable host cells include bacteria such as *E. coli*, yeast, mammalian cell lines and other eukaryotic cell lines, for example insect Sf9 cells.

Preferably, a polynucleotide in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators.

Vectors may be transformed or transfected into a suitable host cell as described below to provide for expression of a protein. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used, for example, to transfect or transform a host cell.

Control sequences operably linked to sequences encoding the protein include promoters/enhancers and other expression regulation signals. These control sequences may be selected to be compatible with the host cell for which the expression vector is designed to be used in. The term "promoter" is well-known in the art and encompasses nucleic acid regions ranging in size and complexity from minimal promoters to promoters including upstream elements and enhancers.

The promoter is typically selected from promoters which are functional in mammalian cells, although prokaryotic promoters and promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of α-actin, β-actin, tubulin) or, alternatively, a tissue-specific manner (such as promoters of the genes for pyruvate kinase). They may also be promoters that respond to specific stimuli, for example promoters that bind steroid hormone receptors. Viral promoters may also be used, for example the Moloney murine leukaemia virus long terminal repeat (MMLV LTR) promoter, the Rous sarcoma virus (RSV) LTR promoter or the human cytomegalovirus (CMV) IE promoter.

It may also be advantageous for the promoters to be inducible so that the levels of expression of the heterologous gene can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above.

Expression Of cgFAIM, cgFADD, cgPDCD6 and cgRequiem Polypeptides

In order to express a biologically active cgFAIM, cgFADD, cgPDCD6 and/or cgRequiem polypeptide, a *Cricetulus griseus* FAIM, FADD, PDCD6 or Requiem polynucleotide sequence is brought into association with a regulatory sequence so as to enable the regulatory sequence to direct expression of said polynucleotide. Expression of the polypeptide under control of the regulatory sequence is then allowed to happen. Optionally, the polypeptide so produced may be purified.

Preferably, the regulatory sequence is one with which the FAIM, FADD, PDCD6 or Requiem polynucleotide sequence is not naturally associated.

We therefore describe a method of producing polypeptide comprising providing a cell, preferably a *Cricetulus griseus* cell, in which a *Cricetulus griseus* FAIM, FADD, PDCD6 or Requiem polynucleotide sequence has been brought into association with a regulatory sequence so as to enable the regulatory sequence to direct expression of said polynucleotide, and culturing the cell under conditions which enable expression of the polypeptide, and optionally purifying the polypeptide.

We further describe a method of producing a polypeptide comprising: (a) providing an expression sequence produced by bringing a *Cricetulus griseus* FAIM, FADD, PDCD6 or Requiem polynucleotide sequence into association with a regulatory sequence so as to enable the regulatory sequence to direct expression of said polynucleotide; (b) allowing expression of the polypeptide from the expression sequence under control of the regulatory sequence, and (c) optionally purifying the polypeptide.

In particular, the nucleotide sequences encoding the respective nucleic acid or homologues, variants, or derivatives thereof may be inserted into appropriate expression vector, i.e., a vector which contains the necessary elements for the transcription and translation of the inserted coding sequence.

We also provide for a polypeptide produced by any of the above methods.

Methods of enabling expression of cgFAIM, cgFADD, cgPDCD6 and cgRequiem polypeptides are set out below. It will be appreciated that these methods may be suitable for use in embodiments of the methods and compositions described here in which up-regulation of a polypeptide is desired, e.g., up-regulation of cgFADD in order to achieve enhanced cell viability.

One method by which to provide expressed polypeptides is by means of an expression vector, i.e., a vector (e.g., a plasmid) which contains a regulatable promoter, optionally with other regulatory sequences such as enhancers, which is operably linked to a sequence encoding a polypeptide of interest which has been cloned into the expression vector.

Methods which are well known to those skilled in the art may be used to construct expression vectors containing sequences encoding cgFAIM, cgFADD, cgPDCD6 and cgRequiem and appropriate transcriptional and translational control elements. These methods include in vitro recombinant DNA techniques, synthetic techniques, and in vivo genetic recombination. Such techniques are described in Sambrook, J. et al. (1989; Molecular Cloning, A Laboratory Manual, ch. 4, 8, and 16-17, Cold Spring Harbor Press, Plainview, N.Y.) and Ausubel, F. M. et al. (1995 and periodic supplements; Current Protocols in Molecular Biology, ch. 9, 13, and 16, John Wiley & Sons, New York, N.Y.).

A variety of expression vector/host systems may be utilized to contain and express sequences encoding cgFAIM, cgFADD, cgPDCD6 and/or cgRequiem. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. Any suitable host cell may be employed.

The "control elements" or "regulatory sequences" are those non-translated regions of the vector (i.e., enhancers, promoters, and 5' and 3' untranslated regions) which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jolla, Calif.) or PSPORT1 plasmid (GIBCO/BRL), and the like, may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector.

In mammalian cell systems, promoters from mammalian genes or from mammalian viruses are preferable. If it is necessary to generate a cell line that contains multiple copies of the sequence encoding cgFAIM, cgFADD, cgPDCD6 and/ or cgRequiem, vectors based on SV40 or EBV may be used with an appropriate selectable marker.

In bacterial systems, a number of expression vectors may be selected depending upon the use intended for cgFAIM, cgFADD, cgPDCD6 and/or cgRequiem. For example, when large quantities of cgFAIM, cgFADD, cgPDCD6 and/or cgRequiem are needed for the induction of antibodies, vectors which direct high level expression of fusion proteins that are readily purified may be used. Such vectors include, but are not limited to, multifunctional *E. coli* cloning and expression vectors such as BLUESCRIPT (Stratagene), in which the sequence encoding cgFAIM, cgFADD, cgPDCD6 and/or cgRequiem may be ligated into the vector in frame with sequences for the amino-terminal Met and the subsequent 7 residues of β-galactosidase so that a hybrid protein is produced, pIN vectors (Van Heeke, G. and S. M. Schuster (1989) J. Biol. Chem. 264:5503-5509), and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. For reviews, see Ausubel (supra) and Grant et al. (1987; Methods Enzymol. 153:516-544).

In cases where plant expression vectors are used, the expression of sequences encoding cgFAIM, cgFADD, cgPDCD6 and/or cgRequiem may be driven by any of a number of promoters. For example, viral promoters such as the 35S and 19S promoters of CaMV may be used alone or in combination with the omega leader sequence from TMV. (Takamatsu, N. (1987) EMBO J. 6:307-311.) Alternatively, plant promoters such as the small subunit of RUBISCO or heat shock promoters may be used. (Coruzzi, G. et al. (1984) EMBO J. 3:1671-1680; Broglie, R. et al. (1984) Science 224:838-843; and Winter, J. et al. (1991) Results Probl. Cell Differ. 17:85-105.) These constructs can be introduced into plant cells by direct DNA transformation or pathogen-mediated transfection. Such techniques are described in a number of generally available reviews. (See, for example, Hobbs, S. or Murry, L. E. in McGraw Hill Yearbook of Science and Technology (1992) McGraw Hill, New York, N.Y.; pp. 191-196.).

An insect system may also be used to express cgFAIM, cgFADD, cgPDCD6 and/or cgRequiem. For example, in one such system, *Autographa californica* nuclear polyhedrosis virus (AcNPV) is used as a vector to express foreign genes in *Spodoptera frugiperda* cells or in *Trichoplusia* larvae. The sequences encoding cgFAIM, cgFADD, cgPDCD6 and/or cgRequiem may be cloned into a non-essential region of the virus, such as the polyhedrin gene, and placed under control of the polyhedrin promoter. Successful insertion of cgFAIM, cgFADD, cgPDCD6 and/or cgRequiem will render the polyhedrin gene inactive and produce recombinant virus lacking coat protein. The recombinant viruses may then be used to infect, for example, *S. frugiperda* cells or *Trichoplusia* larvae in which cgFAIM, cgFADD, cgPDCD6 and/or cgRequiem may be expressed. (Engelhard, E. K. et al. (1994) Proc. Nat. Acad. Sci. 91:3224-3227.)

In mammalian host cells, a number of viral-based expression systems may be utilized. In cases where an adenovirus is used as an expression vector, sequences encoding cgFAIM, cgFADD, cgPDCD6 and/or cgRequiem may be ligated into an adenovirus transcription/translation complex consisting of the late promoter and tripartite leader sequence. Insertion in a non-essential E1 or E3 region of the viral genome may be used to obtain a viable virus which is capable of expressing cgFAIM, cgFADD, cgPDCD6 and/or cgRequiem in infected host cells. (Logan, J. and T. Shenk (1984) Proc. Natl. Acad. Sci. 81:3655-3659.) In addition, transcription enhancers, such as the Rous sarcoma virus (RSV) enhancer, may be used to increase expression in mammalian host cells.

Thus, for example, the cgFAIM, cgFADD, cgPDCD6 and/or cgRequiem proteins are expressed in either human embryonic kidney 293 (HEK293) cells or adherent dhfr CHO cells. To maximize receptor expression, typically all 5' and 3' untranslated regions (UTRs) are removed from the receptor cDNA prior to insertion into a pCDN or pcDNA3 vector. The cells are transfected with individual receptor cDNAs by lipofectin and selected in the presence of 400 mg/ml G418. After 3 weeks of selection, individual clones are picked and expanded for further analysis. HEK293 or CHO cells transfected with the vector alone serve as negative controls. To isolate cell lines stably expressing the individual receptors, about 24 clones are typically selected and analyzed by Northern blot analysis. Receptor mRNAs are generally detectable in about 50% of the G418-resistant clones analyzed.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding cgFAIM, cgFADD, cgPDCD6 and/or cgRequiem. Such signals include the ATG initiation codon and adjacent sequences. In cases where sequences encoding cgFAIM, cgFADD, cgPDCD6 and/or cgRequiem and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used, such as those described in the literature. (Scharf, D. et al. (1994) Results Probl. Cell Differ. 20:125-162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and W138), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing cgFAIM, cgFADD, cgPDCD6 and/or cgRequiem can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes (Wigler, M. et al. (1977) Cell 11:223-32) and adenine phosphoribosyltransferase genes (Lowy, I. et al. (1980) Cell 22:817-23), which can be employed in tk⁻ or apr⁻ cells, respectively. Also, antimetabolite, antibiotic, or herbicide resistance can be used as the basis for selection. For example, dhfr confers resistance to methotrexate (Wigler, M. et al. (1980) Proc. Natl. Acad. Sci. 77:3567-70); npt confers resistance to the aminoglycosides neomycin and G-418 (Colbere-Garapin, F. et al (1981) J. Mol. Biol. 150:1-14); and als or pat confer resistance to chlorsulfuron and phosphinothricin acetyltransferase, respectively (Murry, supra). Additional selectable genes have been described, for example, trpB, which allows cells to utilize indole in place of tryptophan, or hisD, which allows cells to utilize histinol in place of histidine. (Hartman, S. C. and R. C. Mulligan (1988) Proc. Natl. Acad. Sci. 85:8047-51.) Recently, the use of visible markers has gained popularity with such markers as anthocyanins, β-glucuronidase and its substrate GUS, and luciferase and its substrate luciferin. These markers can be used not only to identify transformants, but also to quantify the amount of transient or stable protein expression attributable to a specific vector system. (Rhodes, C. A. et al. (1995) Methods Mol. Biol. 55:121-131.)

Although the presence/absence of marker gene expression suggests that the gene of interest is also present, the presence and expression of the gene may need to be confirmed. For example, if the sequence encoding cgFAIM, cgFADD, cgPDCD6 and/or cgRequiem is inserted within a marker gene sequence, transformed cells containing sequences encoding cgFAIM, cgFADD, cgPDCD6 and/or cgRequiem can be identified by the absence of marker gene function. Alternatively, a marker gene can be placed in tandem with a sequence encoding cgFAIM, cgFADD, cgPDCD6 and/or cgRequiem under the control of a single promoter. Expression of the marker gene in response to induction or selection usually indicates expression of the tandem gene as well.

Alternatively, host cells which contain the nucleic acid sequence encoding cgFAIM, cgFADD, cgPDCD6 and/or cgRequiem and express cgFAIM, cgFADD, cgPDCD6 and/or cgRequiem may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding cgFAIM, cgFADD, cgPDCD6 and/or cgRequiem can be detected by DNA-DNA or DNA-RNA hybridization or amplification using probes or fragments or fragments of polynucleotides encoding cgFAIM, cgFADD, cgPDCD6 and/or cgRequiem. Nucleic acid amplification based assays involve the use of oligonucleotides or oligomers based on the sequences encoding cgFAIM, cgFADD, cgPDCD6 and/or cgRequiem to detect transformants containing DNA or RNA encoding cgFAIM, cgFADD, cgPDCD6 and/or cgRequiem.

A variety of protocols for detecting and measuring the expression of cgFAIM, cgFADD, cgPDCD6 and/or cgRequiem, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on cgFAIM, cgFADD, cgPDCD6 and/or cgRequiem is preferred, but a competitive binding assay may be employed. These and other assays are well described in the art, for example, in Hampton, R. et al. (1990; Serological Methods, a Laboratory Manual, Section IV, APS Press, St Paul, Minn.) and in Maddox, D. E. et al. (1983; J. Exp. Med. 158:1211-1216).

A wide variety of labels and conjugation techniques are known by those skilled in the art and may be used in various nucleic acid and amino acid assays. Means for producing labeled hybridization or PCR probes for detecting sequences related to polynucleotides encoding cgFAIM, cgFADD, cgPDCD6 and/or cgRequiem include oligolabeling, nick translation, end-labeling, or PCR amplification using a labeled nucleotide. Alternatively, the sequences encoding cgFAIM, cgFADD, cgPDCD6 and/or cgRequiem, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding cgFAIM, cgFADD, cgPDCD6 and/or cgRequiem may be cultured under conditions suitable for the expression and recovery of the protein from cell culture. The protein produced by a transformed cell may be located in the cell membrane, secreted or contained intracellularly depending on the sequence and/or the vector used. As will be understood by those of skill in the art, expression vectors containing polynucleotides which encode cgFAIM, cgFADD, cgPDCD6 and/or cgRequiem may be designed to contain signal sequences which direct secretion of cgFAIM, cgFADD, cgPDCD6 and/or cgRequiem through a prokaryotic or eukaryotic cell membrane. Other constructions may be used to join sequences encoding cgFAIM, cgFADD, cgPDCD6 and/or cgRequiem to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif.), between the purification domain and the cgFAIM, cgFADD, cgPDCD6 and/or cgRequiem encoding sequence may be used to facilitate purification. One such expression vector provides for expression of a fusion protein containing cgFAIM, cgFADD, cgPDCD6 and/or cgRequiem and a nucleic acid encoding 6 histidine residues preceding a thioredoxin or an enterokinase cleavage site. The histidine residues facilitate purification on immobilized metal ion affinity chromatography (IMIAC; described in Porath, J. et al. (1992) Prot. Exp. Purif. 3: 263-281), while the enterokinase cleavage site provides a means for purifying cgFAIM, cgFADD, cgPDCD6 and/or cgRequiem from the fusion protein. A discussion of vectors which contain fusion proteins is provided in Kroll, D. J. et al. (1993; DNA Cell Biol. 12:441-453).

Fragments of cgFAIM, cgFADD, cgPDCD6 and/or cgRequiem, as well as whole length polypeptides, may be produced not only by recombinant production, but also by direct peptide synthesis using solid-phase techniques. (Merrifield J. (1963) J. Am. Chem. Soc. 85:2149-2154.) Protein synthesis may be performed by manual techniques or by automation. Automated synthesis may be achieved, for example, using the Applied Biosystems 431A peptide synthesizer (Perkin Elmer). Various fragments of cgFAIM, cgFADD, cgPDCD6 and/or cgRequiem may be synthesized separately and then combined to produce the full length molecule.

Other methods of expression are also known, for example, a method known as "gene activation" may be employed to modulate activity or expression of cgFAIM, cgFADD, cgPDCD6 and cgRequiem. This method is described in detail in U.S. Pat. No. 5,641,670, hereby incorporated by reference. In essence, the gene activation method is based upon the recognition that the regulation or activity of endogenous genes of interest in a cell can be altered by inserting into the cell genome, at a preselected site, through homologous recombination, a suitable DNA construct comprising: (a) a targeting sequence; (b) a regulatory sequence; (c) an exon and (d) an unpaired splice-donor site, wherein the targeting sequence directs the integration of elements (a)-(d) such that the elements (b)-(d) are operatively linked to the endogenous gene. The DNA construct may alternatively comprise: (a) a targeting sequence, (b) a regulatory sequence, (c) an exon, (d) a splice-donor site, (e) an intron, and (f) a splice-acceptor site, wherein the targeting sequence directs the integration of elements (a)-(f) such that the elements of (b)-(f) are operatively linked to the first exon of the endogenous gene.

The targeting sequences used are selected with reference to the site into which the DNA is to be inserted. In both arrangements the targeting event is used to create a new transcription unit, which is a fusion product of sequences introduced by the targeting DNA constructs and the endogenous cellular gene. For example, the formation of the new transcription unit allows transcriptionally silent genes (genes not expressed in a cell prior to transfection) to be activated in host cells by introducing into the host cell's genome a DNA construct as described. The expression of an endogenous gene such as cgFAIM, cgFADD, cgPDCD6 or cgRequiem which is expressed in a cell as obtained can be altered in that it is increased, reduced, including eliminated, or the pattern of regulation or induction may be changed through use of the gene activation method.

Antibodies

Specific antagonists of cgFAIM, cgFADD, cgPDCD6 and/or cgRequiem, which may be used to regulate the activity of these proteins and may include antibodies against the protein(s). In particular, antibodies capable of binding to cgFADD, cgPDCD6 and cgRequiem, and preferably capable of inhibiting any biological activity thereof, are suitable for use in down-regulating expression of the relevant protein for enhancing cell viability.

We therefore provide in particular for anti-cgFADD, anti-cgFAIM, anti-cgPDCD6 and anti-cgRequiem antibodies, as well as methods of producing them.

Antibodies, as used herein, refers to complete antibodies or antibody fragments capable of binding to a selected target, and including Fv, ScFv, Fab' and F(ab')$_2$, monoclonal and polyclonal antibodies, engineered antibodies including chimeric, CDR-grafted and humanized antibodies, and artificially selected antibodies produced using phage display or alternative techniques. Small fragments, such as Fv and ScFv, possess advantageous properties for diagnostic and therapeutic applications on account of their small size and consequent superior tissue distribution.

The anti-cgFAIM, cgFADD, cgPDCD6 and cgRequiem antibodies described here may be used for the detection of the relevant protein, for example, within the context of a cell. Accordingly, they may be altered antibodies comprising an effector protein such as a label. Especially preferred are labels which allow the imaging of the distribution of the antibody in vivo or in vitro. Such labels may be radioactive labels or radio-opaque labels, such as metal particles, which are readily visualisable within an embryo or a cell mass. Moreover, they may be fluorescent labels or other labels which are visualisable on tissue samples.

Recombinant DNA technology may be used to improve the antibodies as described here. Thus, chimeric antibodies may be constructed in order to decrease the immunogenicity thereof in diagnostic or therapeutic applications. Moreover, immunogenicity may be minimised by humanizing the antibodies by CDR grafting [see European Patent Application 0 239 400 (Winter)] and, optionally, framework modification [EP 0 239 400].

Anti-cgFAIM, cgFADD, cgPDCD6 and cgRequiem antibodies may be obtained from animal serum, or, in the case of monoclonal antibodies or fragments thereof, produced in cell culture. Recombinant DNA technology may be used to produce the antibodies according to established procedure, in bacterial or preferably mammalian cell culture. The selected cell culture system preferably secretes the antibody product.

Therefore, we disclose a process for the production of an antibody comprising culturing a host, e.g. *E. coli* or a mammalian cell, which has been transformed with a hybrid vector comprising an expression cassette comprising a promoter operably linked to a first DNA sequence encoding a signal peptide linked in the proper reading frame to a second DNA sequence encoding said antibody protein, and isolating said protein.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. foetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2×YT, or M9 Minimal Medium, and for yeast in medium YPD, YEPD, Minimal Medium, or Complete Minimal propout Medium.

In vitro production provides relatively pure antibody preparations and allows scale-up to give large amounts of the desired antibodies. Techniques for bacterial cell, yeast or mammalian cell cultivation are known in the art and include homogeneous suspension culture, e.g. in an airlift reactor or in a continuous stirrer reactor, or immobilised or entrapped cell culture, e.g. in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, incorporated herein by reference. Techniques for the preparation of recombinant antibody molecules is described in the above references and also in, for example, EP 0623679; EP 0368684 and EP 0436597, which are incorporated herein by reference.

The cell culture supernatants are screened for the desired antibodies, for example by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with cgFAIM, cgFADD, cgPDCD6 and/or cgRequiem, or fragments thereof, or with Protein-A.

Hybridoma cells secreting the monoclonal antibodies are also provided. Preferred hybridoma cells are genetically stable, secrete monoclonal antibodies of the desired specificity and can be activated from deep-frozen cultures by thawing and recloning.

Also included is a process for the preparation of a hybridoma cell line secreting monoclonal antibodies directed to cgFAIM, cgFADD, cgPDCD6 and/or cgRequiem, characterised in that a suitable mammal, for example a Balb/c mouse, is immunised with a one or more cgFAIM, cgFADD, cgPDCD6 and/or cgRequiem polypeptides, or antigenic fragments thereof; antibody-producing cells of the immunised mammal are fused with cells of a suitable myeloma cell line, the hybrid cells obtained in the fusion are cloned, and cell clones secreting the desired antibodies are selected. For example spleen cells of Balb/c mice immunised with cgFAIM, cgFADD, cgPDCD6 and/or cgRequiem are fused with cells of the myeloma cell line PAI or the myeloma cell line Sp2/0-Ag14, the obtained hybrid cells are screened for secretion of the desired antibodies, and positive hybridoma cells are cloned.

Preferred is a process for the preparation of a hybridoma cell line, characterised in that Balb/c mice are immunised by injecting subcutaneously and/or intraperitoneally between 10 and $10^7$ and $10^8$ cells expressing cgFAIM, cgFADD, cgPDCD6 and/or cgRequiem and a suitable adjuvant several times, e.g. four to six times, over several months, e.g. between two and four months, and spleen cells from the immunised mice are taken two to four days after the last injection and fused with cells of the myeloma cell line PAI in the presence of a fusion promoter, preferably polyethylene glycol. Preferably the myeloma cells are fused with a three- to twenty fold excess of spleen cells from the immunised mice in a solution containing about 30% to about 50% polyethylene glycol of a molecular weight around 4000. After the fusion the cells are expanded in suitable culture media as described hereinbefore, supplemented with a selection medium, for example HAT medium, at regular intervals in order to prevent normal myeloma cells from overgrowing the desired hybridoma cells.

Recombinant DNAs comprising an insert coding for a heavy chain variable domain and/or for a light chain variable domain of antibodies directed to cgFAIM, cgFADD, cgPDCD6 and/or cgRequiem as described hereinbefore are also disclosed. By definition such DNAs comprise coding single stranded DNAs, double stranded DNAs consisting of said coding DNAs and of complementary DNAs thereto, or these complementary (single stranded) DNAs themselves.

Furthermore, DNA encoding a heavy chain variable domain and/or for a light chain variable domain of antibodies directed to cgFAIM, cgFADD, cgPDCD6 and/or cgRequiem can be enzymatically or chemically synthesised DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted or exchanged with one or more other amino acids. Preferably said modification(s) are outside the CDRs of the heavy chain variable domain and/or of the light chain variable domain of the antibody. Such a mutant DNA is also intended to be a silent mutant wherein one or more nucleotides are replaced by other nucleotides with the new codons coding for the same amino acid(s). Such a mutant sequence is also a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Also disclosed are recombinant DNAs comprising an insert coding for a heavy chain murine variable domain of an antibody directed to cgFAIM, cgFADD, cgPDCD6 and/or cgRequiem fused to a human constant domain g, for example γ1, γ2, γ3 or γ4, preferably γ1 or γ4. Likewise recombinant DNAs comprising an insert coding for a light chain murine variable domain of an antibody directed to cgFAIM, cgFADD, cgPDCD6 and/or cgRequiem fused to a human constant domain κ or λ, preferably κ are also disclosed.

In another embodiment, we disclose recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA coding for a peptide facilitating the purification of the antibody and/or a cleavage site and/or a peptide spacer and/or an effector molecule.

The DNA coding for an effector molecule is intended to be a DNA coding for the effector molecules useful in diagnostic or therapeutic applications. Thus, effector molecules which are toxins or enzymes, especially enzymes capable of catalysing the activation of prodrugs, are particularly indicated. The DNA encoding such an effector molecule has the sequence of a naturally occurring enzyme or toxin encoding DNA, or a mutant thereof, and can be prepared by methods well known in the art.

Formulation and Administration

Peptides and polypeptides, such as the cgFAIM, cgFADD, cgPDCD6 and/or cgRequiem peptides and polypeptides, nucleic acids and polynucleotides and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. We further describe pharmaceutical packs and kits comprising one or more containers filled with one or more of the ingredients of the aforementioned compositions.

Polypeptides and other compounds may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localize, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1-100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Pharmaceutical Compositions

We also provide a pharmaceutical composition comprising administering a therapeutically effective amount of the polypeptide, polynucleotide, peptide, vector or antibody (such as a cgFAIM, cgFADD, cgPDCD6 and/or cgRequiem polypeptide, etc) and optionally a pharmaceutically acceptable carrier, diluent or excipients (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition as described here may be formulated to be delivered using a mini-pump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Vaccines

Another embodiment relates to a method for inducing an immunological response in a mammal which comprises inoculating the mammal with the cgFAIM, cgFADD, cgPDCD6 and/or cgRequiem polypeptide, or a fragment thereof, adequate to produce antibody and/or T cell immune response to protect said animal from cgFAIM, cgFADD, cgPDCD6 and/or cgRequiem associated disease.

Yet another embodiment relates to a method of inducing immunological response in a mammal which comprises delivering a cgFAIM, cgFADD, cgPDCD6 and/or cgRequiem polypeptide via a vector directing expression of a cgFAIM, cgFADD, cgPDCD6 and/or cgRequiem polynucleotide in vivo in order to induce such an immunological response to produce antibody to protect said animal from diseases.

A further embodiment relates to an immunological/vaccine formulation (composition) which, when introduced into a mammalian host, induces an immunological response in that mammal to a cgFAIM, cgFADD, cgPDCD6 and/or cgRequiem polypeptide wherein the composition comprises a cgFAIM, cgFADD, cgPDCD6 and/or cgRequiem polypeptide or cgFAIM, cgFADD, cgPDCD6 and/or cgRequiem gene. The vaccine formulation may further comprise a suitable carrier.

Since the cgFAIM, cgFADD, cgPDCD6 and/or cgRequiem polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Vaccines may be prepared from one or more polypeptides or peptides as described here.

The preparation of vaccines which contain an immunogenic polypeptide(s) or peptide(s) as active ingredient(s), is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof.

In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further examples of adjuvants and other agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.).

Typically, adjuvants such as Amphigen (oil-in-water), Alhydrogel (aluminum hydroxide), or a mixture of Amphigen and Alhydrogel are used. Only aluminum hydroxide is approved for human use.

The proportion of immunogen and adjuvant can be varied over a broad range so long as both are present in effective amounts. For example, aluminum hydroxide can be present in an amount of about 0.5% of the vaccine mixture ($Al_2O_3$ basis). Conveniently, the vaccines are formulated to contain a final concentration of immunogen in the range of from 0.2 to 200 µg/ml, preferably 5 to 50 µg/ml, most preferably 15 µg/ml.

After formulation, the vaccine may be incorporated into a sterile container which is then sealed and stored at a low temperature, for example 4° C., or it may be freeze-dried. Lyophilisation permits long-term storage in a stabilised form.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

The polypeptides described here may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The pharmaceutical and vaccine compositions as disclosed here may be administered by direct injection. The composition may be formulated for parenteral, mucosal, intramuscular, intravenous, subcutaneous, intraocular or transdermal administration. Typically, each protein may be administered at a dose of from 0.01 to 30 mg/kg body weight, preferably from 0.1 to 10 mg/kg, more preferably from 0.1 to 1 mg/kg body weight.

The term "administered" includes delivery by viral or non-viral techniques. Viral delivery mechanisms include but are not limited to adenoviral vectors, adeno-associated viral (AAV) vectors, herpes viral vectors, retroviral vectors, lentiviral vectors, and baculoviral vectors. Non-viral delivery mechanisms include lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestible solution; a parenteral route where delivery is by an injectable form, such as, for example, an intravenous, intramuscular or subcutaneous route.

The term "co-administered" means that the site and time of administration of each of for example, the polypeptide and an additional entity such as adjuvant are such that the necessary modulation of the immune system is achieved. Thus, whilst the polypeptide and the adjuvant may be administered at the same moment in time and at the same site, there may be advantages in administering the polypeptide at a different time and to a different site from the adjuvant. The polypeptide and adjuvant may even be delivered in the same delivery vehicle—and the polypeptide and the antigen may be coupled and/or uncoupled and/or genetically coupled and/or uncoupled.

The cgFAIM, cgFADD, cgPDCD6 and/or cgRequiem polypeptide, polynucleotide, peptide, nucleotide, antibody etc and optionally an adjuvant may be administered separately or co-administered to the host subject as a single dose or in multiple doses.

The vaccine composition and pharmaceutical compositions described here may be administered by a number of different routes such as injection (which includes parenteral, subcutaneous and intramuscular injection) intranasal, mucosal, oral, intra-vaginal, urethral or ocular administration.

The vaccines and pharmaceutical compositions described here may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, may be 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer.

EXAMPLES

Example 1

Cell Lines & Cell Culture

CHO IFN-γ is a Chinese Hamster Ovary cell line that had been adapted to grow in suspension. It was originally derived from dehydroxyfolate reductase negative (DHFR⁻), Dukx cells (Urlaub & Chasin 1980). CHO IFN-γ had been cotransfected with genes for DHFR and human interferon-γ (Scahill et al. 1983).

CHO IFN-γ is maintained in glucose/glutamine-free HyQ CHO MPS media (Hyclone, Logan, Utah) supplemented with 4 mM glutamine, 20 mM glucose and 0.25 μM methotrexate (Sigma, St. Louis, Mo.).

Example 2

Total RNA Extraction & First Strand cDNA Synthesis

Total RNA is extracted from CHO K1 cells using TRIZOL™ (Invitrogen). All reverse transcription reagents are from Promega. Full length cDNA is synthesized using Moloney Murine Leukaemia Virus reverse transcriptase for 1 hr at 42° C. in a reaction mix containing 1× reverse transcription buffer, 10 mM of each dNTPs and 25 units of recombinant RNAsin® ribonuclease inhibitor.

Example 3

Gene Specific PCR

The cDNA prepared from CHO K1 total RNA is used as a template for gene specific PCR. All PCR reagents are from Promega.

Example 4

Gene Specific Cloning of *Cricetulus griseus* FAIM

The coding region of FAIM is amplified using a 5' PCR primer, 5'-GCCGCGAGAGCTGCTGACTACGTCGTGG-3' (SEQ ID NO: 17) and a 3' PCR primer 5'-GTTACTGTG-GTGAGATATGAATGGGTTTGG-3' (SEQ ID NO: 18). The PCR reaction mix contains 1 μL of cDNA template, 1× Reaction buffer, 200 μM of each dNTP, 2.0 mM MgCl₂, 1 μM of each primer and Taq DNA polymerase mix (Total 5 U). PCR conditions are: 94° C. for 5 min, followed by 31 cycles of 94° C. for 1 min, 58° C. for 1 min and 72° C. for 2 min and a final extension at 72° C. for 10 min. The PCR product is then subcloned into pCR®-TOPO® (Invitrogen, Grand Island, N.Y.) for sequencing.

*Cricetulus griseus* FAIM (cgFAIM)

The sequence of cgFAIM is set out in SEQ ID NO: 1 and SEQ ID NO: 5. The *Cricetulus griseus* sequence encodes for a 179-amino acid protein.

Fas which, is also known as CD95 or APO-1, is a receptor from the tumor necrosis factor (TNF) receptor family that plays a major role in receptor-mediated apoptosis pathway. The extracellular region of TNF receptor family have 2-6 repeats of cysteine-rich subdomain. Fas activation initiates intracellular signaling cascade through the oligomerization of caspase 8. Caspase 8 has been shown to be one of the initiator caspases responsible for the cascade-like activation of effector caspases (Srinivasula et al. 1996). Fas has also been shown to cause mitochondrial cytochrome c release that results in the activation of caspase 9 and other effector caspases (Li et al. 1997).

Fas apoptosis inhibitory molecule (FAIM) had been found to be an inducible protein that can confer resistance to Fas induced apoptosis (Schneider et al. 1999; Rothstein et al. 2000). It has been shown that together with sIg signals, FAIM expression in B cells is able to block Fas killing and does so by blocking a step in the Fas signaling pathway before the activation of caspase 3 (Schneider et al. 1999). FAIM has been shown to exist in two alternatively spliced forms with FAIM-S broadly expressed while FAIM-L is brain tissue-specific (Zhong et al, 2001). FAIM sequence also seemed to be highly conserved in different species suggesting an important phylogeny role.

Example 5

Gene Specific Cloning of *Cricetulus griseus* FADD

The partial coding region of FADD is amplified using a 5' PCR primer 5'-CCATGGACCCATTCCTGGTGC-3' (SEQ ID NO: 19) and a 3' PCR primer 5'-TTCTTCCACCAGGT-CAGC-CACC-3' (SEQ ID NO: 20). The PCR reaction mix contains 1 µL of cDNA template, 1× Reaction buffer, 200 µM of each dNTP, 1.5 mM MgCl$_2$, 1 µM of each primer and Taq DNA polymerase mix (Total 5 U).

PCR conditions are: 94° C. for 5 min, followed by 31 cycles of 94° C. for 1 min, 55° C. for 1 min and 72° C. for 2 min and a final extension at 72° C. for 10 min. The PCR product is then subcloned into pCR®-TOPO® (Invitrogen, Grand Island, N.Y.) for sequencing.

*Cricetulus griseus* FADD (cgFADD)

The sequence of cgFADD is set out in SEQ ID NO: 2 and SEQ ID NO: 6.

FADD is common mediator of both CD95 (Fas/APO-1) and tumor necrosis factor (TNF) receptor-induced apoptosis (Chinnaiyan et al 1996). FADD which contains both death and death effector domains is an important mediator of caspase 8 activation upon Fas engagement (Chinnaiyan et al. 1995). We describe the modulation of expression of cgFADD by use of an artificially engineered FADD molecule, FADD DN that only contained only the apoptosis receptor binding death domain and not the death effector domain of FADD. It is the effector domain which causes the activation of further downstream apoptosis cascade by recruiting caspase to the death-inducing signaling complex. The methods described here enable over-expression of an engineered form of FADD, i.e., a dominant negative, and use of such an engineered molecule to prevent caspase recruitment by competing with native FADD and thus breaking the apoptosis cascade.

Example 6

Gene Specific Cloning of *Cricetulus griseus* PDCD 6

The partial coding region of PDCD6 is amplified using a 5'-PCR primer, 5'-GCCCATGGCTGCCTACTCCTA-3' (SEQ ID NO: 21) and a 3'-PCR primer, 5'-AATCCAGC-CATCCTGAT-CCGT-3' (SEQ ID NO: 22). The PCR reaction mix contains 1 µL of cDNA template, 1× Reaction buffer, 200 µM of each dNTP, 1.5 mM MgCl$_2$, 1 µM of each primer and Taq DNA polymerase mix (Total 5 U).

PCR conditions are: 94° C. for 5 min, followed by 31 cycles of 94° C. for 1 min, 52° C. for 1 min and 72° C. for 2 min and a final extension at 72° C. for 10 min. The PCR product is then subcloned into pCR®-TOPO®(Invitrogen, Grand Island, N.Y.) for sequencing. The PCR product obtained is purified and cloned into pCR 2.1-Topo vector and sequenced. The 3'-RACE primer is 5'-CAGCGGGT-TGATAAAGACAGGAGTGGAGTG-3' (SEQ ID NO: 23).

The 3'-RACE PCR products are separated by electrophoresis in 1% agarose gel containing ethidium bromide, with the relevant band excised and gel extracted using the Qiagen kit before being cloned into pCR®-TOPO® (Invitrogen, Grand Island, N.Y.) for sequencing.

*Cricetulus griseus* PDCD6 (cg PDCD6)

The sequence of cgPDCD6 is set out in SEQ ID NO: 3 and SEQ ID NO: 7. The *Cricetulus griseus* sequence encodes a 191-amino acid protein.

Also known as apoptosis-linked gene 2 (ALG-2), PDCD6 encodes for a calcium-binding protein that belonged to the penta-EF-hand protein family. There are indications that it participates in receptor-, Fas- and glucocorticoid-induced apoptosis (Vito et al. 1996; Krebs & Klemenz, 2000 and Jung et al., 2001). Interestingly, Jang et al. 2002 demonstrated that ALG-2 deficiency resulted in no block of apoptosis induced by TCR, FAS or dexamethasone signals.

Example 7

Gene Specific Cloning of *Cricetulus griseus* Requiem

The partial coding region of Requiem is amplified using a 5'-PCR primer, 5'-ATG-GCGGCTGTGGTGGAGAAT-3' (SEQ ID NO: 24) and a 3'-PCR primer, 5'-GGAGTTCTG-GTTCTGGTAG-ATGG-3' (SEQ ID NO: 25). The PCR reaction mix contained 1 µL of cDNA template, 1× Reaction buffer, 200 µM of each dNTP, 2.0 mM MgCl$_2$, 1 µM of each primer and Taq DNA polymerase mix (Total 5 U).

PCR conditions are: 94° C. for 5 min, followed by 60 cycles of 94° C. for 1 min, 44° C. for min and 72° C. for 2 min and a final extension at 72° C. for 10 min. The PCR product is then subcloned into pCR®-TOPO® (Invitrogen, Grand Island, N.Y.) for sequencing. The PCR product obtained is purified and cloned into pCR 2.1-Topo vector and sequenced. The 3'-RACE primer is 5'-GCCTCAGTTACCACTATGC-CCATTCCCACC-3' (SEQ ID NO: 26).

The 3'-RACE PCR products are separated by electrophoresis in 1% agarose gel containing ethidium bromide, with the relevant band excised and gel extracted using the Qiagen kit before being cloned into pCR®-TOPO® (Invitrogen, Grand Island, N.Y.) for sequencing.

*Cricetulus griseus* Requiem (cgRequiem)

The sequence of cgRequiem is set out in SEQ ID NO: 4 and SEQ ID NO: 8. The *Cricetulus griseus* sequence encodes for a 391-amino acid protein.

Requiem, which is also known as ubi-d4, is a zinc finger gene essential for the activation of caspases in myeloid cells (Gabig et al. 1994). It was suggested that Requiem is likely to encode a transcription factor required for apoptosis response following survival factor withdrawal (Gabig et al. 1994). In addition, Gabig et al. (1998) later detected the protein both in cytoplasmic and nuclear subcellular fractions of murine myeloid cells and human K562 leukemia cells thereby suggesting that the protein may have a function distinct from that of a transcription factor.

Example 8

*Cricetulus griseus* FAIM Expression Vector Construction

In summary, the verified PCR product from FAIM gene specific PCR that is cloned into pCR®-TOPO® (Invitrogen, Grand Island, N.Y.), is subcloned into pcDNA3.1(+) (Invitrogen) and sequenced again. The final plasmid pcDNA3.1(+) FAIM is then purified using Maxi Plasmid Purification Kit (Qiagen, Hilden, Germany) and its concentration quantified for transfection into CHO IFN-γ.

In detail, cgFAIM with artificial kozak sequence and linker regions is created by using the 5'-PCR primer, 5'-

GAATTCGCCACCATGACAGATCTTGTAGC-3'(SEQ ID NO: 43) and the 3'-PCR primer, 5'-GAATTCGTGAACACATTTAATTACCA-3' (SEQ ID NO: 44). The underlined sequence consists of a EcoRI restriction site while the italicized sequence consists of an artificial kozak sequence to facilitate 'in-frame' expression of FAIM. The incorporated regions of cgFAIM are in bold.

The PCR reaction mix contained 1 µL of pCR2.1-TOPO cgFAIM template, 1× Reaction buffer, 200 µM of each dNTP, 2.0 mM MgCl$_2$, 1 µM of each primer and Taq DNA polymerase mix (Total 5 U). PCR conditions are: 94° C. for 5 min, followed by 60 cycles of 94° C. for 1 min, 44° C. for 1 min and 72° C. for 2 min and a final extension at 72° C. for 10 min.

The verified PCR product is then digested with EcoRI restriction enzyme at 37° C. for approximately 4 hours to create cgFAIM inserts with sticky ends for further ligation. Blank pcDNA3.1(+) vector (Invitrogen) is also digested with EcoRI restriction enzyme at 37° C. for approximately 4 hours. EcoRI digested cgFAIM insert is then ligated into EcoRI digested pcDNA3.1(+) by adding 12 µL of insert to 3 µL of vector, 2 µL of DNase-free water, 2 µL of 10× T4 DNA ligase buffer (Invitrogen) and 1 µL of T4 DNA ligase (3 U/µL) (Invitrogen). This ligation mixture is then incubated for approximately 16 hours at room temperature.

10 µL of the ligation mixture is then transformed into competent DH5αt bacterial cells for plasmid propagation. Positive transformants are selected for by culturing in LB agar plates with ampicillin for selection. Plasmid extraction is then carried out on various DH5α clones for sequencing to verify cgFAIM sequence inserted into pcDNA3.1(+) expression vector. The plasmid pcDNA3.1(+) cgFAIM from a verified clone is then purified using Maxi Plasmid Purification Kit (Qiagen, Hilden, Germany) and its concentration quantified for transfection into CHO IFN-γ.

Example 9

Cricetulus griseus FADD Dominant Negative Expression Vector Construction

An artificial FADD dominant negative (FADD DN) fragment with kozak sequence is created by using the 5'-PCR primer, 5'-GATATCGGATCCGCCACC-ATGGCCTTTGA-CATTGTATGCGACAATGTGGGG-3' (SEQ ID NO: 11) and the 3'-PCR primer, 5'-CCCGGG-CTCGAGTGCCTCCC-TTCCACCAGGTCAG-3' (SEQ ID NO: 12). The underlined sequence consists of a BamHI and XhoI restriction site respectively while the italicized sequence consists of an artificial kozak and start codon to facilitate 'in frame' expression of cgFADD Dominant Negative. The incorporated coding regions of cgFADD are in bold.

The PCR reaction mix contains 1 µL of cDNA template, 1× Reaction buffer, 200 µM of each dNTP, 1.5 mM MgCl$_2$, 1 µM of each primer and Taq DNA polymerase mix (Total 5 U). The partial FADD sequence subcloned in pCR®-TOPO® is used as the template. PCR conditions are: 94° C. for 5 min, followed by 31 cycles of 94° C. for 1 min, 50° C. for 1 min and 72° C. for 2 min and a final extension at 72° C. for 10 min.

The verified PCR product is then digested with BamHI and XhoI restriction enzymes at 37° C. for approximately 4 hours to create cgFADD DN inserts with sticky ends for further ligation. Blank pcDNA3.1(+) vector (Invitrogen) is also digested with BamHI and XhoI restriction enzyme at 37° C. for approximately 4 hours. BamHI/XhoI digested cgFADD DN insert is then ligated into BamHI/XhoI digested pcDNA3.1(+) by adding 12 µL of insert to 3 µL of vector, 2 µL of Dnase-free water, 2 µL of 10× T4 DNA ligase buffer (Invitrogen) and 1 µL of T4 DNA ligase (3 U/µL) (Invitrogen). This ligation mixture is then incubated for approximately 16 hours at room temperature.

10 µL of the ligation mixture is then transformed into competent DH5α bacterial cells for plasmid propagation. Positive transformants are selected for by culturing in LB agar plates with ampicillin for selection. Plasmid extraction is then carried out on various DH5αt clones for sequencing to verify cgFADD DN sequence inserted into pcDNA3.1(+) expression vector. The plasmid pcDNA3.1(+) FADD Dominant Negative from a verified clone is then purified using Maxi Plasmid Purification Kit (Qiagen, Hilden, Germany) and its concentration quantified for transfection into CHO IFN-γ.

Example 10

Cricetulus griseus PDCD6 Suppression Vector Construction

An oligo insert is designed based on the obtained cgPDCD6 sequence. The oligo insert design is compared to a genomic database using BLAST to eliminate any significant homology to other genes. The 5' oligo insert, 5'-GATCCCGT-GAGCTTCAGCAAGCATTATTCAA-GAGATAATGCTTGCTGAAGC-TCATTTTTTGGAAA-3' (SEQ ID NO: 13) is annealed to the 3' oligo insert, 5'-AGCTTTTCCAAAAAATGAGCTTCAG-CAAGCATTATCTCTTGAATAATGCTTGCTG AAGCT-CACG-3' (SEQ ID NO: 14) is then synthesized and then ligated into HindIII/BglII digested pSUPER.neo vector (OligoEngine, Seattle, Wash.).

4 µL of annealed oligo insert is added to 3 µL of HindIII/BglII digested pSUPER.neo, 13 µL of Dnase-free water, 2 µL of 10× T4 DNA ligase buffer (Invitrogen) and 1 µL of T4 DNA ligase (3 U/µL) (Invitrogen). This ligation mixture is then incubated for approximately 16 hours at room temperature.

10 µL of the ligation mixture is then transformed into competent DH5αc bacterial cells for plasmid propagation. Positive transformants are selected for by culturing in LB agar plates with ampicillin for selection. Plasmid extraction is then carried out on various DH5α clones for sequencing to verify cgPDCD6 siRNA sequence inserted into pSUPER.neo expression vector. The plasmid pSUPER.neo cgPDCD6 siRNA from a verified clone is then purified using Maxi Plasmid Purification Kit (Qiagen, Hilden, Germany) and its concentration quantified for transfection into CHO IFN-γ.

Example 11

Cricetulus griseus Requiem Suppression Vector Construction

Oligo insert is designed based on obtained cgRequiem sequence. The 5' oligo insert, 5'-GATCCCGCGGATCCT-TGAACCTGATTTCAAGAGAATCAGGT-TCAAGGATCCGC-TTTTTTGGAAA-3' (SEQ ID NO: 15) is annealed to the 3' oligo insert, 5'-AGCTTTTC-CAAAAAAGCGGATCCTTGAACCTGAT-TCTCTTGAAATCAGGTTCAAG GATCCGCGG-3' (SEQ ID NO: 16) and then ligated into HindIII and BglII digested pSUPER.neo vector (OligoEngine, Seattle, Wash.).

4 µL of annealed oligo insert is added to 3 µL of HindIII/BglII digested pSUPER.neo, 13 µL of Dnase-free water, 2 µL of 10× T4 DNA ligase buffer (Invitrogen) and 1 µL of T4

DNA ligase (3 U/μL) (Invitrogen). This ligation mixture is then incubated for approximately 16 hours at room temperature.

10 μL of the ligation mixture is then transformed into competent DH5α bacterial cells for plasmid propagation. Positive transformants are selected for by culturing in LB agar plates with ampicillin for selection. Plasmid extraction is then carried out on various DH5α clones for sequencing to verify cgRequiem siRNA sequence inserted into pSUPER-.neo expression vector. The plasmid pSUPER.neo cgRequiem siRNA from a verified clone is then purified using Maxi Plasmid Purification Kit (Qiagen, Hilden, Germany) and its concentration quantified for transfection into CHO IFN-γ.

Example 12

Transfection & Selection

Transfection is carried out using Lipofectamine reagent (Invitrogen). Cells are grown overnight in 6-well plates with 0.5 million cells per well and transfected with approximately 1 μg of linearized plasmid per well the next day. The Lipofectamine-DNA complex is prepared according to manufacturer's instructions in a 3:1 Lipofectamine (μL) to DNA (μg) ratio.

To generate stable cells, the cells are grown for 24 hr before the media is changed to selection media containing 1000 μg/mL of Geneticin. The cells are maintained in selection media for 4 weeks where the untransfected cells in the selection media died within a week.

Example 12A

Stably Integrated Single Cell Clones

Stably integrated single cell clones are obtained by serial dilution of cells into 96-well plates such that there would only be one cell in each well. Wells are checked under light microscope and those that only contain a single cell are marked. Single clones are then expanded into 24-well plates followed by 6 well plates before going into shake flasks culture.

Example 12B

Batch and Fed-Batch Culture

An initial working volume of 4.0 L of culture media is inoculated with a seeding density of $2.5 \times 10^5$ cells/mL in a 5.0 L bioreactor (B. Braun, Melsungen, Germany). Batch cultures are carried out using glucose/glutamine-free HyQ CHO MPS media (Hyclone, Logan, Utah) supplemented with 20 mM glucose and 4 mM glutamine while fed-batch cultures are supplemented with 4 mM glucose and 0.5 mM glutamine. Dissolved oxygen concentration is maintained at 50% air saturation and culture pH is maintained at 7.15 using intermittent $CO_2$ addition to the gas mix and/or 7.5% (w/v) $NaHCO_3$ solution (Sigma).

Fed-batch operation is performed using a modified online dynamic feeding strategy (Lee et al., 2003). Online monitoring of concentrations of the relevant controlled nutrient level are conducted every 1.5 hr using an automated aseptic online sampling loop. Basal feed media for fed-batch cultures is prepared from a custom formulated 10× calcium-free, glucose-free and glutamine-free DMEM/F12 with 1× salts (Hyclone) supplemented with 10 g/L of soybean protein hydrolysate, Hysoy (Quest International, Hoffman Estate, Ill.), 10 mL/L of chemically defined lipids (Gibco BRL, Grand Island, N.Y.), 1 mg/L of d-biotin (Sigma), 2 mM L-aspartic acid, 2 mM L-asparagine, 4 mM L-cysteine, 1 mM L-glutamic acid, 1 mM L-methionine and 5 mM L-serine (Sigma).

The basal feed media is further supplemented with 100 mM of glutamine (Sigma) and 500 mM of glucose (Sigma). Every 1.5 hr, an automated on-line measurement of residual glutamine concentrations would be taken. If residual glutamine concentration falls below setpoint control concentrations, feed injections would be effected with feed media to raise culture glutamine concentrations to 0.3 mM.

Example 13

Gene Expression Quantification using Real-Time PCR

Approximately 10 million cells are collected from stable cells and total RNA is extracted using TRIZOL™ reagent (Invitrogen). RNA Samples are then quantified using GENEQUANT™ Pro RNA/DNA Calculator (Amersham Biosciences, Piscataway, N.J.). RNA quality is assessed using the absorbance ratio of 260 nm to 280 nm, where a ratio of 1.8 and above is considered as RNA sample of sufficient purity.

Quantitative real time PCR is used to ascertain the relative over-expression or suppression of gene of interest after transfection experiments. In order to generate standard curves of transcript copy, quantified pCR®-TOPO® (Invitrogen) plasmids containing either FAIM, FADD, PDCD6 or Requiem are serially diluted and used for quantitative real time PCR.

Quantitative real time PCR for FAIM transcripts is carried out using 5'-primer 5'-TGGAGCTGCGAAAACCAAAG-3' (SEQ ID NO: 27) and 3'-primer 5'-AAACTCGCCTGCT-GTCTCCAT-3' (SEQ ID NO: 28). Quantitative real time PCR for FADD Dominant Negative transcripts is carried using 5'-primer 5'-GATATCGGATCCGCCACCATGG-3' (SEQ ID NO: 29) and 3'-primer 5'-TGCCTCCCTTCCACCAG-GT-CAG'3' (SEQ ID NO: 30). Quantitative real time PCR for PDCD6 transcripts is carried out using 5'-primer 5'-CAGCGGGTTGATAAAGACAGG-3' (SEQ ID NO: 31) and 3'-primer 5'-GCCAGCCTTG-TTTTCTCGG-3' (SEQ ID NO: 32). Quantitative real time PCR for Requiem transcripts is carried out using 5'-primers, 5'-TGGAGTAGCCCAGAG-CAATTG-3' (SEQ ID NO: 33) and 3'-primer, 5'-TC-GACGCTTTTTACGCCAG-3' (SEQ ID NO: 34).

Each sample is then normalized against β-actin transcript expression. Quantitative real time PCR for β-actin transcripts is carried out using 5'-primer 5'-AGCTGAGAGGGAAAT-TGTGCG-3' (SEQ ID NO: 35) and 3'-primer 5'-GCAACGG-AACCGCTCATT-3' (SEQ ID NO: 36). Finally, normalized quantitative gene expression in transfected cells is divided by normalized quantitative gene expression in null vector transfected cells to give normalized relative gene expression.

Example 14

Apoptosis Assay

An Ethidium Bromide/Acridine Orange Assay is used to classify cells in samples collected into apoptotic or non-apoptotic populations. Stock solutions of 100 μg/mL of Ethidium Bromide (Sigma) and Acridine orange (Sigma) are prepared in PBS solution (Sigma).

Approximately $1 \times 10^6$ cells are sampled from samples and resuspended in 100 μL of 1:1 Ethidium Bromide: Acridine Orange stock solution and incubated for 5 minutes at room temperature. Samples are then loaded onto glass slides and approximately 400 cells are examined under fluorescence microscopy.

Cells with apoptotic morphology of nuclear condensation are then classified accordingly. In addition to morphological analysis, caspases 2, 3, 8 and 9 activity is measured using BD ApoAlert® Caspase Assay Plates (BD Biosciences Clontech, CA) according to the manufacturer's protocol. Activation of caspases is considered as biochemical hallmarks of apoptosis.

Example 15

IFN-γ Quantification

IFN-γ concentrations of serially diluted supernatant samples are analyzed using an enzyme-linked immunosorbent (ELISA) assay (HyCult Biotechnology, Uden, Netherlands). Samples that had the highest IFN-γ concentrations during high viability (>95%) and during low viability (70-80%), are sent for immunoaffinity purification and further N-glycosylation characterization.

Example 16

Real Time PCR for Gene Expression Detection

To determine the expression of targeted genes in cells, quantitative real-time PCR is carried out. Real-time PCR is considered as a sensitive method for the detection of transcript levels.

Gene expression analysis shows that cells transfected with pcDNA3.1(+) Faim over-express FAIM by 3 times more than cells transfected with pcDNA3.1(+) blank (FIG. 1). Cells transfected with pcDNA3.1(+) FADD Dominant Negative, over-express FADD Dominant negative by up to 4 times (FIG. 1). The data in FIG. 1 also shows that siRNA can be used effectively to suppress gene expression. Transfection with pSUPER PDCD6 siRNA results in suppression of PDCD6 expression by approximately 60% while pSUPER Requiem siRNA is able to suppress Requiem expression by up to 70% (FIG. 1).

Example 17

Apoptosis Resistance Conferred by Gene Targeting of *Cricetulus Griseus* FAIM

Cells are transfected with a FAIM expression vector (Example 8) and a blank vector as control, and resistance to apoptosis assayed.

Figure 2A:
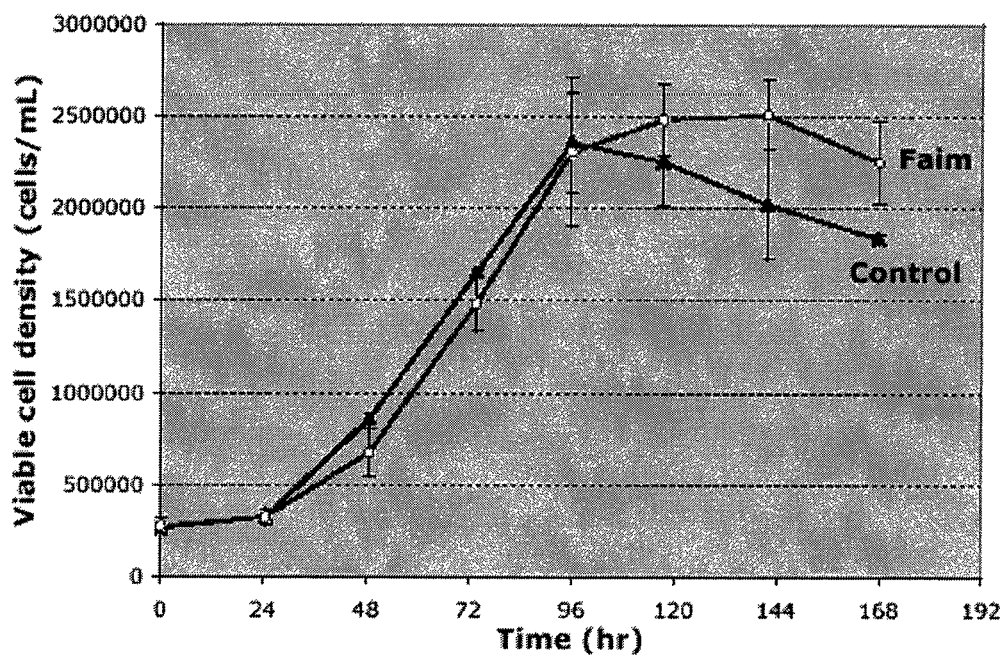
FIGS. 2A-2D are graphs showing the growth kinetics of CHO IFN-γ cells over-expressing FAIM.
Figure 2B:
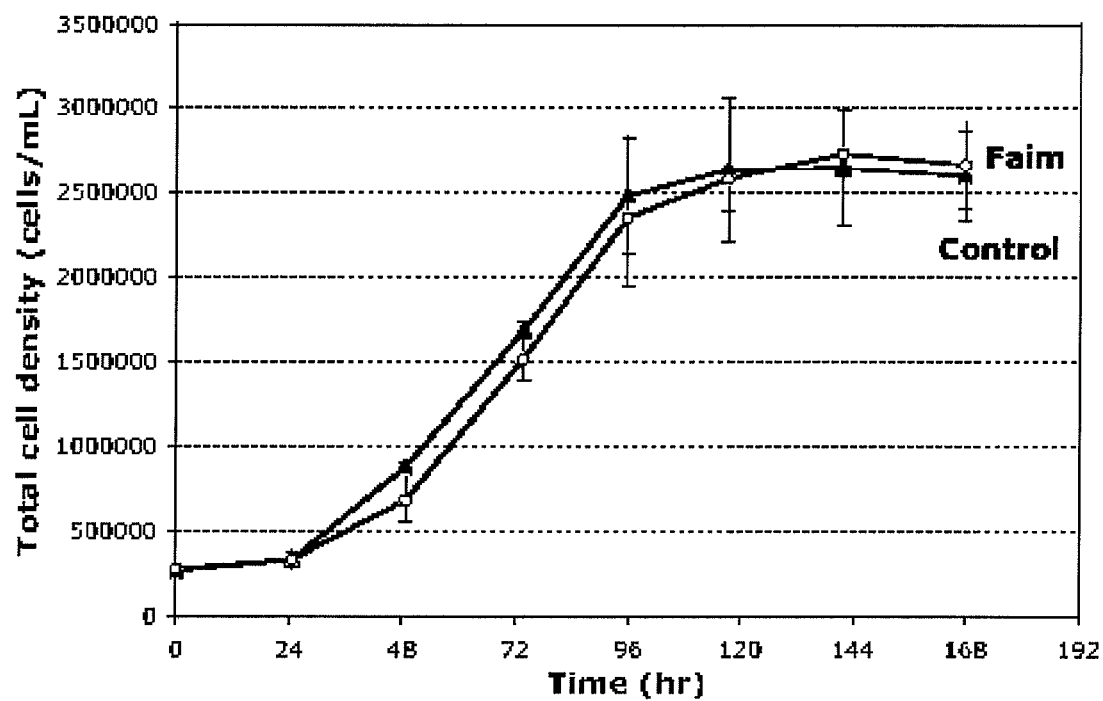
Figure 2C:
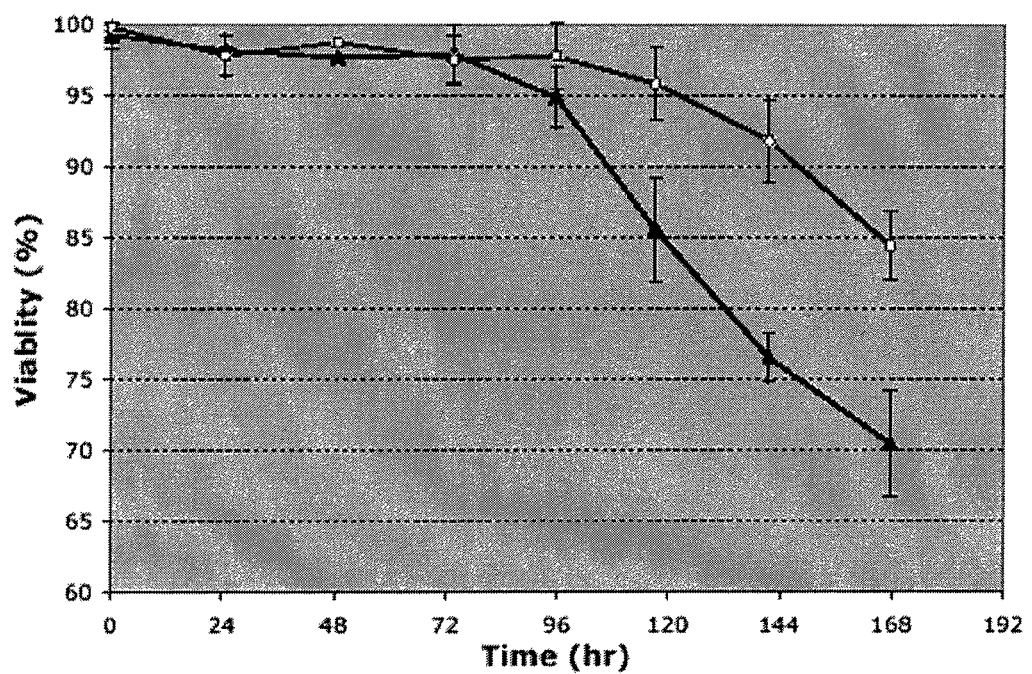
Figure 2D:
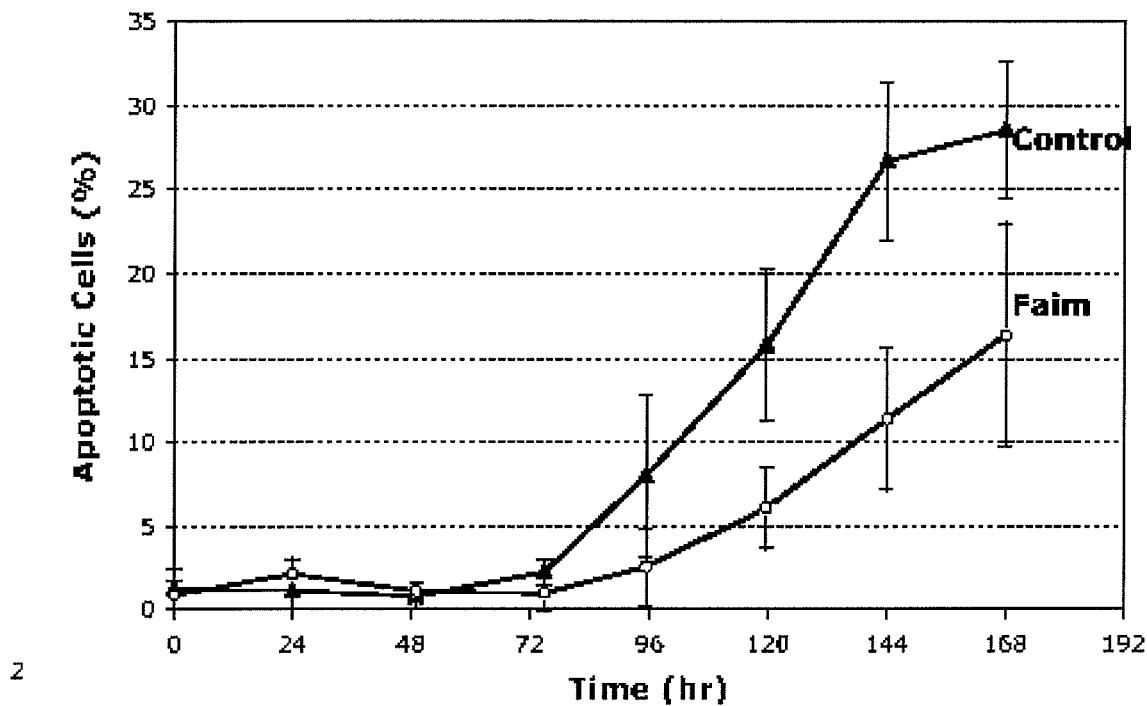
Figure 6A:
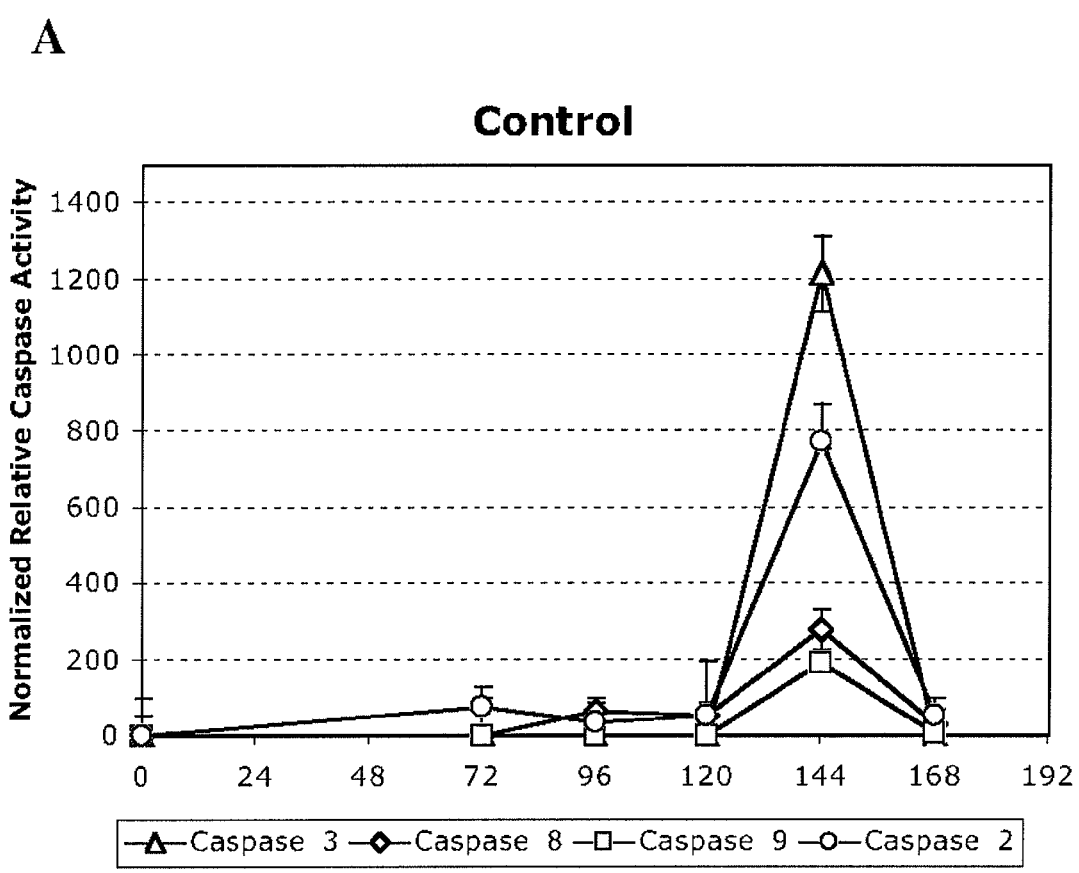
FIGS. 6A-6E are graphs showing the activity of Caspases 2, 3, 8 and 9 in CHO cell culture.
Figure 6B:
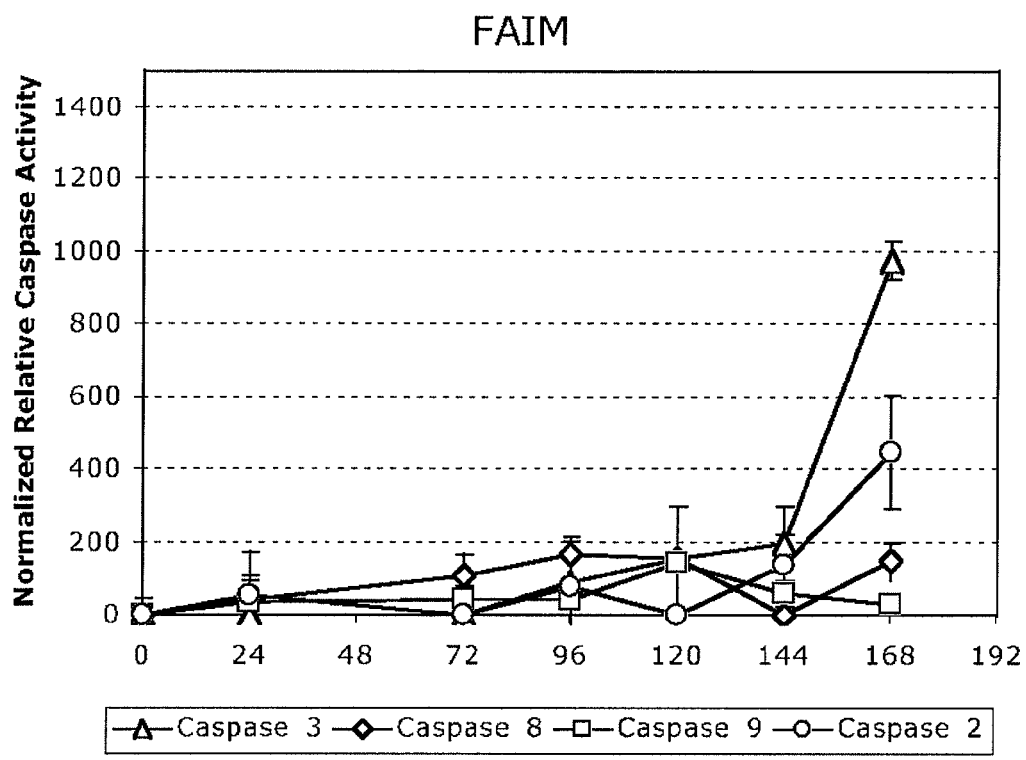

Compared to cells transfected with just the blank vector, cells over-expressing FAIM are able to maintain high viable cell density for a longer period of time (FIG. 2A). Cells with FAIM over-expression also show a significant extension of viability by at least 24 hours before viability started to drop below 95% (FIG. 2B). The percentage of apoptotic cells is also significantly lower than that of control cells without FAIM over-expression (FIG. 2D). Increase in caspase 2 and 3 activity is also delayed by approximately 24 hours compared to control cells (FIG. 6B). This showed that FAIM over-expression could be very effective in suppressing apoptosis in cell culture processes.

Example 18

Apoptosis Resistance Conferred by Gene Targeting of *Cricetulus griseus* FADD

Cells are transfected with a FADD expression vector (Example 9) and a blank vector as control, and resistance to apoptosis assayed.

Figure 3A:
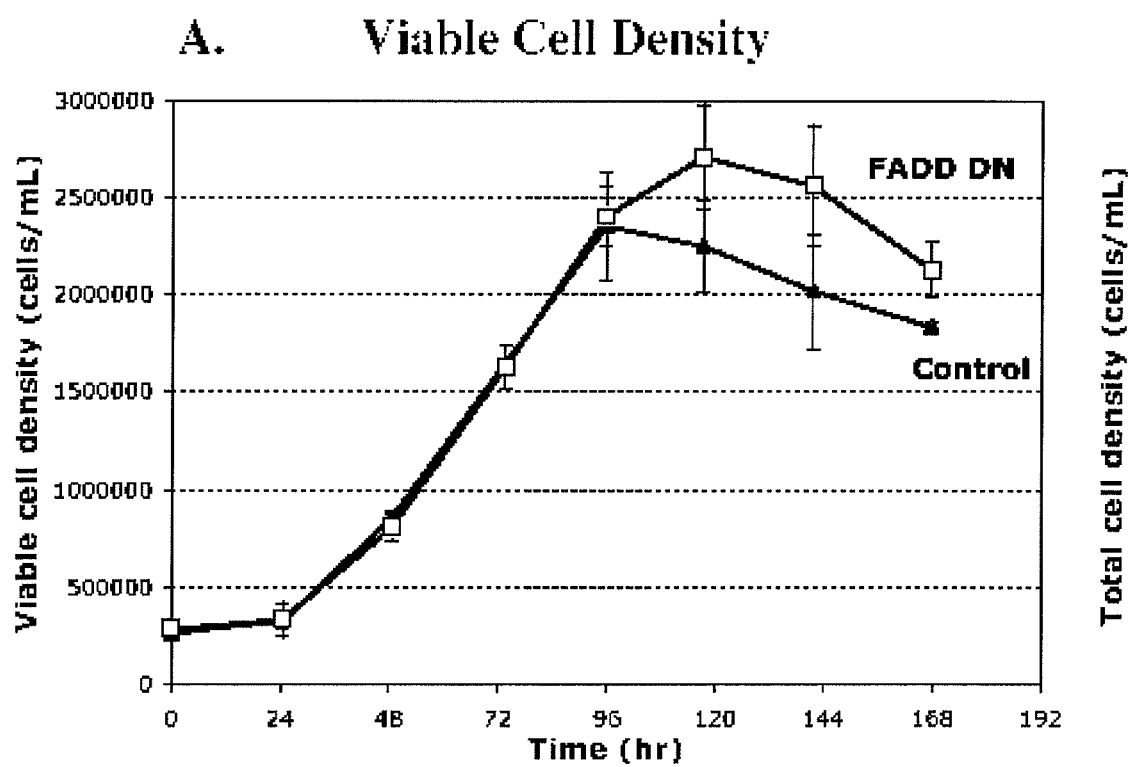
FIGS. 3A-3D are graphs showing the growth kinetics of CHO IFN-γ cells over-expressing FADD dominant negative.
Figure 3B:
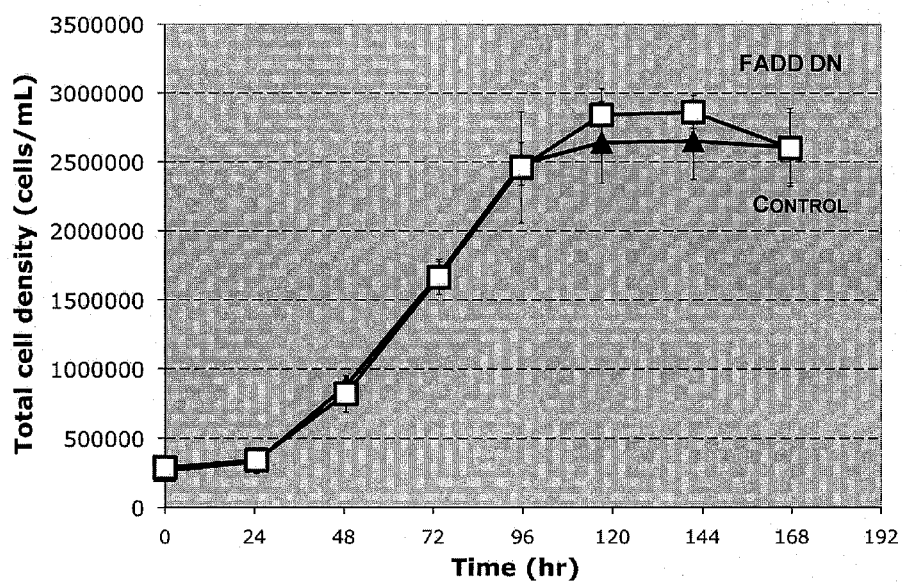
Figure 3C:
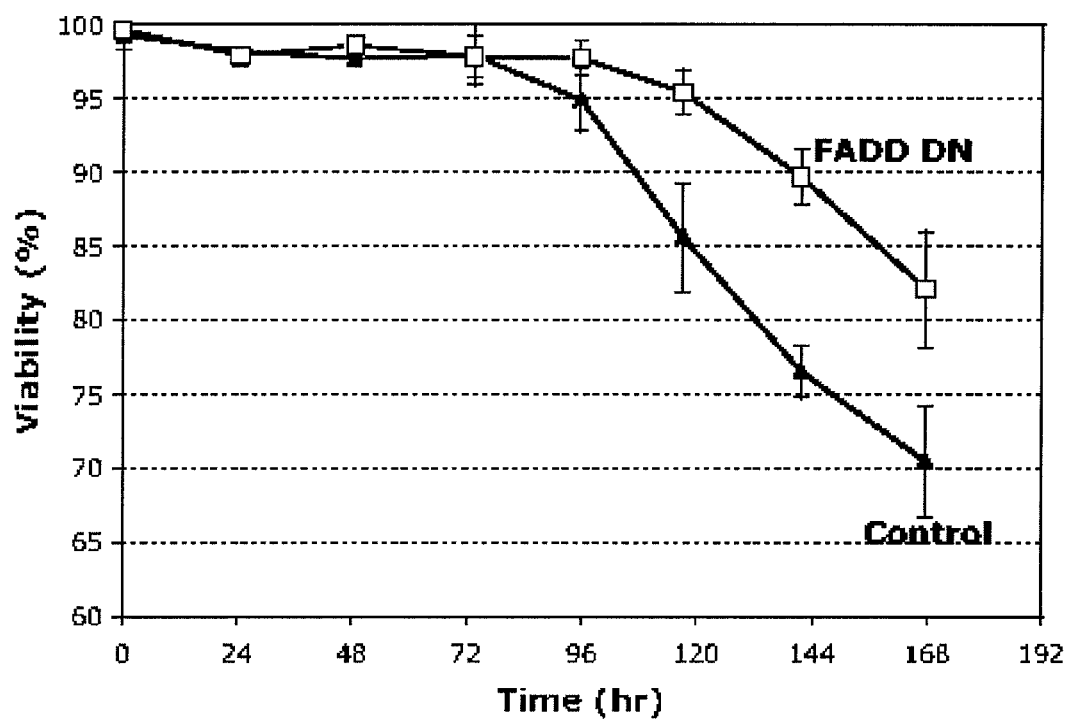
Figure 3D:
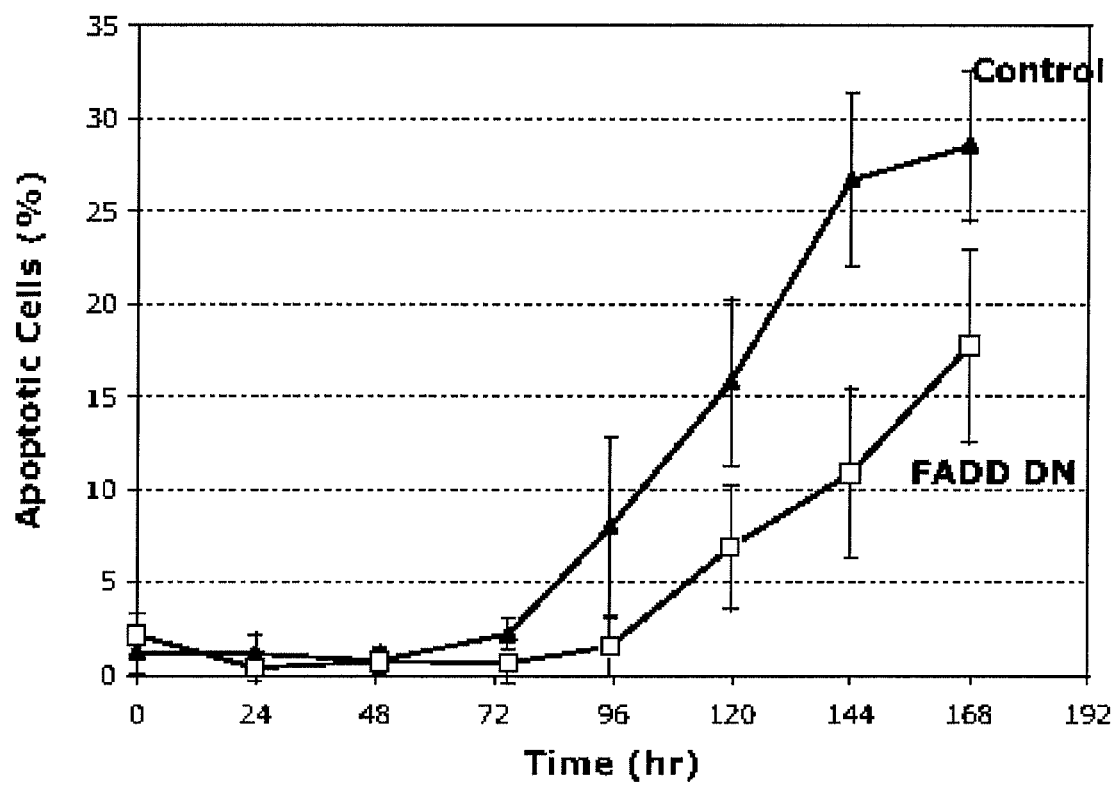
Figure 6C:
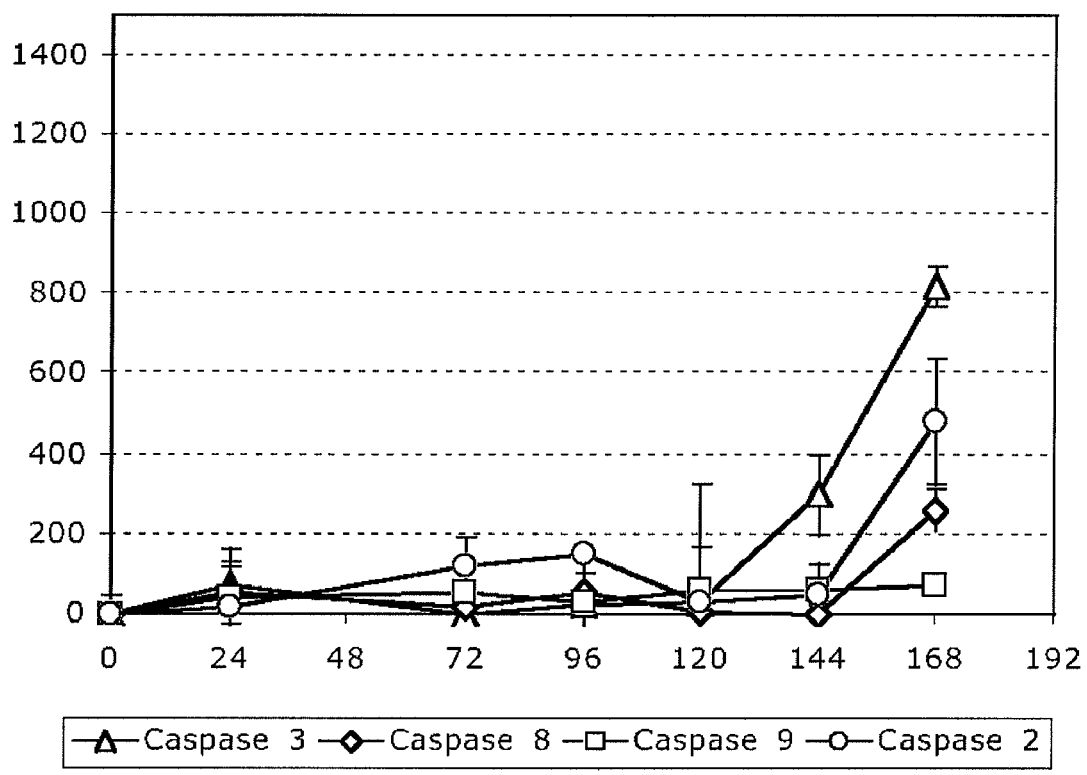

Compared to cells transfected with just the blank vector, cells over-expressing FADD dominant negative are able to maintain high viable cell density for a longer period of time (FIG. 3A). Cells with FADD dominant negative over-expression also show a significant extension of viability by around 24 hours before viability started to drop below 95% (FIG. 3B). The percentage of apoptotic cells is also significantly lower than that of control cells without FAIM over-expression (FIG. 3D). Increase in caspase 2, 3 and 8 activity is also delayed significantly (FIG. 6C). The data showed that caspase 2 and 8 activity only increase after 144 hr in culture while caspase 3 activity increase is suppressed significantly. This shows that the targeting of FADD signaling effectively suppresses apoptosis in cell culture processes.

Example 19

Apoptosis Resistance Conferred by Gene Targeting of *Cricetulus griseus* PDCD6

Cells are transfected with a PDCD6 expression vector (Example 10) and a blank vector as control, and resistance to apoptosis assayed.

Figure 4A:
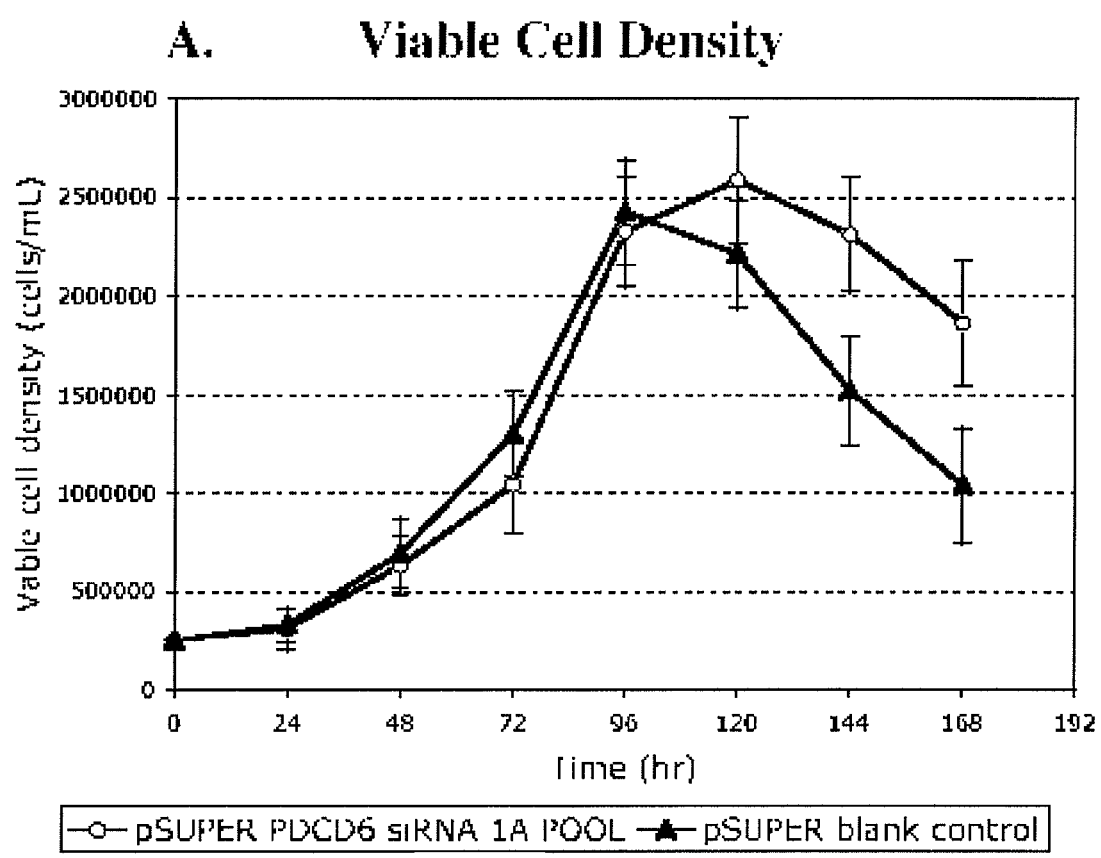
FIGS. 4A-4D are graphs showing the growth kinetics of CHO IFN-γ cells with PDCD6 suppression.
Figure 4B:
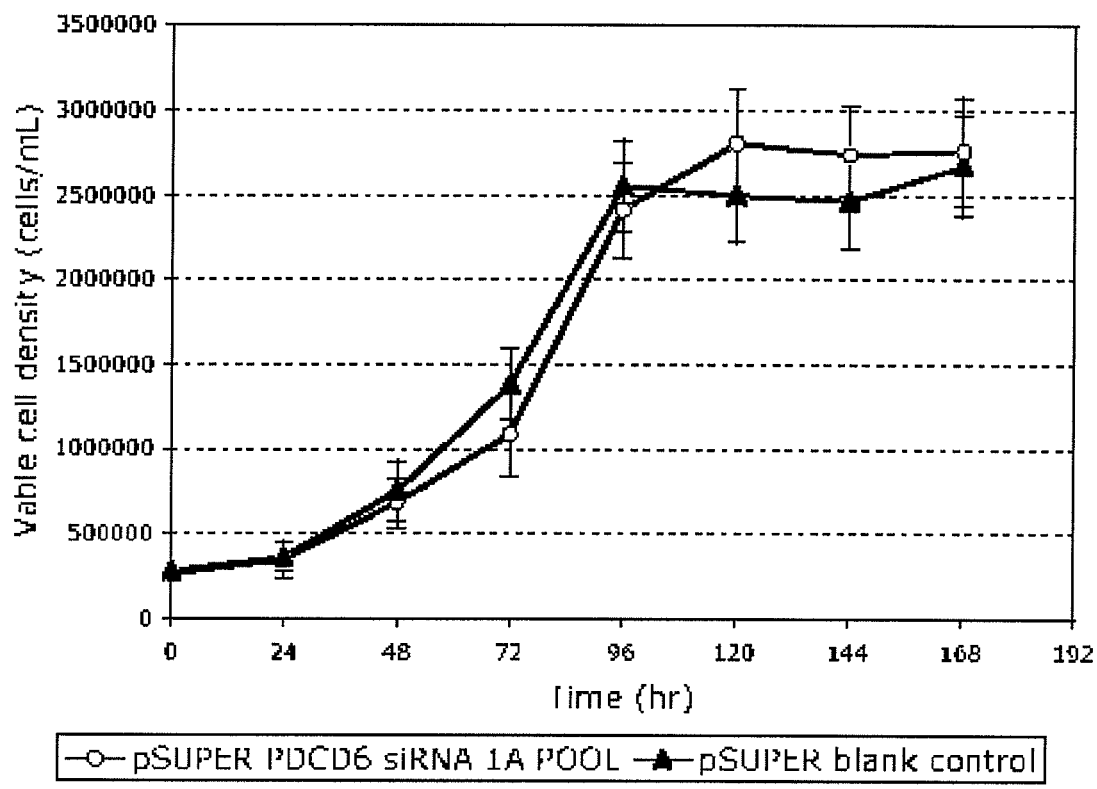
Figure 4C:
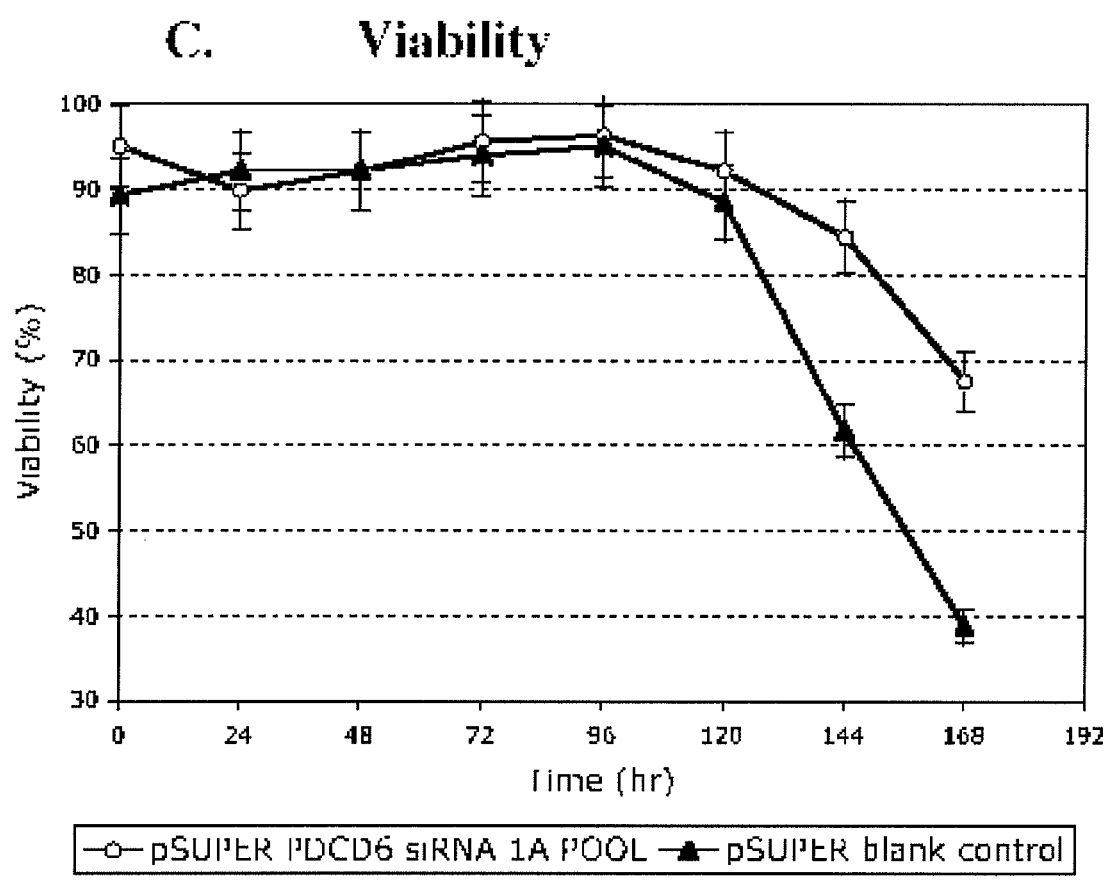
Figure 4D:
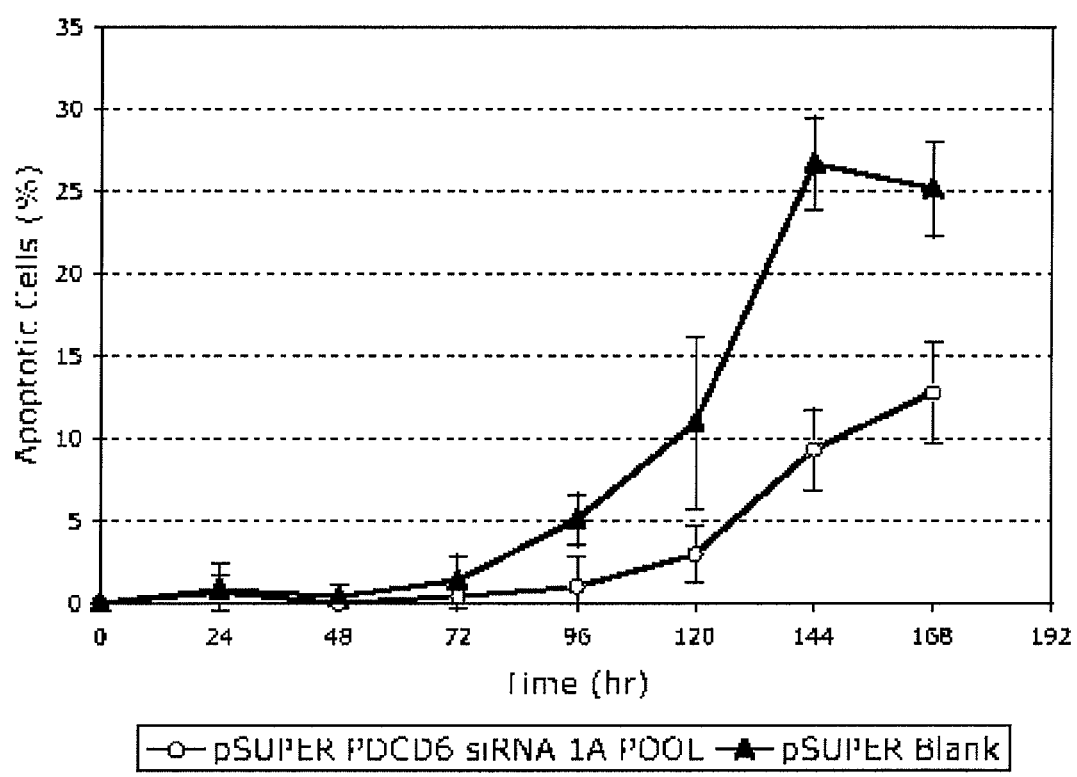
Figure 6D:
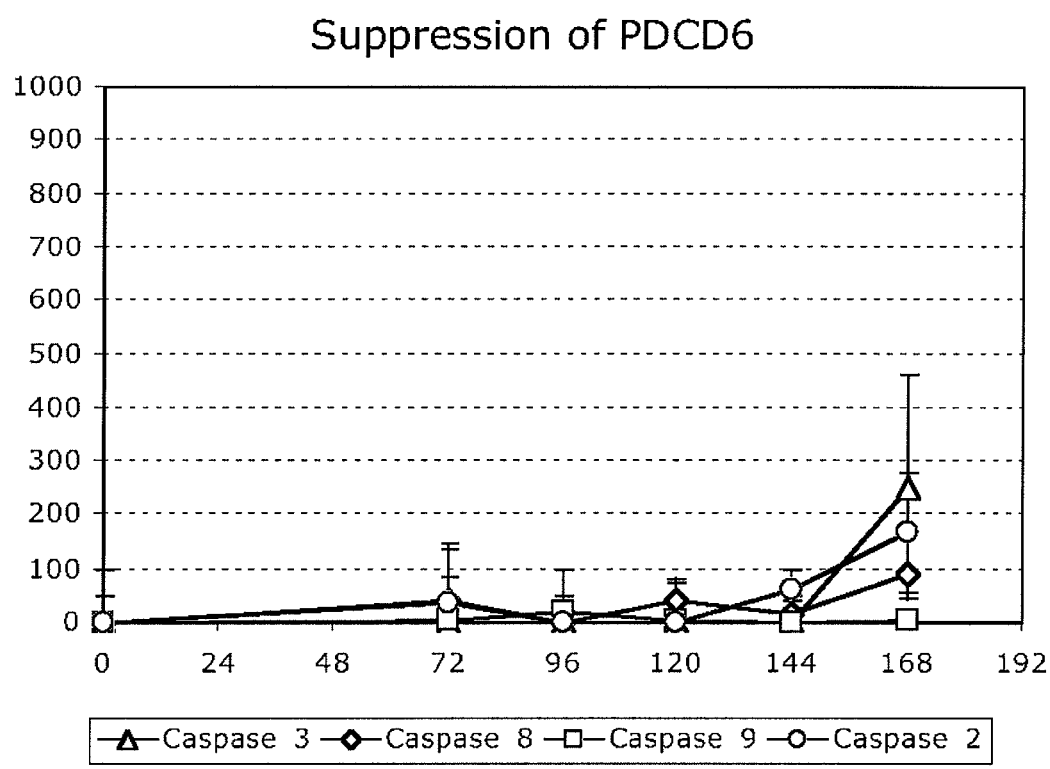

Compared to cells transfected with just the blank siRNA vector, cells with PDCD6 suppression are able to maintain high viable cell density for a longer period of time (FIG. 4A). Cells with PDCD6 suppression also show a significant decrease in the rate of viability loss (FIG. 4B). The percentage of apoptotic cells is also significantly lower than that of control cells without PDCD6 suppression (FIG. 4D). Increase in caspase 2, 3, 8 and 9 activity is also delayed significantly (FIG. 6D). The data showed that caspase 2, 3 and 8 activity only increase after 144 hr in culture while caspase 9 activity is always below the reference point. This show that the targeting of PDCD6 signalling could effectively suppress apoptosis in cell culture processes.

Example 20

Apoptosis Resistance Conferred by Gene Targeting of *Cricetulus griseus* Requiem Cells are transfected with a Requiem expression vector (Example 11) and a blank vector as control, and resistance to apoptosis assayed.

Figure 5A:
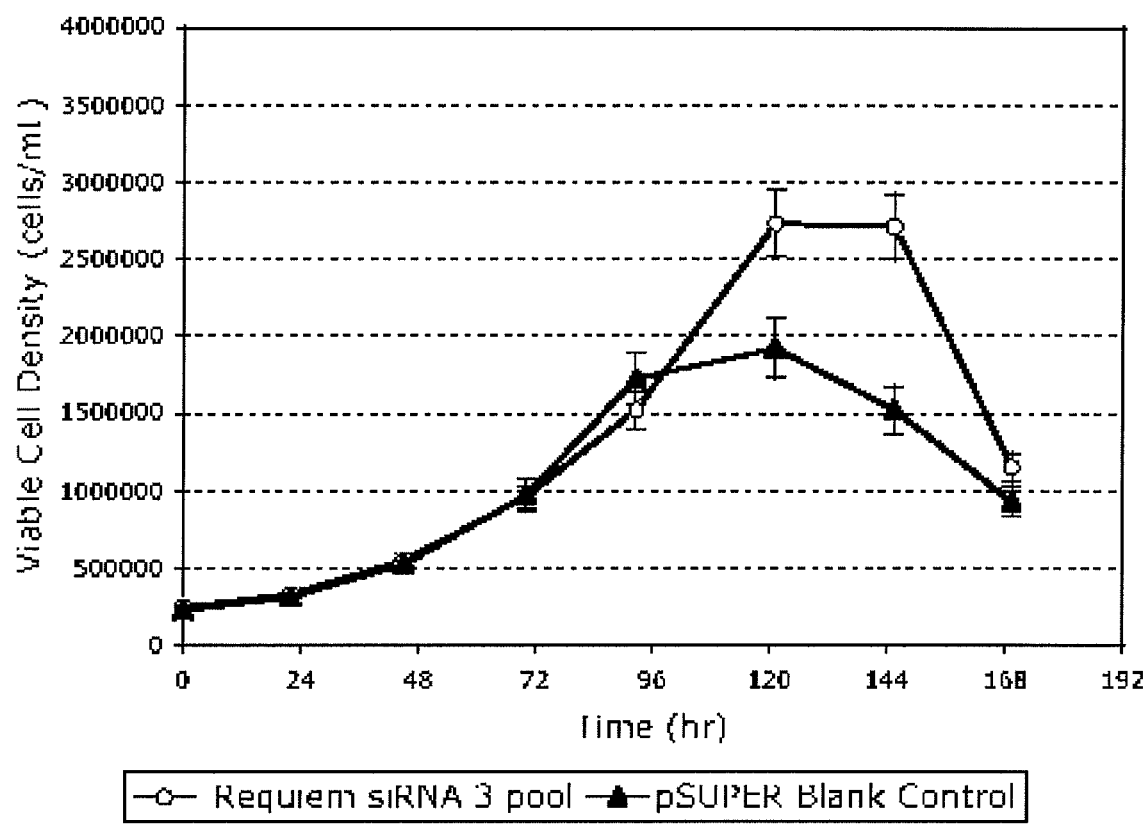
FIGS. 5A-5D are graphs showing the growth kinetics of CHO IFN-γ cells with Requiem suppression.
Figure 5B:
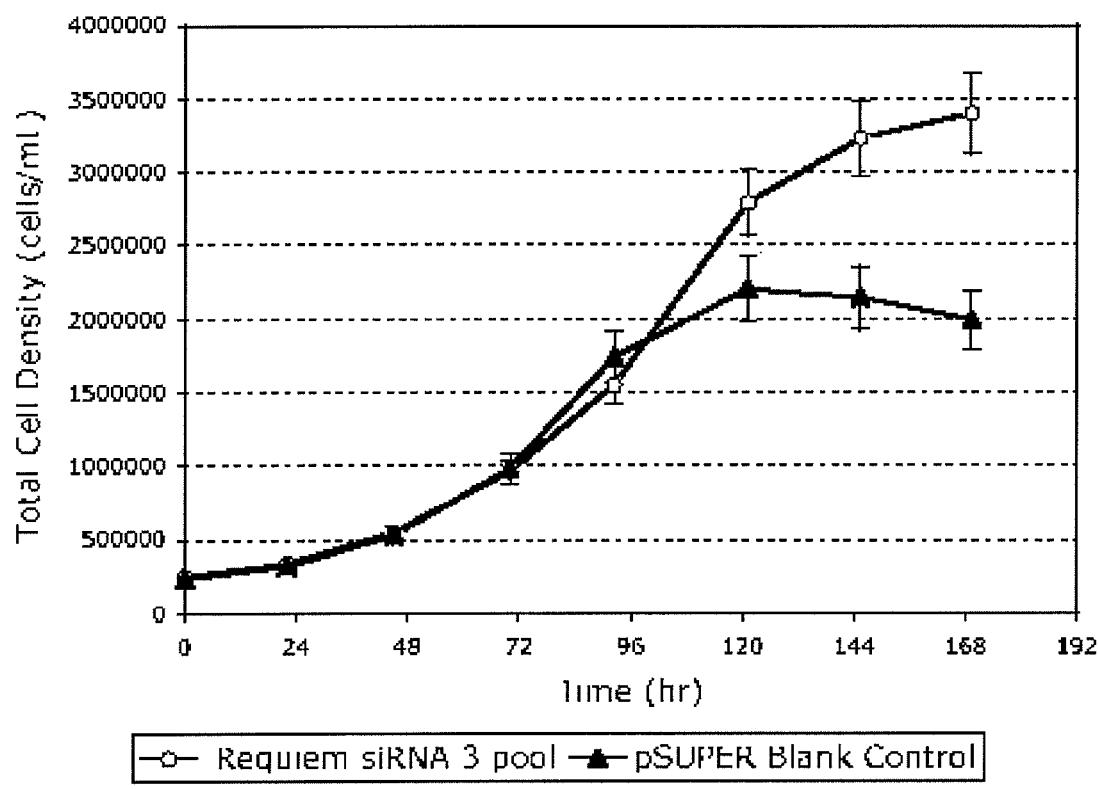
Figure 5C:
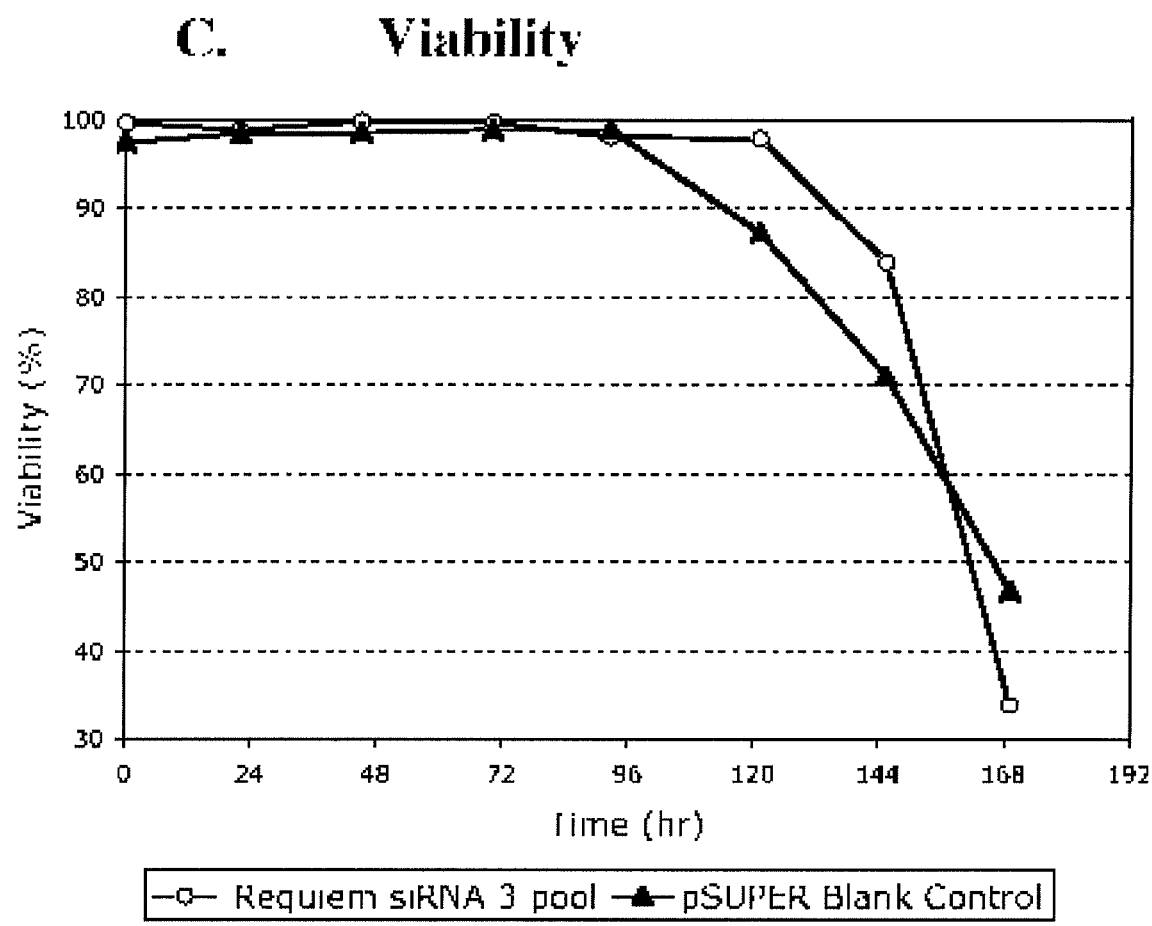
Figure 5D:
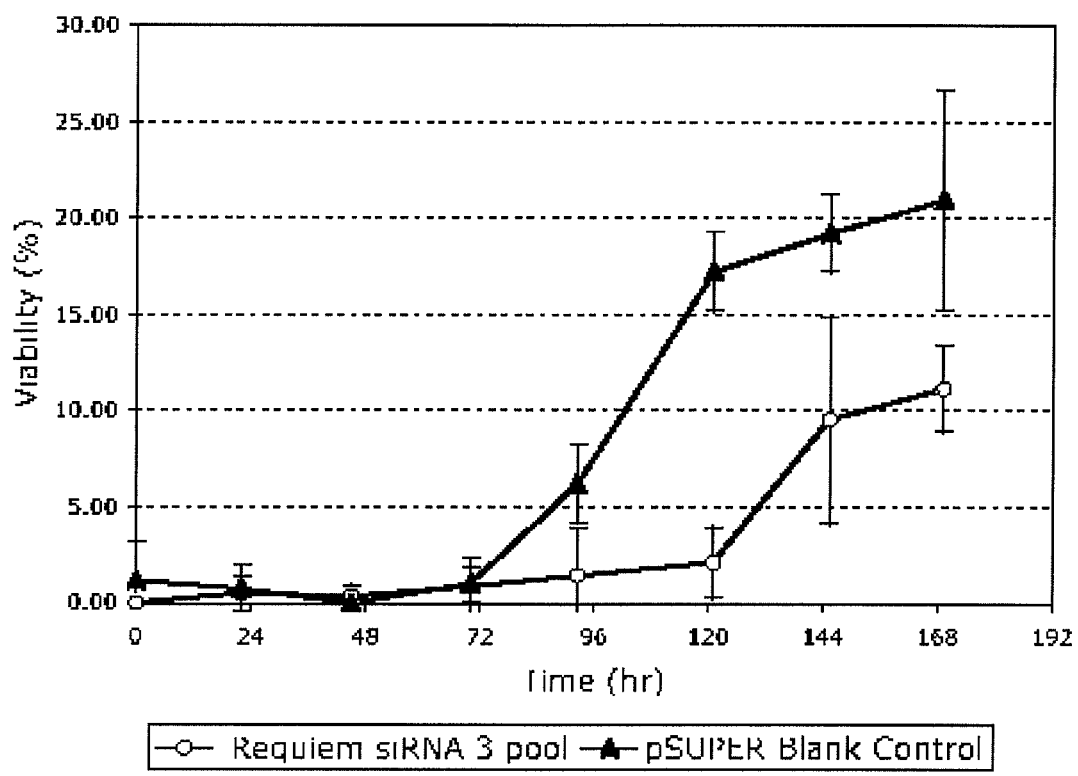
Figure 6E:
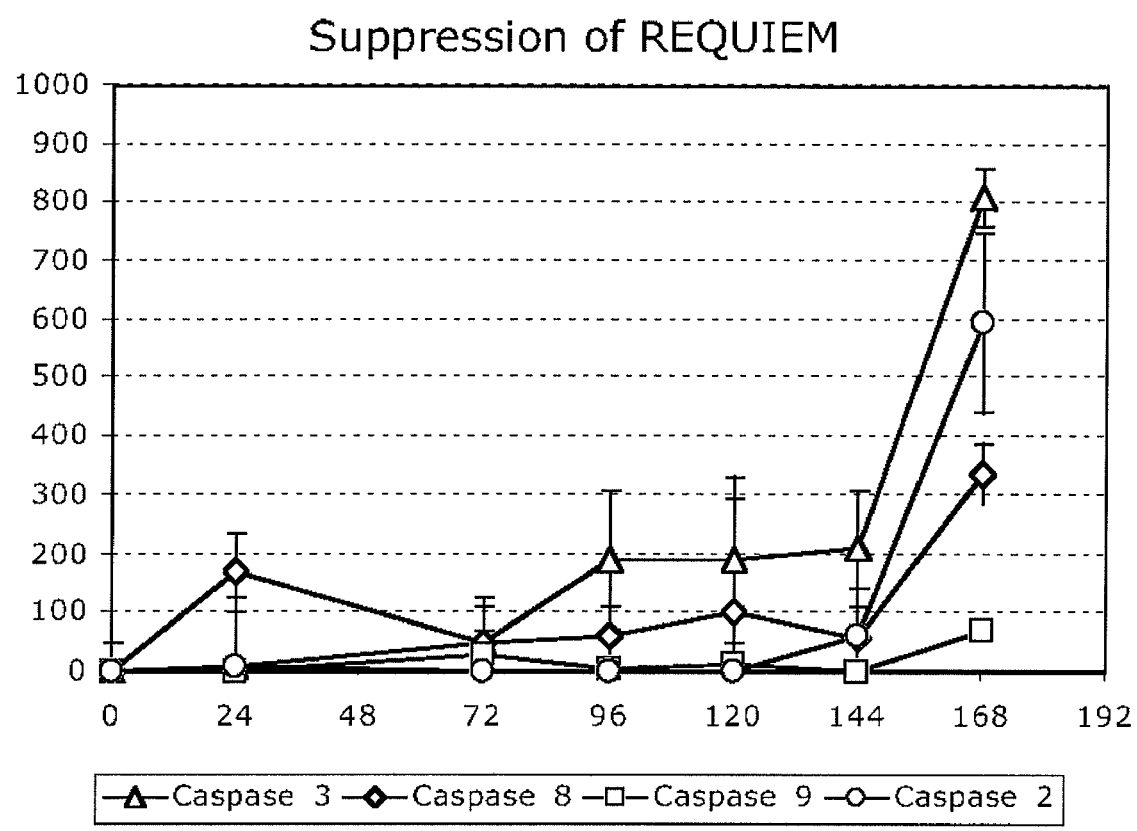

Compared to cells transfected with just the blank siRNA vector, cells with Requiem suppression is able to maintain higher viable cell density for a longer period of time (FIG. 5A). Cells with Requiem suppression also show a significant decrease in the rate of viability loss (FIG. 5B). The percentage of apoptotic cells is also significantly lower than that of control cells without Requiem suppression (FIG. 5D). Increase in caspase 2, 3, and 9 activity is also delayed significantly (FIG. 6E). The data showed that caspases activity are significantly lower than that of the control. This show that the targeting of Requiem signalling could effectively suppress apoptosis in cell culture processes.

Example 21

Improvement in Recombinant Protein Yield

FIG. 7 shows that gene targeting improves cell culture processes in terms of final product yield.

Figure 7A:
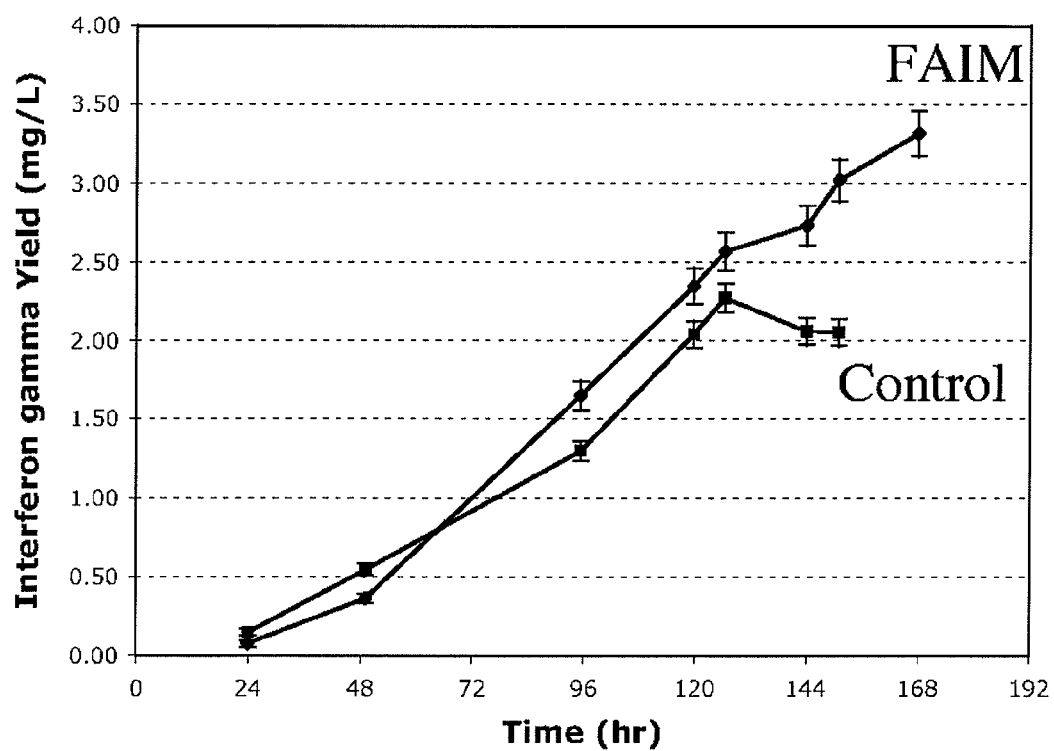
FIGS. 7A-7D are graphs showing Interferon-γ yields for transfected CHO IFN-γ cells.

Cells with FAIM over-expression allows for interferon gamma yields of up to 3.3 mg/L compared to the typical 2.3 mg/L yields seen in control cells (FIG. 7A).

Figure 7B:
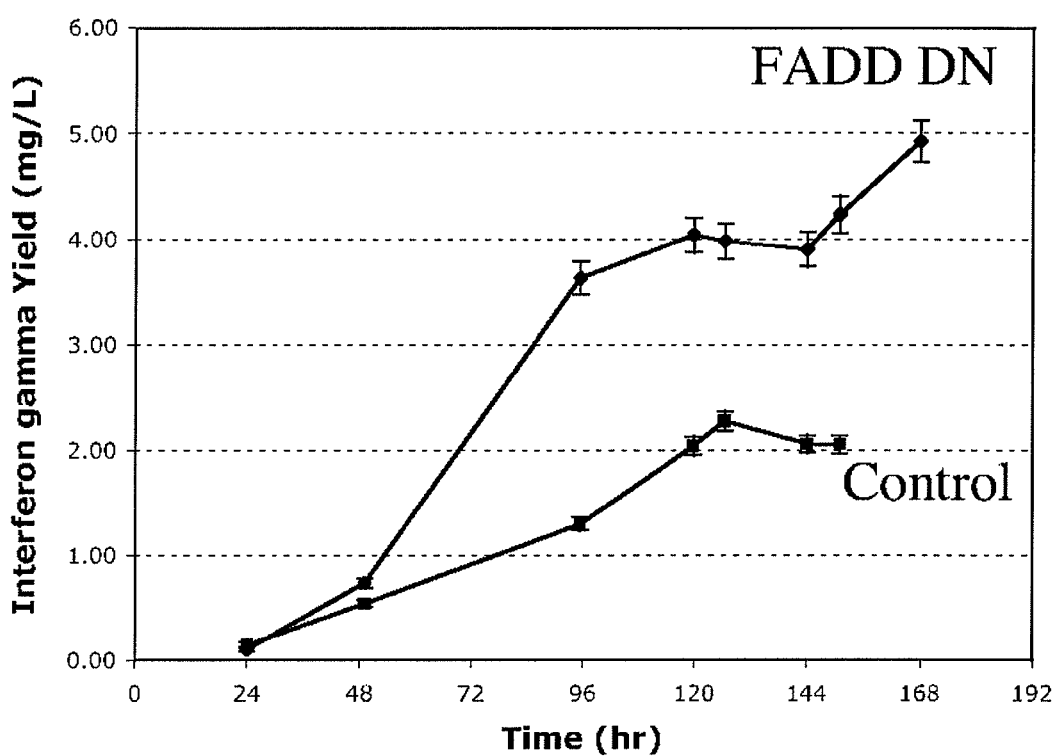
Figure 7C:
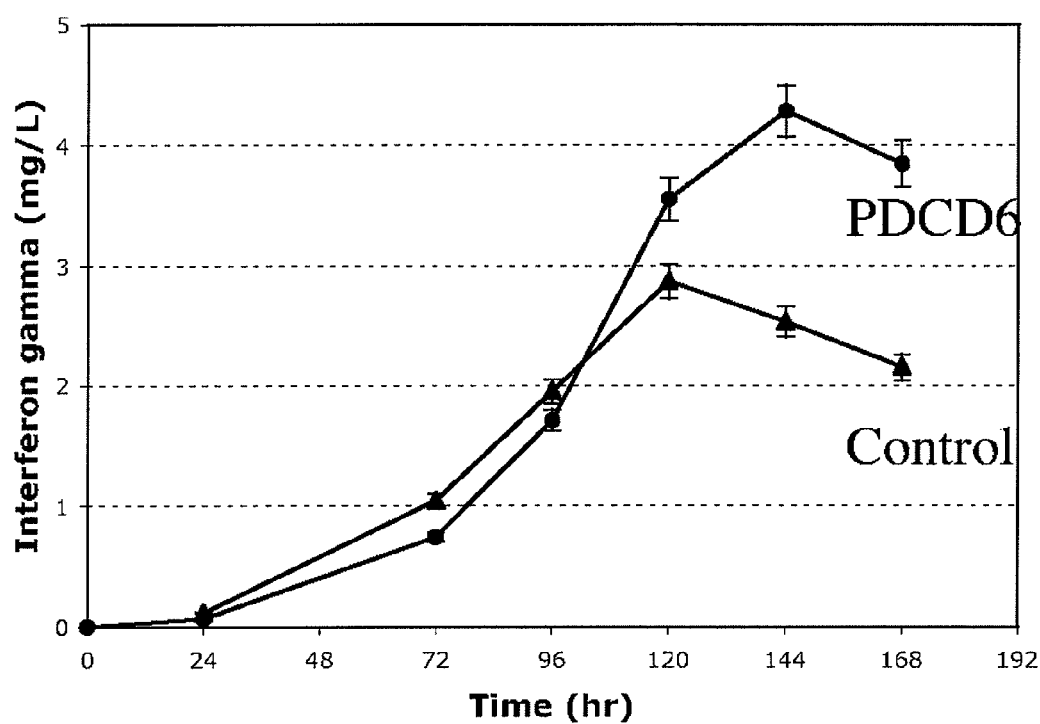
Figure 7D:
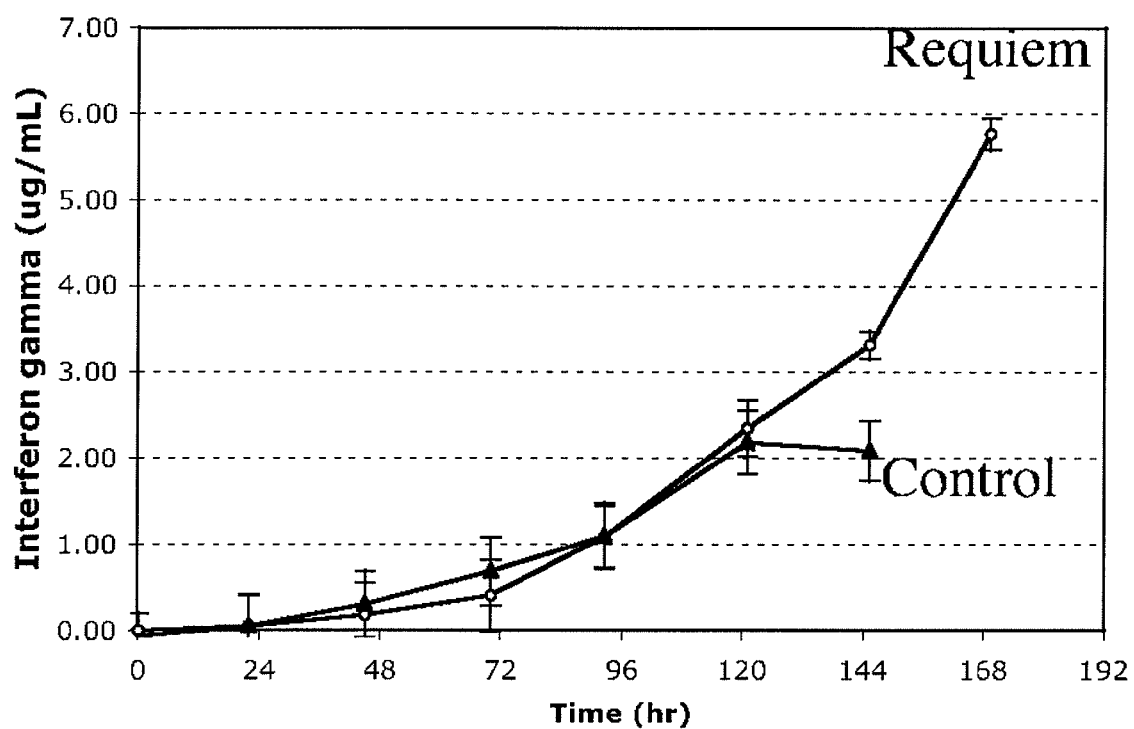

Targeting of FADD signalling even allows for interferon gamma yield concentration of up to 5.0 mg/L, representing more than 200% increase (FIG. 7B).

Suppression of PDCD6 and Requiem allows interferon gamma yield to improve to 4.2 and 5.8 mg/L respectively.

The increased robustness of engineered cells to apoptosis induction coupled with effective increase in final recombinant protein yield shows that gene targeting of FADD, FAIM, PDCD6 and Requiem are effective novel strategies for improving biotherapeutics production in cell culture systems.

Example 22

Enhanced Viable Culture Density in Addition to Viability Enhancement in Fed-Batch Culture Experiments are conducted to determine the ability of an engineered apoptosis resistant cell line to perform in fed-batch culture under the different batch and fed-batch stress/nutrient environment.

Figure 8A:
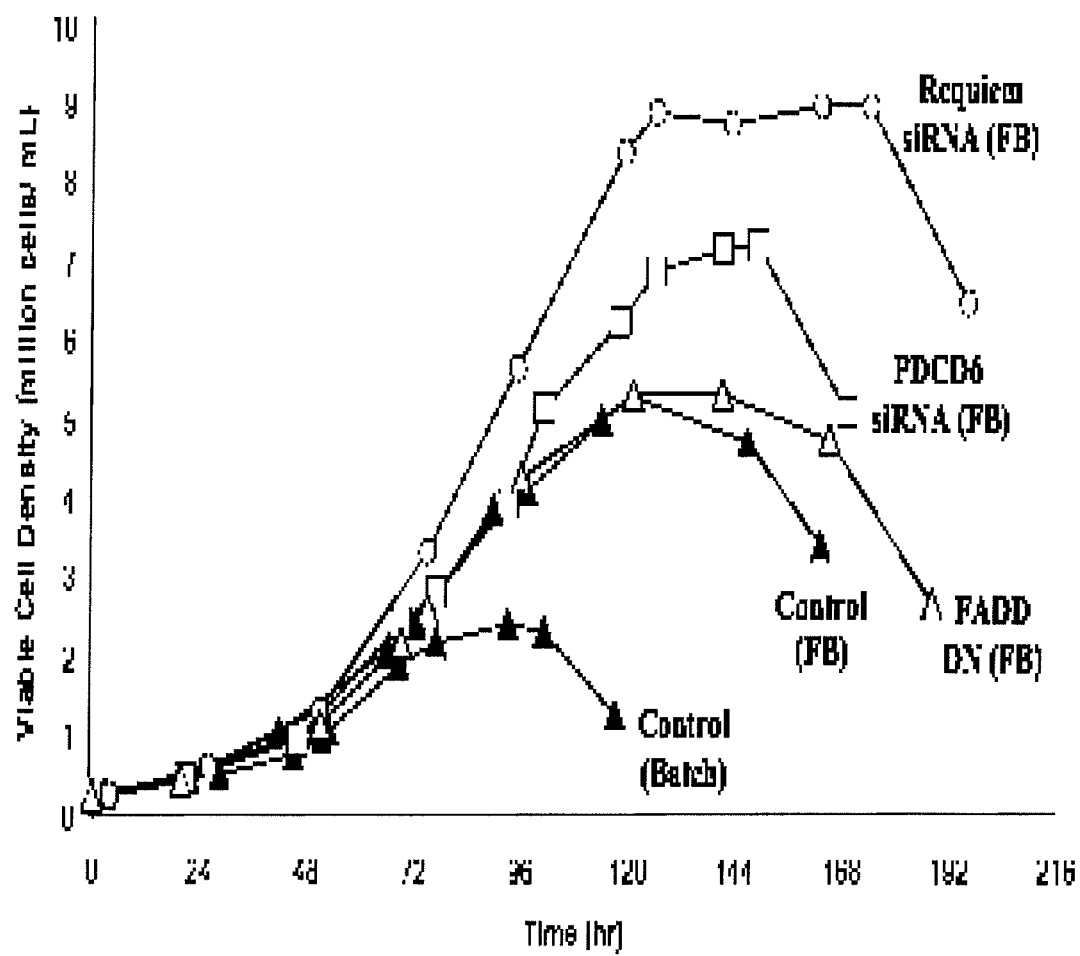
FIG. 8A shows viable cell densities of stable CHO IFN-γ clones with either Requiem or PDCD6 suppression or FADD DN or FAIM* overexpression in fed-batch cultures. (Data presented are the averages of two duplicate experiments).
Figure 8B:
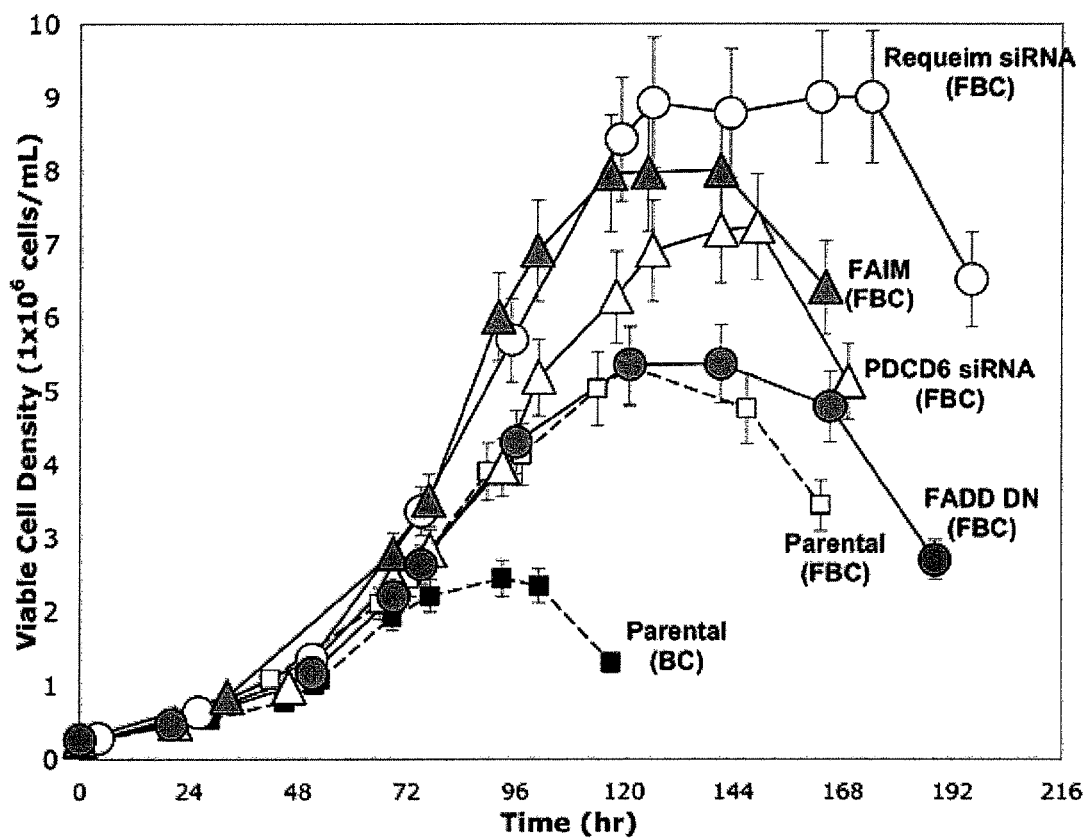
FIG. 8B shows viable cell densities of stable CHO IFN-γ clones with either Requiem or PDCD6 suppression or FADD DN or FAIM* overexpression in fed-batch cultures.

FIG. 8A shows the viable cell densities of stably integrated CHO IFN-γ cell lines with Requiem or PDCD6 suppression. PDCD6 and Requiem suppression allows for significant increase in viable cell densities during fed-batch culture.

Viable cell density of as high as $9 \times 10^6$ cells/mL can be achieved compared to $5 \times 10^6$ cells/mL typically seen in cells without any apoptosis targeting.

The experiments are repeated with stably integrated CHO IFN-γ cell lines showing FADD DN or FAIM over-expression and similar results are observed.

This demonstrates that apoptosis resistance engineering by Requiem or PDCD6 suppression or FAIM and FADD DN overexpression not only allows for extension of culture viability but confers the ability to grow to much higher viable cell densities due to their robustness against factor(s) that inhibit cell growth.

Example 23

Enhanced Recombinant Protein Yield in Fed-Batch Culture

Figure 9A:
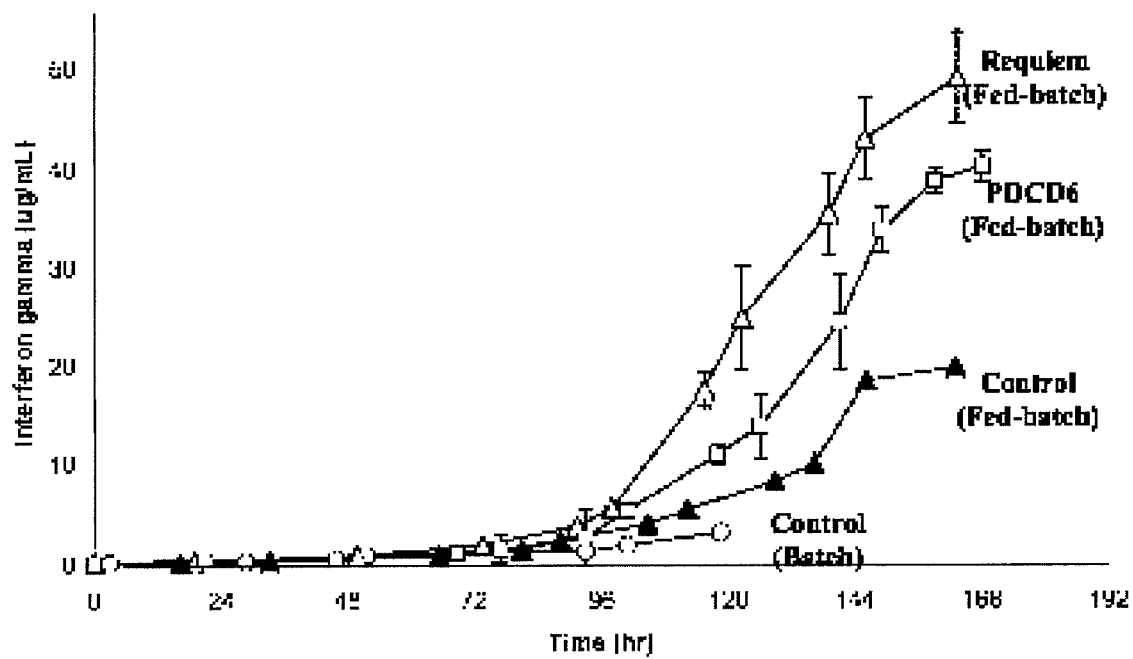
FIG. 9A shows interferon gamma yields of stable CHO IFN-γ clones with either Requiem or PDCD6 suppression or FADD DN* or FAIM* overexpression in fed-batch cultures. (Data presented are the averages of two duplicate experiments)
Figure 9B:
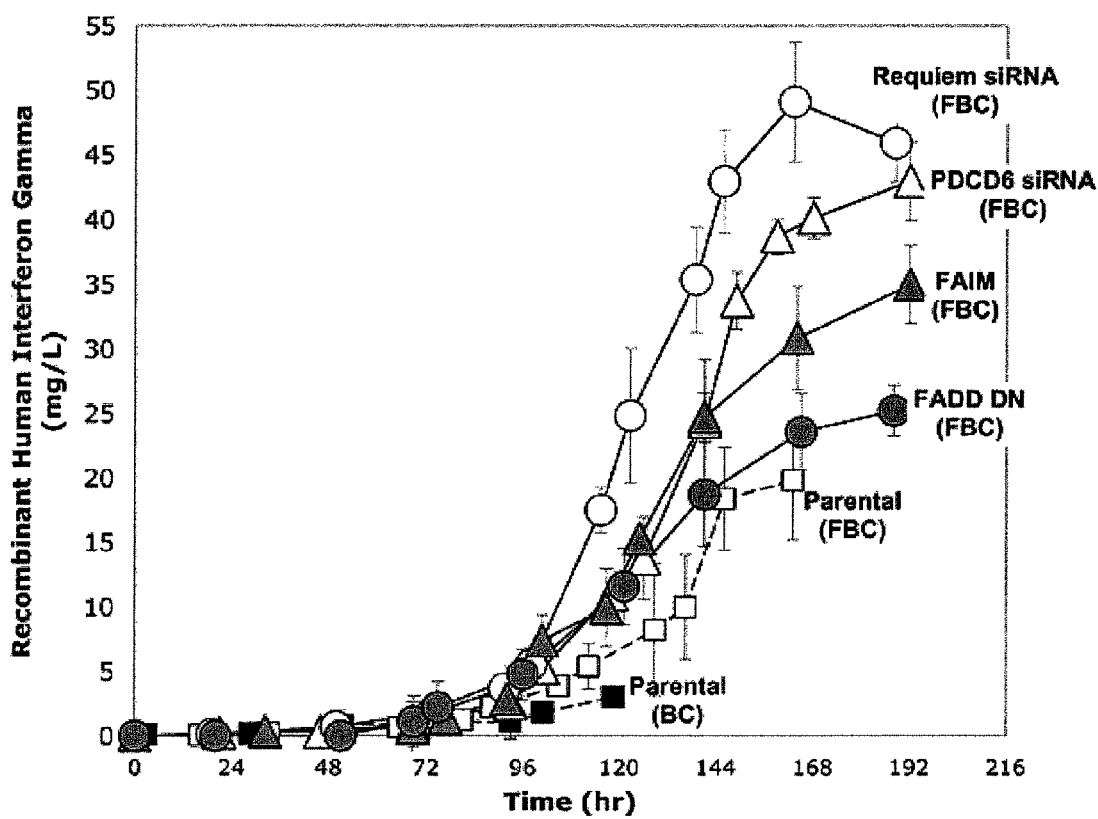
FIG. 9B shows interferon gamma yields of stable CHO IFN-γ clones with either Requiem or PDCD6 suppression or FADD DN* or FAIM* overexpression in fed-batch cultures.

FIG. 9A shows that gene targeting allows for further significant improvement in interferon gamma production and yield.

Cells with stably suppressed Requiem or PDCD6 give interferon gamma yields of up to 49 and 41 μg/mL respectively compared to the typical 20 μg/mL seen in normal fed-batch culture. This represents a greater than 200% improvement in recombinant protein yield.

The experiments are repeated with cells overexpressing FAIM and similar results are seen.

Example 24

Enhanced Silylation of Recombinant Human IFN-γ in Modified CHO Cell Lines

Sialic Acid Content Assay

Modified CHO cell lines which express IFN-γ are produced from parental CHO cell lines as described above.

Recombinant IFN-γ is purified from samples collected at mid-exponential growth phase and at when the highest IFN-γ concentrations are detected during high viability (>95%) and during low viability (70-80%).

The sialic acid content of the IFN-γ is then determined using a modified thiobarbituric acid assay as described in Wong et al. (2005a), *Biotechnol Bioeng* 89: 164-177).

Example 25

Enhanced Silylation of Recombinant Human IFN-γ in Modified CHO Cell Lines

Results

Figure 10:
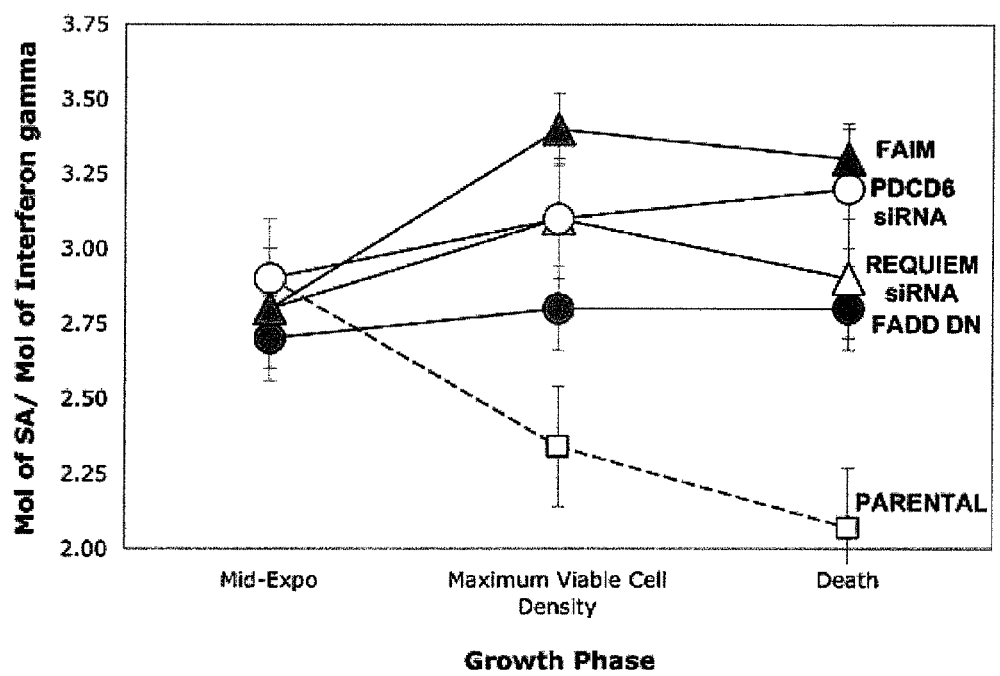
FIG. 10 shows sialyation of recombinant IFN-γ in stable CHO IFN-γ clones with either Requiem or PDCD6 suppression or FADD DN* or FAIM* over-expression during mid-exponential, stationary and death phase of fed-batch cultures.

FIG. 10 shows the sialyation of recombinant human IFN-γ harvested at three time points during fed-batch culture, namely at the mid-exponential (>95% viability), stationary (>95% viability) and death phase (70-80% viability) for the modified CHO IFN-γ cell lines and parental CHO IFN-γ cell lines.

For the latter, the sialic acid content of recombinant human IFN-γ decreased as the culture progressed from mid-exponential (2.9 mol of SA/mol of IFN-γ) to stationary (2.3 mol of SA/mol of IFN-γ) to death phase (2.1 mol of SA/mol of IFN-γ).

In contrast, the sialic acid content of IFN-γ harvested at the three time points for the four modified CHO IFN-γ cell lines are maintained, and even showed increase in sialyation, ranging from 2.7 to 3.5 mol of SA/mol of IFN-γ.

These results show that another potential benefit of apoptosis-resistant CHO cells is the maintenance/enhancement of protein glycosylation quality over extended culture time, regardless of loss in culture viability (70-80%). This is a distinct advantage for cell lines used for manufacturing biotherapeutics as a lower degree of sialyation can decrease the in vivo half-life of protein-based drugs (Varki, 1993, *Biotechnol Bioeng* 43:423-428; Gramer et al., 1995, *Glycobiology* 3:97-130).

REFERENCES

Altschul S F, Thomas L M, Alejandro A S, Jinghui Z, Zheng Z, Webb M, and David J L (1997) Gapped BLAST and PSI-BLAST: a new generation of protein database search programs. *Nucleic Acids Res.* 25:3389-3402.

Chestkov, A. V., Baka, I. D., Kost, M. V., Georgiev, G. P., Buchman, V. L. (1996) The d4 gene family in the human genome. *Genomics* 36: 174-177

Chinnaiyan A M, O'Rourke K, Tewari M and Dixit V M. (1995) FADD, a novel death domain-containing protein, interacts with the death domain of Fas and initiates apoptosis. *Cell*, May 81(4):505-12

Chinnaiyan A M, Tepper C G, Seldin M F, O'Rourke K, Kischkel F C, Hellbardt S, Krammer P H, Peter M E, and Dixit V M. (1996) FADD/MORT1 is a common mediator of CD95(Fas/APO-1 and TNF receptor-induced apoptosis. *The Journal of Biological Chemistry.* 271(9):4961-4965

Cohen G M (1997) Caspases: the executioners of apoptosis. *Biochem J* 326: 1-16

Fussenegger M., Fassnacht D., Schwartz R., Zanghi J. A., Graf M., Bailey J. E. and Portner R. (2000) Regulated overexpression of the survival factor bcl-2 in CHO cells increases viable cell density in batch culture and decrease DNA release in extended fixed-bed cultivation. *Cytotechnology* 32:45-61

Gabig T G, Mantel P L, Rosli R and Crean C D. (1994) Requiem: a novel zinc finger gene essential for apoptosis in myeloid cells. *J. Biol. Chem.* 269(47):29515-9

Gabig, T. G., Crean, C. D., Klenk, A., Long, H., Copeland, N. G., Gilbert, D. J., Jenkins, N. A., Quincey, D., Parente, F., Lespinasse, F., Carle, G. F., Gaudray, P., et al. (1998) Expression and chromosomal localization of the Requiem gene. *Mammalian Genome* 9: 660-665

Goswami J., Sinskey A. J., Steller H., Stephanopoulos and Wang D I C. (1999) Apoptosis in batch cultures of Chinese hamster ovary cells. *Biotechnol Bioeng.* 62: 632-640

Gramer M J, Goochee C F. 1994. Glycosidase activities of the 293 and NS0 cell lines and of an antibody-producing hybridoma cell line. Biotechnol Bioeng 43:423-428

Hu Y, Benedict M A, Ding L and Nunez G (1999) Role of cytochrome c and dATP/ATP hydrolysis in APAF-1 mediated caspase-9 activation and apoptosis. *EMBO J.* 18: 3586-3595

Jang, I. K., Hu, R., Lacana, E., D'Adamio, L., Gu, H. (2002) Apoptosis-linked gene 2-deficient mice exhibit normal T-cell development and function. *Molec. Cell. Biol.* 22: 4094-4100

Jung, Y. S., Kim, K. S., Kim, K. D., Lim, J. S., Kim, J. W. and Kim, E.(2001) Apoptosis-linked gene 2 binds to the death domain of Fas and dissociates from Fas during Fas-mediated apoptosis in Jurkat cells. *Biochem. Biophys. Res. Commun.* 288(2):420-426

Kerr J F R, Wyllie A H and Currie A R (1972) Apoptosis: a basic biological phenomenon with wide-ranging implications in tissue kinetics. *Br. J. Cancer* 26:239-257

Krebs, J. and Klemenz, R. (2000) The ALG-2/AIP-complex, a modulator at the interface between cell proliferation and cell death? A hypothesis. *Biochim. Biophys. Acta* 1498 (2-3): 153-161

Laken H A and Leonard M W. (2001) Understanding and modulation apoptosis in industrial cell culture. *Cur. Opinion. in Biotechnol.* 12:1/5-1/9

Lee Y, Yap M G S, Hu W S and Wong K T Y. 2003. Low-glutamine fed-batch cultures of 293-HEK serum-free suspension cells for adenovirus production. Biotechnol. Prog. 19:501-509

Li P, Nijhawan D., Budihardjo I., Srinivasula S. M., Ahmad M., Alnemri E. S, and Wang X. (1997) Cytochorme c and dATP-dependent formation of Apaf-1/caspase-9 complex initiates an apoptotic protease cascade. *Cell.* 91:479-489

Mastrangelo A. J., Hardwich J. M., Zou S, and Betenbaugh M. J. (2000) Over-expression of bcl-2 family members enhances survival of mammalian cells in response to various culture insults. *Biotechnol Bioeng.* 67:555-564

Nicholson D W and Thornberry N A (1997) Caspases: killer proteases. *Trends Biochem Sci.* 272: 2952-2956

Rothstein T L, Zhong X, Schram B R, Negm R S, Donohoe T J, Cabral D S, Foote L C, Schneider T J. (2000) Receptor-specific regulation of B-cell susceptibility to Fas-mediated apoptosis and a novel Fas apoptosis inhibitory molecule. Immunol Rev. 176:116-33.

Scahill, S J, Devos R, Der Heyden V J and Fiers W. 1983. Expression and characterization of the product of a human immune interferon cDNA gene in Chinese hamster ovary cells. Proc. Natl. Acad. Sci. USA. 80: 4654-4658

Schneider T J, Fischer G M, Donohoe T J, Colarusso T P and Thomas L. Rothstein (1999) A Novel Gene Coding for a Fas Apoptosis Inhibitory Molecule (FAIM) Isolated from Inducibly Fas-resistant B Lymphocytes J. Exp. Med., Volume 189, Number 6, Mar. 15, 1999 949-956

Srinivasula S. M., Ahmand M., Hernandes-Alnemri T., Litwack G. and Alnemri E. S. (1996) Molecular ordering of the Fas-apoptotic pathway: The Fas/APO-1 protease Mch5 is a CrmA-inhibitable protease that activates multiple Ced-3/ICE-like cysteine proteases. *Proc. Natl. Acad. Sci. USA.* 93:14486-14491

Tey B. T., Singh R. P., Piredda L., Piacentini M. and Al-Rubeai M. (2000) Influence of Bcl-2 on cell death during the cultivation of a Chinese hamster ovary cell line expressing a chimeric antibody. *Biotechnol Bioeng.* 68:31-43

Thornberry N A and Littlewood Y (1998) Caspases: Enemies within. *Science* 281:1312-1316

Urlaub & Chasin. 1980. Isolation of Chinese hamster cell mutants deficient in dihydrofolate reductase activity Proc. Natl. Acad. Sci. USA. 77: 4216-4220

Varki A. 1993. Biological roles of oligosaccharides: All of the theories are correct. Glycobiology 3:97-130

Vito P, Lacana E and D'Adamio L. (1996) Interfering with apoptosis: $Ca^{2+}$ binding protein ALG-2 and Alzheimer's disease gene ALG-3. *Science.* 271(5248):521-5

Wong C F D, Wong T K, Goh L T, Heng C K, Yap G S M. 2005a. Impact of dynamic online fed-batch strategies on metabolism, productivity and N-glycosylation quality in CHO cell cultures. Biotechnol Bioeng 89: 164-177

Zhong X, Schneider T J, Cabral D S, Donohoe T J, Rothstein T L. (2001) An alternatively spliced long form of Fas apoptosis inhibitory molecule (FAIM) with tissue-specific expression in the brain. Mol. Immunol. 2001 January; 38(1): 65-72

Zou H, Li Y, Liu X and Wang X (1999) An APAF-1 cytochrome c multimeric complex is a functional apoptosome that activates procaspase-9. *J Biol Chem* 274: 11549-11556

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

We claim:

1. An isolated polypeptide comprising a cgPDCD6 sequence shown as SEQ ID NO: 3.

2. An isolated polypeptide comprising a *Cricetulus griseus* sequence capable of mediating apoptosis of a cell, the sequence being a cgPDCD6 sequence shown as SEQ ID NO: 3.

3. A composition comprising the isolated polypeptide according to claim 1 or claim 2 together with a carrier or diluent.

* * * * *

SEQUENCE LISTING

<160> NUMBER OF SEQ ID NOS: 44

<210> SEQ ID NO 1
<211> LENGTH: 179
<212> TYPE: PRT
<213> ORGANISM: Cricetulus griseus

<400> SEQUENCE: 1

Met Thr Asp Leu Val Ala Val Trp Asp Val Ala Leu Ser Asp Gly Val
1               5                   10                  15

His Lys Ile Glu Phe Glu His Gly Thr Thr Ser Gly Lys Arg Val Val
            20                  25                  30

Tyr Val Asp Gly Lys Glu Glu Ile Arg Lys Glu Trp Met Phe Lys Leu
        35                  40                  45

Val Gly Lys Glu Thr Phe Cys Val Gly Ala Ala Lys Thr Lys Ala Thr
    50                  55                  60

Ile Asn Ile Asp Ala Val Ser Gly Phe Ala Tyr Glu Tyr Thr Leu Glu
65                  70                  75                  80

Ile Asp Gly Lys Ser Leu Lys Lys Tyr Met Glu Asn Arg Ser Lys Thr
                85                  90                  95

Thr Asn Thr Trp Val Leu His Leu Asp Gly Gln Asp Leu Arg Val Val
            100                 105                 110

Leu Glu Lys Asp Thr Met Asp Val Trp Cys Asn Gly Gln Lys Met Glu
        115                 120                 125

Thr Ala Gly Glu Phe Val Asp Asp Gly Thr Glu Thr His Phe Ser Val
    130                 135                 140

Gly Asn His Asp Cys Tyr Ile Lys Ala Val Ser Ser Gly Lys Arg Arg
145                 150                 155                 160

Glu Gly Ile Ile His Thr Leu Ile Val Asp Asn Arg Glu Ile Pro Glu
                165                 170                 175

Leu Pro Gln

<210> SEQ ID NO 2
<211> LENGTH: 180
<212> TYPE: PRT
<213> ORGANISM: Cricetulus griseus

<400> SEQUENCE: 2

Met Asp Pro Phe Leu Val Leu Leu His Ser Val Ser Gly Asn Leu Ser
1               5                   10                  15

Ser Ser Asp Leu Leu Glu Leu Lys Phe Leu Cys Arg Glu Arg Val Ser
            20                  25                  30

Lys Arg Lys Leu Glu Arg Val Gln Ser Gly Leu Asp Leu Phe Ser Val
        35                  40                  45

Leu Leu Glu Gln Asn Asp Leu Gly Arg Thr Arg Thr Gly Leu Leu Arg
    50                  55                  60

Glu Leu Leu Ala Ser Leu Arg Arg His Asp Leu Leu Gln Arg Leu Asp
65                  70                  75                  80

Asp Phe Glu Ala Gly Thr Ala Ala Ser Ala Ala Pro Gly Glu Ala Asp
                85                  90                  95

Leu Arg Val Ala Phe Asp Ile Val Cys Asp Asn Val Gly Arg Asp Trp
            100                 105                 110

Lys Arg Leu Ala Arg Gln Leu Lys Val Ser Glu Ala Lys Ile Asp Gly
        115                 120                 125

```
Ile Glu Glu Arg Tyr Pro Arg Ser Leu Ser Glu Gln Val Arg Glu Ala
            130                 135                 140

Leu Arg Val Trp Lys Ile Ala Glu Arg Glu Lys Ala Thr Val Ala Gly
145                 150                 155                 160

Leu Val Lys Ala Leu Arg Ala Cys Arg Leu Asn Leu Val Ala Asp Leu
                165                 170                 175

Val Glu Gly Arg
            180

<210> SEQ ID NO 3
<211> LENGTH: 191
<212> TYPE: PRT
<213> ORGANISM: Cricetulus griseus

<400> SEQUENCE: 3

Met Ala Ala Tyr Ser Tyr Arg Pro Gly Pro Gly Ala Gly Pro Gly Pro
1               5                   10                  15

Ser Ala Gly Ala Ala Leu Pro Asp Gln Ser Phe Leu Trp Asn Val Phe
                20                  25                  30

Gln Arg Val Asp Lys Asp Arg Ser Gly Val Ile Ser Asp Asn Glu Leu
            35                  40                  45

Gln Gln Ala Leu Ser Asn Gly Thr Trp Thr Pro Phe Asn Pro Val Thr
        50                  55                  60

Val Arg Ser Ile Ile Ser Met Phe Asp Arg Glu Asn Lys Ala Gly Val
65                  70                  75                  80

Asn Phe Ser Glu Phe Thr Gly Val Trp Lys Tyr Ile Thr Asp Trp Gln
                85                  90                  95

Asn Val Phe Arg Thr Tyr Asp Arg Asp Asn Ser Gly Met Ile Asp Lys
            100                 105                 110

Asn Glu Leu Lys Gln Ala Leu Ser Gly Phe Gly Tyr Arg Leu Ser Asp
        115                 120                 125

Gln Phe His Asp Ile Leu Ile Arg Lys Phe Asp Arg Gln Gly Arg Gly
    130                 135                 140

Gln Ile Ala Phe Asp Asp Phe Ile Gln Gly Cys Ile Val Leu Gln Arg
145                 150                 155                 160

Leu Thr Asp Ile Phe Arg Arg Tyr Asp Thr Asp Gln Asp Gly Trp Ile
                165                 170                 175

Gln Val Ser Tyr Glu Gln Tyr Leu Ser Met Val Phe Ser Ile Val
            180                 185                 190

<210> SEQ ID NO 4
<211> LENGTH: 391
<212> TYPE: PRT
<213> ORGANISM: Cricetulus griseus

<400> SEQUENCE: 4

Met Ala Ala Val Val Glu Asn Val Val Lys Leu Leu Gly Glu Gln Tyr
1               5                   10                  15

Tyr Lys Asp Ala Met Glu Gln Cys His Asn Tyr Asn Ala Arg Leu Cys
                20                  25                  30

Ala Glu Arg Ser Val Arg Leu Pro Phe Leu Asp Ser Gln Thr Gly Val
            35                  40                  45

Ala Gln Ser Asn Cys Tyr Ile Trp Met Glu Lys Arg His Arg Gly Pro
        50                  55                  60

Gly Leu Ala Ser Gly Gln Leu Tyr Ser Tyr Pro Ala Arg Arg Trp Arg
65                  70                  75                  80
```

```
Lys Lys Arg Arg Ala His Pro Pro Glu Asp Pro Arg Leu Ser Phe Pro
                85                  90                  95

Ser Ile Lys Pro Asp Thr Asp Gln Thr Leu Lys Lys Glu Gly Leu Ile
            100                 105                 110

Ser Gln Asp Gly Ser Ser Leu Glu Ala Leu Leu Arg Thr Asp Pro Leu
            115                 120                 125

Glu Lys Arg Gly Ala Pro Asp Pro Arg Val Asp Asp Ser Leu Gly
            130                 135                 140

Glu Phe Pro Val Thr Asn Ser Arg Ala Arg Lys Arg Ile Leu Glu Pro
145                 150                 155                 160

Asp Asp Phe Leu Asp Asp Leu Asp Asp Glu Asp Tyr Glu Glu Asp Thr
                165                 170                 175

Pro Lys Arg Arg Gly Lys Gly Lys Ser Lys Ser Lys Gly Val Ser Ser
            180                 185                 190

Ala Arg Lys Lys Leu Asp Ala Ser Ile Leu Glu Asp Arg Asp Lys Pro
            195                 200                 205

Tyr Ala Cys Asp Ile Cys Gly Lys Arg Tyr Lys Asn Arg Pro Cys Leu
210                 215                 220

Ser Tyr His Tyr Ala Tyr Ser His Leu Ala Glu Glu Gly Glu Asp
225                 230                 235                 240

Lys Glu Asp Ser Gln Pro Pro Thr Pro Val Ser Gln Arg Ser Glu Glu
                245                 250                 255

Gln Lys Ser Lys Lys Gly Pro Asp Gly Leu Ala Leu Pro Asn Asn Tyr
            260                 265                 270

Cys Asp Phe Cys Leu Gly Asp Ser Lys Ile Asn Lys Lys Thr Gly Gln
            275                 280                 285

Pro Glu Glu Leu Val Ser Cys Ser Asp Cys Gly Arg Ser Gly His Pro
290                 295                 300

Ser Cys Leu Gln Phe Thr Pro Val Met Met Ala Ala Val Lys Thr Tyr
305                 310                 315                 320

Arg Trp Gln Cys Ile Glu Cys Lys Cys Cys Asn Leu Cys Gly Thr Ser
                325                 330                 335

Glu Asn Asp Asp Gln Leu Leu Phe Cys Asp Asp Cys Asp Arg Gly Tyr
            340                 345                 350

His Met Tyr Cys Leu Thr Ser Ser Met Ser Glu Pro Pro Glu Gly Ser
            355                 360                 365

Trp Ser Cys His Leu Cys Leu Asp Leu Leu Lys Glu Lys Ala Ser Ile
            370                 375                 380

Tyr Gln Asn Gln Ser Ser Ser
385                 390

<210> SEQ ID NO 5
<211> LENGTH: 881
<212> TYPE: DNA
<213> ORGANISM: Cricetulus griseus

<400> SEQUENCE: 5
gccgcgagag ctgctgacta cgtcgtggga tcaggagccg gtggcggagc gccgggcagc      60
cctctttata acctggaaaa aatgacagat cttgtagctg tttgggacgt tgcattaagt     120
gatggagtcc acaagattga atttgagcat gggaccacat caggcaaacg agttgtgtac     180
gtggatggga aggaagagat aagaaaagaa tggatgttca aattggtggg caaagaaacc     240
ttctgtgttg gagctgcgaa aaccaaagcc accataaata tagatgctgt cagtggtttt     300
gcttatgagt ataccctgga aatcgatggg aaaagcctca gaagtacat ggagaacaga     360
```

| | |
|---|---|
| tcaaagacca ccaacacctg ggtactgcac ttggatggcc aggacttaag agttgttttg | 420 |
| gaaaaagata ctatggatgt atggtgcaat ggtcaaaaaa tggagacagc aggcgagttt | 480 |
| gtagatgatg gaactgaaac acacttcagt gttgggaacc atgactgtta cataaaagct | 540 |
| gtcagcagcg ggaagagaag agaagggatt atccacacac tcattgtgga taacagggag | 600 |
| atcccagagc tccctcagtg actgctggtt agtgggttct gagctgaaga ggagacatca | 660 |
| ggactttcta atggctgtgg taattaaatg tgttcactgt gtacatattg gtagatttag | 720 |
| tctgcaatgt ttttatttt tgttactgga aactgtaata ttccaatggt caagaaaaat | 780 |
| gtggaatcat aaaaatttat tttttaacta ctgtaaagtg tttctaattc aaataggaaa | 840 |
| taaaatatgg accaaaccca ttcatatctc accacagtaa c | 881 |

<210> SEQ ID NO 6
<211> LENGTH: 542
<212> TYPE: DNA
<213> ORGANISM: Cricetulus griseus

<400> SEQUENCE: 6

| | |
|---|---|
| ccatggaccc attcctggtg ctgctgcact cggtgtctgg caacttgtcg agcagcgatc | 60 |
| tgctggagct aaagttcctg tgccgtgagc gcgtgagcaa acgaaagctg agcgtgtgc | 120 |
| agagtggcct ggacctgttc tcagtgctgc tggagcagaa cgatctggag cgcacacgca | 180 |
| ccgggctgct cgtgagctg ctggcctcgc tgcgcagaca cgatctcctg caacgcctgg | 240 |
| acgactttga agcggggacg gcggcctcgg ccgcaccggg ggaggcagat ctgcgggtgg | 300 |
| cctttgacat tgtatgcgac aatgtgggga gagattggaa gagactggcc cgccagctga | 360 |
| aagtgtctga ggccaaaatt gatgggattg aggagaggta cccccgaagc ctgagtgagc | 420 |
| aggtaaggga ggctctgaga gtctggaaga ttgccgagag ggagaaagcc acggtggctg | 480 |
| gactggtaaa ggcacttcgg gcctgccggc tgaacctggt ggctgacctg gtggaaggga | 540 |
| gg | 542 |

<210> SEQ ID NO 7
<211> LENGTH: 1068
<212> TYPE: DNA
<213> ORGANISM: Cricetulus griseus

<400> SEQUENCE: 7

| | |
|---|---|
| gcccatggct gcctactcct accgcccagg cccgggcgcc ggccccggcc cttctgctgg | 60 |
| agctgcgctg ccagaccaga gcttcctgtg gaacgtcttc cagcgggttg ataaagacag | 120 |
| gagtggagtg atttcagaca atgagcttca gcaagcatta tccaatggta cttggactcc | 180 |
| gtttaatcca gtgactgtta ggtcaatcat ttctatgttt gaccgagaaa acaaggctgg | 240 |
| cgtgaacttc agtgaattta caggcgtgtg gaagtacatc acagactggc agaatgtctt | 300 |
| ccgaacctat gaccgggaca actctgggat gattgacaag aacgagctca gcaagcact | 360 |
| ctcaggtttt ggctaccggc tctctgacca gttccatgac atcctcatcc gcaaatttga | 420 |
| cagacaagga cgagggcaga tcgcatttga tgacttcatc cagggctgca tcgtcttgca | 480 |
| gaggttgaca gacatattca gacgctatga cacggatcag gacggctgga ttcaggtgtc | 540 |
| ttatgagcag tatctctcca tggtcttcag catcgtataa ccaggccctg tgaacagcaa | 600 |
| gcacagcatg caaaaaagac tgaaaatgcc aaatccttc cctgtgatga aacagggcac | 660 |
| aagtacagtt agatgctgtt cttcctgtag gctgtataat taatacttgg ggacctggct | 720 |

-continued

| | |
|---|---|
| gtacatatgt gaataagctg gttagtgatt ctgtagtggc accctagcta cactgttata | 780 |
| atacaaacat tgggtttgct gactaattgt gccacgaggg gaaaccgaat attggttcag | 840 |
| gattctgctc tcaaactatc atgttctttt ctagctgtct ctaattctgt agttgaaaat | 900 |
| acttttatta gccaatagga ttttaaaata atatggaact tgcacagaag gctttttcatg | 960 |
| tgccttactt ttttaaaaaa gagtttatgt attcattgga atatgtaaca taagcaataa | 1020 |
| agtaatgatc cagcccaaaa aaaaaaaaaa aaaaaaaaaa aaaaaaaa | 1068 |

<210> SEQ ID NO 8
<211> LENGTH: 2482
<212> TYPE: DNA
<213> ORGANISM: Cricetulus griseus

<400> SEQUENCE: 8

| | |
|---|---|
| ggtatcaacg cagcctcccg gcgggaggga gaggagcagg gaagatggcg gctgtggtgg | 60 |
| agaatgtagt gaagctcctt ggggaacagt actacaaaga tgccatggaa cagtgccaca | 120 |
| attacaatgc ccgcctctgt gctgagcgta gcgtgcgtct gcctttcttg gactcacaga | 180 |
| ctggagtagc ccagagcaat tgttatatct ggatggaaaa gcgacaccgg ggaccaggat | 240 |
| tggcctctgg acagttgtac tcctaccctg cccggcgctg gcgtaaaaag cgtcgagctc | 300 |
| acccacctga ggatcccagg ctttcctttc catctattaa accagacaca gaccagaccc | 360 |
| tgaagaaaga ggggcttata tctcaggatg gcagcagttt agaggctcta ctgcgtactg | 420 |
| accctctgga gaaacgaggt gctccagatc ccgtgttga tgatgacagc ctgggcgagt | 480 |
| tcctgtcac caacagtcga gcacggaagc ggatccttga acctgatgac ttcctagatg | 540 |
| atcttgatga tgaagactat gaagaagata ctccaaaacg tcggggaaag gggaaatcca | 600 |
| agagtaaggg tgtgagcagt gcccggaaga aactggatgc ttccatcctg gaggaccgtg | 660 |
| ataagcccta tgcctgtgac atttgtggaa aacgctacaa gaatcgacct tgcctcagtt | 720 |
| accactatgc ctattcccac ctggctgagg aggagggaga ggacaaagaa gactctcaac | 780 |
| cacctactcc tgtttcccag aggtctgagg agcagaaatc caagaaagga cctgatggat | 840 |
| tagccctgcc caacaactac tgtgacttct gcctgggaga ctcaaaaatc aacaagaaga | 900 |
| cagggcagcc tgaggagcta gtgtcctgtt ctgactgtgg ccgctcaggg caccgtcct | 960 |
| gcctgcagtt caccccgtg atgatggcgg ctgtgaagac ctaccgctgg cagtgcatcg | 1020 |
| agtgcaagtg ctgcaacctc tgcggcactt cggagaatga cgaccagctg ctcttctgtg | 1080 |
| atgactgtga ccgtggctac cacatgtact gtctcacctc atccatgtcg gagcctcctg | 1140 |
| aaggaagttg gagctgccac ctgtgtctgg atctgctgaa ggagaaagcg tccatctacc | 1200 |
| agaaccagag ctcctcctga tgtgccaccc ggctccccac acacctaagg ctgttgctct | 1260 |
| cctctacctt ggttttcata cccctcttct tcttcttctt tcactctggt agttctgccc | 1320 |
| aactgccttt ggcaacagca cagggaaggt ggcaactctt gactgcctct ggtcccaagc | 1380 |
| cctcagggag taaggagcag catgctgccc caggctgatc tgtgggccca gcttctctct | 1440 |
| gctctccaag aagtgcattc actctgcttg ccttgggccc aagtccctgg taatcacagg | 1500 |
| gttcaaatgg gttcctctaa gaagtatgag agcagctcac ttgtctcaag cctggcctac | 1560 |
| ccctcctccc cctctggtgt ccagagtttt accccagggg tgagccaggc ctaacctttg | 1620 |
| cttggagcac ctggagtgat cagactgagg tggcacttgc taggacccct tcctacccct | 1680 |
| tgttctgctt cactttgcct ctgccaaagc agtcctgtgt cttctgtcat gctacatggg | 1740 |
| gtcctgtgct tgcactgtga tgctctcagg cacctcctgg ctctgtcctg ttctgcccag | 1800 |

```
tcccacaaag agacaagcag cttcacctgc ccttcccgtg cttggctggc gcgctcacag    1860
gtggtctctg gcaatccaaa catttcccat cctcagactt ttgagtcttc tgcctccttc    1920
cttgttccct ttggttttgt gggggagagg gacaatgtca gggggccctg ccagaagctt    1980
ggggaccaca agaagttgga taatgtgcct gttttttaac tcgataaaaa tgcctacctc    2040
caaaatcccc ttttcgttct tcctggacct gggcattcag cctcctgccc ttaactgaat    2100
caggagcctc tgcctcctac tgtgtatcct ggctcccagg agagaggatg gtccccttc     2160 cttgcacact agctagcagc tggtaaagtc ttctttccct gattttttgtt tcctgcttag    2220 tggcactgac attaagtagg aggggacagt ccatgccaga acactctgga atggccttcc    2280
tccttggctg tgggcaggcc ctgacttgtt ttctgcaaag ttgaggcccc tcctcctatc    2340
cttagttcct gtatccaaaa cattagtaag aataaacatt tttacacaga aaaaaaaaa     2400 aaaaaaaaaa aaaaaaaaaa aaaaaaaaaa aaaaaaaaaa aaaaaaaaaa aaaaaaaaaa    2460
aaaaaaaaaa aaaaaaaaaa aa                                             2482
```

<210> SEQ ID NO 9
<211> LENGTH: 82
<212> TYPE: PRT
<213> ORGANISM: Cricetulus griseus

<400> SEQUENCE: 9

```
Met Ala Phe Asp Ile Val Cys Asp Asn Val Gly Arg Asp Trp Lys Arg
 1               5                  10                  15

Leu Ala Arg Gln Leu Lys Val Ser Glu Ala Lys Ile Asp Gly Ile Glu
            20                  25                  30

Glu Arg Tyr Pro Arg Ser Leu Ser Glu Gln Val Arg Glu Ala Leu Arg
        35                  40                  45

Val Trp Lys Ile Ala Glu Arg Glu Lys Ala Thr Val Ala Gly Leu Val
    50                  55                  60

Lys Ala Leu Arg Ala Cys Arg Leu Asn Leu Val Ala Asp Leu Val Glu
65                  70                  75                  80

Gly Arg
```

<210> SEQ ID NO 10
<211> LENGTH: 253
<212> TYPE: DNA
<213> ORGANISM: Cricetulus griseus

<400> SEQUENCE: 10

```
gccaccatgg cctttgacat tgtatgcgac aatgtgggga gagattggaa gagactggcc      60
cgccagctga aagtgtctga ggccaaaatt gatgggattg aggagaggta ccccgaagc      120 ctgagtgagc aggtaaggga ggctctgaga gtctggaaga ttgccgagag ggagaaagcc    180
acggtggctg gactggtaaa ggcacttcgg gcctgccggc tgaacctagt ggctgacctg    240
gtggaaggga ggc                                                       253
```

<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
gatatcggat ccgccaccat ggcctttgac attgtatgcg acaatgtggg g    51

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cccgggctcg agtgcctccc ttccaccagg tcag    34

<210> SEQ ID NO 13
<211> LENGTH: 65
<212> TYPE: DNA
<213> ORGANISM: Artificial Sequence
<220> FEATURE:
<223> OTHER INFORMATION: Description of Artificial Sequence: Synthetic
      suppression vector insert

<400> SEQUENCE: 13
gatcccgtga gcttcagcaa gcattattca agagataatg cttgctgaag ctcattttt    60 ggaaa    65

<210> SEQ ID NO 14
<211> LENGTH: 64
<212> TYPE: DNA
<213> ORGANISM: Artificial Sequence
<220> FEATURE:
<223> OTHER INFORMATION: Description of Artificial Sequence: Synthetic
      suppression vector insert

<400> SEQUENCE: 14
agcttttcca aaaatgagc ttcagcaagc attatctctt gaataatgct tgctgaagct    60
cacg    64

<210> SEQ ID NO 15
<211> LENGTH: 64
<212> TYPE: DNA
<213> ORGANISM: Artificial Sequence
<220> FEATURE:
<223> OTHER INFORMATION: Description of Artificial Sequence: Synthetic
      suppression vector insert

<400> SEQUENCE: 15
gatcccgcgg atccttgaac ctgatttcaa gagaatcagg ttcaaggatc cgcttttttg    60
gaaa    64

<210> SEQ ID NO 16
<211> LENGTH: 64
<212> TYPE: DNA
<213> ORGANISM: Artificial Sequence
<220> FEATURE:
<223> OTHER INFORMATION: Description of Artificial Sequence: Synthetic
      suppression vector insert

<400> SEQUENCE: 16
agcttttcca aaaagcgga tccttgaacc tgattctctt gaaatcaggt tcaaggatcc    60
gcgg    64

<210> SEQ ID NO 17
<211> LENGTH: 28
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 17
gccgcgagag ctgctgacta cgtcgtgg                                       28

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gttactgtgg tgagatatga atgggtttgg                                     30

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccatggaccc attcctggtg c                                              21

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttcttccacc aggtcagcca cc                                             22

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcccatggct gcctactcct a                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aatccagcca tcctgatccg t                                              21

<210> SEQ ID NO 23
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 23
cagcgggttg ataaagacag gagtggagtg                                         30

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atggcggctg tggtggagaa t                                                  21

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggagttctgg ttctggtaga tgg                                                23

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcctcagtta ccactatgcc cattcccacc                                         30

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tggagctgcg aaaaccaaag                                                    20

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aaactcgcct gctgtctcca t                                                  21

<210> SEQ ID NO 29
<211> LENGTH: 22
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 29
gatatcggat ccgccaccat gg                                            22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgcctccctt ccaccaggtc ag                                            22

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cagcgggttg ataaagacag g                                             21

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gccagccttg ttttctcgg                                                19

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tggagtagcc cagagcaatt g                                             21

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tcgacgcttt ttacgccag                                                19

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic

```
                           primer

<400> SEQUENCE: 35
agctgagagg gaaattgtgc g                                              21

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gcaacggaac cgctcatt                                                  18

<210> SEQ ID NO 37
<211> LENGTH: 6056
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 37
gacggatcgg gagatctccc gatccctat   ggtgcactct cagtacaatc tgctctgatg     60
ccgcatagtt aagccagtat ctgctcctg   cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc   cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattcgcc    960
accatgacag atcttgtagc tgtttgggac gttgcattaa gtgatggagt ccacaagatt   1020
gaatttgagc atgggaccac atcaggcaaa cgagttgtgt acgtggatgg aaggaagag    1080 ataagaaaag aatggatgtt caaattggtg ggcaaagaaa ccttctgtgt tggagctgcg   1140
aaaaccaaag ccaccataaa tatagatgct gtcagtggtt ttgcttatga gtataccctg   1200
gaaatcgatg ggaaaagcct caagaagtac atggagaaca gatcaaagac caccaacacc   1260
tgggtactgc acttggatgg ccaggactta agagttgttt tggaaaaaga tactatggat   1320
gtatggtgca atggtcaaaa aatggagaca gcaggcgagt ttgtagatga tggaactgaa   1380
acacacttca gtgttgggaa ccatgactgt acataaaag   ctgtcagcag cgggaagaga   1440
agagaaggga ttatccacac actcattgtg gataacaggg agatcccaga gctccctcag   1500
```

```
tgactgctgg ttagtgggtt ctgagctgaa gaggagacat caggactttc taatggctgt    1560
ggtaattaaa tgtgttcacg aattctgcag atatccagca cagtggcggc cgctcgagtc    1620
tagagggccc gtttaaaccc gctgatcagc ctcgactgtg ccttctagtt gccagccatc    1680
tgttgtttgc ccctcccccg tgccttcctt gaccctggaa ggtgccactc ccactgtcct    1740
ttcctaataa aatgaggaaa ttgcatcgca ttgtctgagt aggtgtcatt ctattctggg    1800
gggtggggtg gggcaggaca gcaaggggga ggattgggaa gacaatagca ggcatgctgg    1860
ggatgcggtg ggctctatgg cttctgaggc ggaaagaacc agctgggct ctaggggta    1920 tccccacgcg ccctgtagcg gcgcattaag cgcggcgggt gtggtggtta cgcgcagcgt    1980
gaccgctaca cttgccagcg ccctagcgcc cgctcctttc gctttcttcc cttccttttct    2040 cgccacgttc gccggctttc cccgtcaagc tctaaatcgg gggctcccctt tagggttccg    2100 atttagtgct ttacggcacc tcgaccccaa aaaacttgat tagggtgatg gttcacgtag    2160
tgggccatcg ccctgataga cggttttttcg cccttttgacg ttggagtcca cgttctttaa    2220
tagtggactc ttgttccaaa ctggaacaac actcaaccct atctcggtct attcttttga    2280
tttataaggg attttgccga tttcggccta ttggttaaaa aatgagctga tttaacaaaa    2340
atttaacgcg aattaattct gtggaatgtg tgtcagttag ggtgtggaaa gtccccaggc    2400
tccccagcag gcagaagtat gcaaagcatg catctcaatt agtcagcaac caggtgtgga    2460
aagtccccag gctccccagc aggcagaagt atgcaaagca tgcatctcaa ttagtcagca    2520
accatagtcc cgcccctaac tccgcccatc ccgcccctaa ctccgcccag ttccgcccat    2580
tctccgcccc atggctgact aatttttttt atttatgcag aggccgaggc cgcctctgcc    2640
tctgagctat tccagaagta gtgaggaggc ttttttggag gcctaggctt ttgcaaaaag    2700
ctcccgggag cttgtatatc cattttcgga tctgatcaag agacaggatg aggatcgttt    2760
cgcatgattg aacaagatgg attgcacgca ggttctccgg ccgcttgggt ggagaggcta    2820
ttcggctatg actgggcaca acagacaatc ggctgctctg atgccgccgt gttccggctg    2880
tcagcgcagg ggcgcccggt tctttttgtc aagaccgacc tgtccggtgc cctgaatgaa    2940
ctgcaggacg aggcagcgcg gctatcgtgg ctggccacga cgggcgttcc ttgcgcagct    3000
gtgctcgacg ttgtcactga agcgggaagg gactggctgc tattgggcga agtgccgggg    3060
caggatctcc tgtcatctca ccttgctcct gccgagaaag tatccatcat ggctgatgca    3120
atgcggcggc tgcatacgct tgatccggct acctgcccat tcgaccacca agcgaaacat    3180
cgcatcgagc gagcacgtac tcggatggaa gccggtcttg tcgatcagga tgatctggac    3240
gaagagcatc aggggctcgc gccagccgaa ctgttcgcca ggctcaaggc gcgcatgccc    3300
gacggcgagg atctcgtcgt gacccatggc gatgcctgct tgccgaatat catggtggaa    3360
aatggccgct tttctggatt catcgactgt ggccggctgg gtgtggcgga ccgctatcag    3420
gacatagcgt tggctacccg tgatattgct gaagagcttg gcggcgaatg ggctgaccgc    3480
ttcctcgtgc tttacggtat cgccgctccc gattcgcagc gcatcgcctt ctatcgcctt    3540
cttgacgagt tcttctgagc gggactctgg ggttcgaaat gaccgaccaa gcgacgccca    3600
acctgccatc acgagatttc gattccaccg ccgccttcta tgaaaggttg gcttcggaa    3660 tcgttttccg gacgccggc tggatgatcc tccagcgcgg ggatctcatg ctggagttct    3720
tcgcccaccc caacttgttt attgcagctt ataatggtta caaataaagc aatagcatca    3780
caaatttcac aaataaagca tttttttcac tgcattctag ttgtggtttg tccaaactca    3840
```

```
tcaatgtatc ttatcatgtc tgtataccgt cgacctctag ctagagcttg gcgtaatcat   3900
ggtcatagct gtttcctgtg tgaaattgtt atccgctcac aattccacac aacatacgag   3960
ccggaagcat aaagtgtaaa gcctggggtg cctaatgagt gagctaactc acattaattg   4020
cgttgcgctc actgcccgct ttccagtcgg gaaacctgtc gtgccagctg cattaatgaa   4080
tcggccaacg cgcggggaga ggcggtttgc gtattgggcg ctcttccgct tcctcgctca   4140
ctgactcgct gcgctcggtc gttcggctgc ggcgagcgg atcagctcac tcaaaggcgg   4200
taatacggtt atccacagaa tcaggggata acgcaggaaa gaacatgtga gcaaaaggcc   4260
agcaaaaggc caggaaccgt aaaaaggccg cgttgctggc gtttttccat aggctccgcc   4320
cccctgacga gcatcacaaa aatcgacgct caagtcagag gtggcgaaac ccgacaggac   4380
tataaagata ccaggcgttt ccccctggaa gctccctcgt gcgctctcct gttccgaccc   4440
tgccgcttac cggatacctg tccgcctttc tcccttcggg aagcgtggcg ctttctcata   4500
gctcacgctg taggtatctc agttcggtgt aggtcgttcg ctccaagctg ggctgtgtgc   4560
acgaaccccc cgttcagccc gaccgctgcg ccttatccgg taactatcgt cttgagtcca   4620
acccggtaag acacgactta tcgccactgg cagcagccac tggtaacagg attagcagag   4680
cgaggtatgt aggcggtgct acagagttct tgaagtggtg gcctaactac ggctacacta   4740
gaagaacagt atttggtatc tgcgctctgc tgaagccagt taccttcgga aaaagagttg   4800
gtagctcttg atccggcaaa caaaccaccg ctggtagcgg tttttttgtt tgcaagcagc   4860
agattacgcg cagaaaaaaa ggatctcaag aagatccttt gatcttttct acggggtctg   4920
acgctcagtg gaacgaaaac tcacgttaag ggattttggt catgagatta tcaaaaagga   4980
tcttcaccta gatccttttta aattaaaaat gaagttttaa atcaatctaa agtatatatg   5040
agtaaacttg gtctgacagt taccaatgct taatcagtga ggcacctatc tcagcgatct   5100
gtctatttcg ttcatccata gttgcctgac tccccgtcgt gtagataact acgatacggg   5160
agggcttacc atctggcccc agtgctgcaa tgataccgcg agacccacgc tcaccggctc   5220
cagatttatc agcaataaac cagccagccg gaagggccga gcgcagaagt ggtcctgcaa   5280
ctttatccgc ctccatccag tctattaatt gttgccggga agctagagta agtagttcgc   5340
cagttaatag tttgcgcaac gttgttgcca ttgctacagg catcgtggtg tcacgctcgt   5400
cgtttggtat ggcttcattc agctccggtt cccaacgatc aaggcgagtt acatgatccc   5460
ccatgttgtg caaaaaagcg gttagctcct tcggtcctcc gatcgttgtc agaagtaagt   5520
tggccgcagt gttatcactc atggttatgg cagcactgca taattctctt actgtcatgc   5580
catccgtaag atgcttttct gtgactggtg agtactcaac caagtcattc tgagaatagt   5640
gtatgcggcg accgagttgc tcttgcccgg cgtcaatacg ggataatacc gcgccacata   5700
gcagaacttt aaaagtgctc atcattggaa aacgttcttc ggggcgaaaa ctctcaagga   5760
tcttaccgct gttgagatcc agttcgatgt aacccactcg tgcacccaac tgatcttcag   5820
catcttttac tttcaccagc gtttctgggt gagcaaaaac aggaaggcaa aatgccgcaa   5880
aaaagggaat aagggcgaca cggaaatgtt gaatactcat actcttcctt tttcaatatt   5940
attgaagcat ttatcagggt tattgtctca tgagcggata catatttgaa tgtatttaga   6000
aaaataaaca ataggggtt ccgcgcacat ttccccgaaa agtgccacct gacgtc        6056
```

<210> SEQ ID NO 38
<211> LENGTH: 5632
<212> TYPE: DNA
<213> ORGANISM: Artificial Sequence
<220> FEATURE:
<223> OTHER INFORMATION: Description of Artificial Sequence: Synthetic plasmid

<400> SEQUENCE: 38

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagcttggta ccgagctcgg atccgccacc atggcctttg acattgtatg     960
cgacaatgtg gggagagatt ggaagagact ggcccgccag ctgaaagtgt ctgaggccaa    1020
aattgatggg attgaggaga gtaccccccg aagcctgagt gagcaggtaa gggaggctct    1080
gagagtctgg aagattgccg agagggagaa agccacggtg gctggactgg taaaggcact    1140
tcgggcctgc cggctgaacc tagtggctga cctggtggaa gggaggcact cgagtctaga    1200
gggcccgttt aaacccgctg atcagcctcg actgtgcctt ctagttgcca gccatctgtt    1260
gtttgcccct cccccgtgcc ttccttgacc ctggaaggtg ccactcccac tgtcctttcc    1320
taataaaatg aggaaattgc atcgcattgt ctgagtaggt gtcattctat tctggggggt    1380
ggggtggggc aggacagcaa gggggaggat tgggaagaca atagcaggca tgctggggat    1440
gcggtgggct ctatggcttc tgaggcggaa agaaccagct ggggctctag ggggtatccc    1500
cacgcgcccc gtagcggcgc attaagcgcg gcgggtgtgg tggttacgcg cagcgtgacc    1560
gctacacttg ccagcgccct agcgcccgct cctttcgctt tcttcccttc ctttctcgcc    1620
acgttcgccg gctttccccg tcaagctcta aatcgggggc tccctttagg gttccgattt    1680
agtgctttac ggcacctcga ccccaaaaaa cttgattagg gtgatggttc acgtagtggg    1740
ccatcgccct gatagacggt ttttcgccct ttgacgttgg agtccacgtt ctttaatagt    1800
ggactcttgt tccaaactgg aacaacactc aaccctatct cggtctattc ttttgattta    1860
taagggattt tgccgatttc ggcctattgg ttaaaaaatg agctgattta acaaaaattt    1920
aacgcgaatt aattctgtgg aatgtgtgtc agttagggtg tggaaagtcc ccaggctccc    1980
cagcaggcag aagtatgcaa agcatgcatc tcaattagtc agcaaccagg tgtggaaagt    2040
ccccaggctc cccagcaggc agaagtatgc aaagcatgca tctcaattag tcagcaacca    2100
tagtcccgcc cctaactccg cccatcccgc cctaactccg cccagttccg cccattctc     2160
cgccccatgg ctgactaatt ttttttattt atgcagaggc cgaggccgcc tctgcctctg    2220
```

```
agctattcca gaagtagtga ggaggctttt ttggaggcct aggcttttgc aaaaagctcc   2280
cgggagcttg tatatccatt ttcggatctg atcaagagac aggatgagga tcgtttcgca   2340
tgattgaaca agatggattg cacgcaggtt ctccggccgc ttgggtggag aggctattcg   2400
gctatgactg ggcacaacag acaatcggct gctctgatgc cgccgtgttc cggctgtcag   2460
cgcaggggcg cccggttctt tttgtcaaga ccgacctgtc cggtgccctg aatgaactgc   2520
aggacgaggc agcgcggcta tcgtggctgg ccacgacggg cgttccttgc gcagctgtgc   2580
tcgacgttgt cactgaagcg ggaagggact ggctgctatt gggcgaagtg ccggggcagg   2640
atctcctgtc atctcacctt gctcctgccg agaaagtatc catcatggct gatgcaatgc   2700
ggcggctgca tacgcttgat ccggctacct gcccattcga ccaccaagcg aaacatcgca   2760
tcgagcgagc acgtactcgg atggaagccg gtcttgtcga tcaggatgat ctggacgaag   2820
agcatcaggg gctcgcgcca gccgaactgt tcgccaggct caaggcgcgc atgcccgacg   2880
gcgaggatct cgtcgtgacc catggcgatg cctgcttgcc gaatatcatg gtggaaaatg   2940
gccgcttttc tggattcatc gactgtggcc ggctgggtgt ggcggaccgc tatcaggaca   3000
tagcgttggc tacccgtgat attgctgaag agcttggcgg cgaatgggct gaccgcttcc   3060
tcgtgcttta cggtatcgcc gctcccgatt cgcagcgcat cgccttctat cgccttcttg   3120
acgagttctt ctgagcggga ctctggggtt cgaaatgacc gaccaagcga cgcccaacct   3180
gccatcacga gatttcgatt ccaccgccgc cttctatgaa aggttgggct tcggaatcgt   3240
tttccgggac gccggctgga tgatcctcca gcgcggggat ctcatgctgg agttcttcgc   3300 ccacccca ac ttgtttattg cagcttataa tggttacaaa taaagcaata gcatcacaaa   3360 tttcacaat aaagcatttt tttcactgca ttctagttgt ggtttgtcca aactcatcaa   3420
tgtatcttat catgtctgta taccgtcgac ctctagctag agcttggcgt aatcatggtc   3480
atagctgttt cctgtgtgaa attgttatcc gctcacaatt ccacacaaca tacgagccgg   3540
aagcataaag tgtaaagcct ggggtgccta atgagtgagc taactcacat taattgcgtt   3600
gcgctcactg cccgctttcc agtcgggaaa cctgtcgtgc cagctgcatt aatgaatcgg   3660
ccaacgcgcg gggagaggcg gtttgcgtat tgggcgctct tccgcttcct cgctcactga   3720
ctcgctgcgc tcggtcgttc ggctgcggcg agcggtatca gctcactcaa aggcggtaat   3780
acggttatcc acagaatcag gggataacgc aggaaagaac atgtgagcaa aaggccagca   3840
aaaggccagg aaccgtaaaa aggccgcgtt gctggcgttt ttccataggc tccgcccccc   3900
tgacgagcat cacaaaaatc gacgctcaag tcagaggtgg cgaaacccga caggactata   3960
aagataccag gcgtttcccc ctggaagctc cctcgtgcgc tctcctgttc cgaccctgcc   4020
gcttaccgga tacctgtccg cctttctccc ttcgggaagc gtggcgcttt ctcatagctc   4080
acgctgtagg tatctcagtt cggtgtaggt cgttcgctcc aagctgggct gtgtgcacga   4140
accccccgtt cagcccgacc gctgcgcctt atccggtaac tatcgtcttg agtccaaccc   4200
ggtaagacac gacttatcgc cactggcagc agccactggt aacaggatta gcagagcgag   4260
gtatgtaggc ggtgctacag agttcttgaa gtggtggcct aactacggct acactagaag   4320
aacagtattt ggtatctgcg ctctgctgaa gccagttacc ttcggaaaaa gagttggtag   4380
ctcttgatcc ggcaaacaaa ccaccgctgg tagcggtttt tttgtttgca agcagcagat   4440
tacgcgcaga aaaaaggat ctcaagaaga tcctttgatc ttttctacgg ggtctgacgc   4500
tcagtggaac gaaaactcac gttaagggat tttggtcatg agattatcaa aaaggatctt   4560
```

```
cacctagatc cttttaaatt aaaaatgaag ttttaaatca atctaaagta tatatgagta    4620
aacttggtct gacagttacc aatgcttaat cagtgaggca cctatctcag cgatctgtct    4680
atttcgttca tccatagttg cctgactccc cgtcgtgtag ataactacga tacgggaggg    4740
cttaccatct ggccccagtg ctgcaatgat accgcgagac ccacgctcac cggctccaga    4800
tttatcagca ataaccagc cagccggaag ggccgagcgc agaagtggtc ctgcaacttt    4860
atccgcctcc atccagtcta ttaattgttg ccgggaagct agagtaagta gttcgccagt    4920
taatagtttg cgcaacgttg ttgccattgc tacaggcatc gtggtgtcac gctcgtcgtt    4980
tggtatggct tcattcagct ccggttccca acgatcaagg cgagttacat gatccccat     5040 gttgtgcaaa aaagcggtta gctccttcgg tcctccgatc gttgtcagaa gtaagttggc    5100
cgcagtgtta tcactcatgg ttatggcagc actgcataat tctcttactg tcatgccatc    5160
cgtaagatgc ttttctgtga ctggtgagta ctcaaccaag tcattctgag aatagtgtat    5220
gcggcgaccg agttgctctt gcccggcgtc aatacgggat aataccgcgc cacatagcag    5280
aactttaaaa gtgctcatca ttggaaaacg ttcttcgggg cgaaaactct caaggatctt    5340
accgctgttg agatccagtt cgatgtaacc cactcgtgca cccaactgat cttcagcatc    5400
ttttactttc accagcgttt ctgggtgagc aaaaacagga aggcaaaatg ccgcaaaaaa    5460
gggaataagg cgacacgga aatgttgaat actcatactc ttccttttc aatattattg     5520 aagcatttat cagggttatt gtctcatgag cggatacata tttgaatgta tttagaaaaa    5580
taaacaaata ggggttccgc gcacatttcc ccgaaaagtg ccacctgacg tc            5632
```

<210> SEQ ID NO 39
<211> LENGTH: 4758
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 39

```
ctaaattgta agcgttaata ttttgttaaa attcgcgtta aatttttgtt aaatcagctc      60 atttttaac caataggccg aaatcggcaa atcccttat aaatcaaaag aatagaccga      120
gatagggttg agtgttgttc cagttttgaa caagagtcca ctattaaaga acgtggactc    180
caacgtcaaa gggcgaaaaa ccgtctatca gggcgatggc ccactacgtg aaccatcacc    240
ctaatcaagt ttttgggggt cgaggtgccg taaagcacta atcggaacc ctaaagggag     300 cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta gggcgaat tggagctcca     660 ccgcggtggc ggccgctcta gaactagtgg atccccggg ctgcatcccc gatccttatc    720
gctatcgatt cacacaaaaa accaacacac agatgtaatg aaaataaaga tattttattg    780
cggccatcgt gatggcaggt tgggcgtcgc ttggtcggtc atttcgaacc ccagagtccc    840
gctcagaaga actcgtcaag aaggcgatag aaggcgatgc gctgcgaatc gggagcggcg    900
ataccgtaaa gcacgaggaa gcggtcagcc cattcgccgc caagctcttc agcaatatca    960
```

```
cgggtagcca acgctatgtc ctgatagcgg tccgccacac ccagccggcc acagtcgatg    1020
aatccagaaa agcggccatt ttccaccatg atattcggca agcaggcatc gccatgggtc    1080
acgacgagat cctcgccgtc gggcatgcgc gccttgagcc tggcgaacag ttcggctggc    1140
gcgagcccct gatgctcttc gtccagatca tcctgatcga caagaccggc ttccatccga    1200
gtacgtgctc gctcgatgcg atgtttcgct tggtggtcga atgggcaggt agccggatca    1260
agcgtatgca gccgccgcat tgcatcagcc atgatggata ctttctcggc aggagcaagg    1320
tgagatgaca ggagatcctg ccccggcact cgcccaata gcagccagtc ccttcccgct    1380
tcagtgacaa cgtcgagcac agctgcgcaa ggaacgcccg tcgtggccag ccacgatagc    1440
cgcgctgcct cgtcctgcag ttcattcagg gcaccggaca ggtcggtctt gacaaaaaga    1500
accgggcgcc cctgcgctga cagccggaac acggcggcat cagagcagcc gattgtctgt    1560
tgtgcccagt catagccgaa tagcctctcc acccaagcgg ccggagaacc tgcgtgcaat    1620
ccatcttgtt caatcatggt ggctctagcc ttaagttcga gactgttgtg tcagaagaat    1680
caagctgatc tgagtccggt aagctagctt gggctgcagg tcgaaaggcc cggagatgag    1740
gaagaggaga acagcgcggc agacgtgcgc ttttgaagcg tgcagaatgc cgggcctccg    1800
gaggaccttc gggcgcccgc cccgcccctg agcccgcccc tgagcccgcc cccggaccca    1860
ccccttccca gcctctgagc ccagaaagcg aaggagcaaa gctgctattg ccgctgccc    1920 caaaggccta cccgcttcca ttgctcagcg gtgctgtcca tctgcacgag actagtgaga    1980
cgtgctactt ccatttgtca cgtcctgcac gacgcgagct gcgggcgggg gggaacttc    2040 ctgactaggg gaggagtaga aggtggcgcg aaggggccac caaagaacgg agccggttgg    2100
cgcctaccgg ccggtggatg tggaatgtgt gcgaggccag aggccacttg tgtagcgcca    2160
agtgcccagc ggggctgcta aagcgcatgc tccagactgc cttgggaaaa gcgcctcccc    2220
tacccggtag aattcgaacg ctgacgtcat caacccgctc caaggaatcg cgggcccagt    2280
gtcactaggc gggaacaccc agcgcgcgtg cgccctggca ggaagatggc tgtgagggac    2340
aggggagtgg cgccctgcaa tatttgcatg tcgctatgtg ttctgggaaa tcaccataaa    2400
cgtgaaatgt cttcggattt gggaatctta taagttctgt atgagaccac agatcccgtg    2460
agcttcagca agcattattc aagagataat gcttgctgaa gctcattttt tggaaaagct    2520
tatcgatacc gtcgacctcg agggggggcc cggtacccag cttttgttcc ctttagtgag    2580
ggttaattgc gcgcttggcg taatcatggt catagctgtt tcctgtgtga aattgttatc    2640
cgctcacaat tccacacaac atacgagccg gaagcataaa gtgtaaagcc tggggtgcct    2700
aatgagtgag ctaactcaca ttaattgcgt tgcgctcact gcccgctttc cagtcgggaa    2760
acctgtcgtg ccagctgcat taatgaatcg gccaacgcgc ggggagaggc ggtttgcgta    2820
ttgggcgctc ttccgcttcc tcgctcactg actcgctgcg ctcggtcgtt cggctgcggc    2880
gagcggtatc agctcactca aaggcggtaa tacggttatc cacagaatca ggggataacg    2940
caggaaagaa catgtgagca aaaggccagc aaaaggccag gaaccgtaaa aaggccgcgt    3000
tgctggcgtt tttccatagg ctccgccccc ctgacgagca tcacaaaaat cgacgctcaa    3060
gtcagaggtg gcgaaacccg acaggactat aaagatacca ggcgtttccc cctggaagct    3120
ccctcgtgcg ctctcctgtt ccgaccctgc cgcttaccgg atacctgtcc gcctttctcc    3180
cttcgggaag cgtggcgctt tctcatagct cacgctgtag gtatctcagt tcggtgtagg    3240
tcgttcgctc caagctgggc tgtgtgcacg aaccccccgt tcagcccgac cgctgcgcct    3300
tatccggtaa ctatcgtctt gagtccaacc cggtaagaca cgacttatcg ccactggcag    3360
```

```
cagccactgg taacaggatt agcagagcga ggtatgtagg cggtgctaca gagttcttga    3420
agtggtggcc taactacggc tacactagaa ggacagtatt tggtatctgc gctctgctga    3480
agccagttac cttcggaaaa agagttggta gctcttgatc cggcaaacaa accaccgctg    3540
gtagcggtgg ttttttttgtt tgcaagcagc agattacgcg cagaaaaaaa ggatctcaag    3600
aagatccttt gatcttttct acggggtctg acgctcagtg gaacgaaaac tcacgttaag    3660
ggattttggt catgagatta tcaaaaagga tcttcaccta gatcctttta aattaaaaat    3720
gaagttttaa atcaatctaa agtatatatg agtaaacttg gtctgacagt taccaatgct    3780
taatcagtga ggcacctatc tcagcgatct gtctatttcg ttcatccata gttgcctgac    3840
tccccgtcgt gtagataact acgatacggg agggcttacc atctggcccc agtgctgcaa    3900
tgataccgcg agacccacgc tcaccggctc cagatttatc agcaataaac cagccagccg    3960
gaagggccga gcgcagaagt ggtcctgcaa ctttatccgc ctccatccag tctattaatt    4020
gttgccggga agctagagta agtagttcgc cagttaatag tttgcgcaac gttgttgcca    4080
ttgctacagg catcgtggtg tcacgctcgt cgtttggtat ggcttcattc agctccggtt    4140
cccaacgatc aaggcgagtt acatgatccc ccatgttgtg caaaaaagcg gttagctcct    4200
tcggtcctcc gatcgttgtc agaagtaagt tggccgcagt gttatcactc atggttatgg    4260
cagcactgca taattctctt actgtcatgc catccgtaag atgcttttct gtgactggtg    4320
agtactcaac caagtcattc tgagaatagt gtatgcggcg accgagttgc tcttgcccgg    4380
cgtcaatacg ggataatacc gcgccacata gcagaacttt aaaagtgctc atcattggaa    4440
aacgttcttc ggggcgaaaa ctctcaagga tcttaccgct gttgagatcc agttcgatgt    4500
aacccactcg tgcacccaac tgatcttcag catcttttac tttcaccagc gtttctgggt    4560
gagcaaaaac aggaaggcaa aatgccgcaa aaaagggaat aagggcgaca cggaaatgtt    4620
gaatactcat actcttcctt tttcaatatt attgaagcat ttatcagggt tattgtctca    4680
tgagcggata catatttgaa tgtatttaga aaaataaaca aataggggtt ccgcgcacat    4740
ttccccgaaa agtgccac                                                  4758
```

<210> SEQ ID NO 40
<211> LENGTH: 4756
<212> TYPE: DNA
<213> ORGANISM: Artificial Sequence
<220> FEATURE:
<223> OTHER INFORMATION: Description of Artificial Sequence: Synthetic plasmid

<400> SEQUENCE: 40

```
ctaaattgta agcgttaata ttttgttaaa attcgcgtta aattttttgtt aaatcagctc     60 attttttaac caataggccg aaatcggcaa aatcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt ttttttgggt cgaggtgccg taaagcacta atcggaacc ctaaagggag    300 cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
```

```
taaaacgacg gccagtgagc gcgcgtaata cgactcacta tagggcgaat tggagctcca    660
ccgcggtggc ggccgctcta gaactagtgg atccccccggg ctgcatcccc gatccttatc   720
gctatcgatt cacacaaaaa accaacacac agatgtaatg aaaataaaga tattttattg    780
cggccatcgt gatggcaggt tgggcgtcgc ttggtcggtc atttcgaacc ccagagtccc    840
gctcagaaga actcgtcaag aaggcgatag aaggcgatgc gctgcgaatc gggagcggcg    900
ataccgtaaa gcacgaggaa gcggtcagcc cattcgccgc caagctcttc agcaatatca    960
cgggtagcca acgctatgtc ctgatagcgg tccgccacac ccagccggcc acagtcgatg   1020
aatccagaaa agcggccatt ttccaccatg atattcggca agcaggcatc gccatgggtc   1080
acgacgagat cctcgccgtc gggcatgcgc gccttgagcc tggcgaacag ttcggctggc   1140
gcgagcccct gatgctcttc gtccagatca tcctgatcga caagaccggc ttccatccga   1200
gtacgtgctc gctcgatgcg atgtttcgct tggtggtcga atgggcaggt agccggatca   1260
agcgtatgca gccgccgcat tgcatcagcc atgatggata ctttctcggc aggagcaagg   1320
tgagatgaca ggagatcctg ccccggcact cgcccaata gcagccagtc ccttcccgct   1380
tcagtgacaa cgtcgagcac agctgcgcaa ggaacgcccg tcgtggccag ccacgatagc   1440
cgcgctgcct cgtcctgcag ttcattcagg gcaccggaca ggtcggtctt gacaaaaaga   1500
accgggcgcc cctgcgctga cagccggaac acggcggcat cagagcagcc gattgtctgt   1560
tgtgcccagt catagccgaa tagcctctcc acccaagcgg ccggagaacc tgcgtgcaat   1620
ccatcttgtt caatcatggt ggctctagcc ttaagttcga gactgttgtg tcagaagaat   1680
caagctgatc tgagtccggt aagctagctt gggctgcagg tcgaaaggcc cggagatgag   1740
gaagaggaga acagcgcggc agacgtgcgc ttttgaagcg tgcagaatgc cgggcctccg   1800
gaggaccttc gggcgcccgc cccgcccctg agcccgcccc tgagcccgcc ccggaccca    1860
cccttccca gcctctgagc ccagaaagcg aaggagcaaa gctgctattg ccgctgccc    1920
caaaggccta cccgcttcca ttgctcagcg gtgctgtcca tctgcacgag actagtgaga   1980
cgtgctactt ccatttgtca cgtcctgcac gacgcgagct gcggggcggg gggaacttc    2040
ctgactaggg gaggagtaga aggtggcgcg aaggggccac caaagaacgg agccggttgg   2100
cgcctaccgg ccggtggatg tggaatgtgt gcgaggccag aggccacttg tgtagcgcca   2160
agtgcccagc ggggctgcta aagcgcatgc tccagactgc cttgggaaaa gcgcctcccc   2220
tacccggtag aattcgaacg ctgacgtcat caacccgctc caaggaatcg cgggcccagt   2280
gtcactaggc gggaacaccc agcgcgcgtg cgccctggca ggaagatggc tgtgagggac   2340
aggggagtgg cgccctgcaa tatttgcatg tcgctatgtg ttctgggaaa tcaccataaa   2400
cgtgaaatgt ctttggattt gggaatctta aagttctgt atgagaccac agatcccgcg    2460
gatccttgaa cctgatttca agagaatcag gttcaggatc cgcttttttg gaaaagctta   2520
tcgataccgt cgacctcgag ggggggcccg gtacccagct tttgttccct ttagtgaggg   2580
ttaattgcgc gcttggcgta atcatggtca gctgttttc ctgtgtgaaa ttgttatccg    2640
ctcacaattc cacacaacat acgagccgga agcataaagt gtaaagcctg gggtgcctaa   2700
tgagtgagct aactcacatt aattgcgttg cgctcactgc ccgctttcca gtcgggaaac   2760
ctgtcgtgcc agctgcatta atgaatcggc caacgcgcgg ggagaggcgg tttgcgtatt   2820
gggcgctctt ccgcttcctc gctcactgac tcgctgcgct cggtcgttcg gctgcggcga   2880
gcggtatcag ctcactcaaa ggcggtaata cggttatcca cagaatcagg ggataacgca   2940
```

-continued

```
ggaaagaaca tgtgagcaaa aggccagcaa aaggccagga accgtaaaaa ggccgcgttg      3000
ctggcgtttt tccataggct ccgccccect gacgagcatc acaaaaatcg acgctcaagt      3060
cagaggtggc gaaacccgac aggactataa agataccagg cgtttccccc tggaagctcc      3120
ctcgtgcgct ctcctgttcc gaccctgccg cttaccggat acctgtccgc ctttctccct      3180
tcgggaagcg tggcgcttc tcatagctca cgctgtaggt atctcagttc ggtgtaggtc      3240
gttcgctcca agctgggctg tgtgcacgaa ccccccgttc agcccgaccg ctgcgcctta      3300
tccggtaact atcgtcttga gtccaacccg gtaagacacg acttatcgcc actggcagca      3360
gccactggta acaggattag cagagcgagg tatgtaggcg gtgctacaga gttcttgaag      3420
tggtggccta actacggcta cactagaagg acagtatttg gtatctgcgc tctgctgaag      3480
ccagttacct tcggaaaaag agttggtagc tcttgatccg gcaaacaaac caccgctggt      3540
agcggtggtt ttttgtttg caagcagcag attacgcgca gaaaaaaagg atctcaagaa      3600
gatcctttga tcttttctac ggggtctgac gctcagtgga acgaaaactc acgttaaggg      3660
attttggtca tgagattatc aaaaaggatc ttcacctaga tccttttaaa ttaaaaatga      3720
agttttaaat caatctaaag tatatatgag taaacttggt ctgacagtta ccaatgctta      3780
atcagtgagg cacctatctc agcgatctgt ctatttcgtt catccatagt tgcctgactc      3840
cccgtcgtgt agataactac gatacgggag ggcttaccat ctggccccag tgctgcaatg      3900
ataccgcgag acccacgctc accggctcca gatttatcag caataaacca gccagccgga      3960
agggccgagc gcagaagtgg tcctgcaact ttatccgcct ccatccagtc tattaattgt      4020
tgccgggaag ctagagtaag tagttcgcca gttaatagtt tgcgcaacgt tgttgccatt      4080
gctacaggca tcgtggtgtc acgctcgtcg tttggtatgg cttcattcag ctccggttcc      4140
caacgatcaa ggcgagttac atgatccccc atgttgtgca aaaaagcggt tagctccttc      4200
ggtcctccga tcgttgtcag aagtaagttg gccgcagtgt tatcactcat ggttatggca      4260
gcactgcata attctcttac tgtcatgcca tccgtaagat gcttttctgt gactggtgag      4320
tactcaacca agtcattctg agaatagtgt atgcggcgac cgagttgctc ttgcccggcg      4380
tcaatacggg ataataccgc gccacatagc agaactttaa aagtgctcat cattggaaaa      4440
cgttcttcgg ggcgaaaact ctcaaggatc ttaccgctgt tgagatccag ttcgatgtaa      4500
cccactcgtg cacccaactg atcttcagca tcttttactt tcaccagcgt ttctgggtga      4560
gcaaaaacag gaaggcaaaa tgccgcaaaa aagggaataa gggcgacacg gaaatgttga      4620
atactcatac tcttcctttt tcaatattat tgaagcattt atcagggtta ttgtctcatg      4680
agcggataca tatttgaatg tatttagaaa aataaacaaa tagggggttcc gcgcacattt      4740 ccccgaaaag tgccac                                                      4756
```

<210> SEQ ID NO 41
<211> LENGTH: 78
<212> TYPE: PRT
<213> ORGANISM: Cricetulus griseus

<400> SEQUENCE: 41

```
Phe Asp Ile Val Cys Asp Asn Val Gly Arg Asp Trp Lys Arg Leu Ala
1               5                   10                  15

Arg Gln Leu Lys Val Ser Glu Ala Lys Ile Asp Gly Ile Glu Glu Arg
            20                  25                  30

Tyr Pro Arg Ser Leu Ser Glu Gln Val Arg Glu Ala Leu Arg Val Trp
        35                  40                  45
```

```
Lys Ile Ala Glu Arg Glu Lys Ala Thr Val Ala Gly Leu Val Lys Ala
        50                  55                  60

Leu Arg Ala Cys Arg Leu Asn Leu Val Ala Asp Leu Val Glu
65                  70                  75
```

```
<210> SEQ ID NO 42
<211> LENGTH: 234
<212> TYPE: DNA
<213> ORGANISM: Cricetulus griseus

<400> SEQUENCE: 42
tttgacattg tatgcgacaa tgtggggaga gattggaaga gactggcccg ccagctgaaa      60
gtgtctgagg ccaaaattga tgggattgag gagaggtacc cccgaagcct gagtgagcag     120
gtaagggagg ctctgagagt ctggaagatt gccgagaggg agaaagccac ggtggctgga     180
ctggtaaagg cacttcgggc ctgccggctg aacctggtgg ctgacctggt ggaa           234

<210> SEQ ID NO 43
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gaattcgcca ccatgacaga tcttgtagc                                        29

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gaattcgtga acacatttaa ttacca                                           26
```